(12) United States Patent
Edelson-Averbukh et al.

(10) Patent No.: US 11,600,359 B2
(45) Date of Patent: Mar. 7, 2023

(54) METHODS AND SYSTEMS FOR ANALYSIS OF MASS SPECTROMETRY DATA

(71) Applicant: IMPERIAL COLLEGE OF SCIENCE, TECHNOLOGY AND MEDICINE, London (GB)

(72) Inventors: Marina Edelson-Averbukh, London (GB); Leszek J. Frasinski, London (GB); Taran Driver, London (GB); David Klug, London (GB); Jon P. Marangos, London (GB)

(73) Assignee: IMPERIAL COLLEGE OF SCIENCE, TECHNOLOGY AND MEDICINE, London (GB)

( * ) Notice: Subject to any disclaimer, the term of this patent is extended or adjusted under 35 U.S.C. 154(b) by 1019 days.

(21) Appl. No.: 16/333,902

(22) PCT Filed: Sep. 15, 2017

(86) PCT No.: PCT/GB2017/052745
§ 371 (c)(1),
(2) Date: Mar. 15, 2019

(87) PCT Pub. No.: WO2018/051120
PCT Pub. Date: Mar. 22, 2018

(65) Prior Publication Data
US 2019/0206509 A1    Jul. 4, 2019

(30) Foreign Application Priority Data
Sep. 16, 2016  (GB) ...................................... 1615818

(51) Int. Cl.
*G16B 15/00* (2019.01)
*G16C 20/20* (2019.01)
(Continued)

(52) U.S. Cl.
CPC ............. *G16B 15/00* (2019.02); *G16C 20/20* (2019.02); *H01J 49/0036* (2013.01); *G16C 20/70* (2019.02)

(58) Field of Classification Search
CPC ........ G16B 15/00; G16C 20/20; G16C 20/70; G01N 27/62; G06F 17/18; H01J 49/00;
(Continued)

(56) References Cited

U.S. PATENT DOCUMENTS

2006/0217926 A1    9/2006  Dieterle et al.
2009/0307248 A1*  12/2009  Moser .................. G06K 9/6298
(Continued)

FOREIGN PATENT DOCUMENTS

EP       1705578 A1    9/2006
WO    WO-2010/136765 A1   12/2010

OTHER PUBLICATIONS

International Search Report and Written Opinion issued in PCT Patent Application No. PCT/GB2017/052745 dated Mar. 13, 2018.
(Continued)

*Primary Examiner* — Jason L McCormack
(74) *Attorney, Agent, or Firm* — ,Marshall, Gerstein & Borun LLP

(57) ABSTRACT

A method of analysing a structure of a composition of matter in a sample includes obtaining a data set comprising a plurality of spectra from the composition, from a first method of analysis, dividing each of the spectra into a plurality of bins, determining a control parameter or parameters indicative of synchronised fluctuations in signal intensity across some or all channels, resulting in universal correlation between said bins, and determining a partial covariance of different bins across the plurality of spectra using the control parameter to correct the correlation of intensity fluctuations between said bins.

32 Claims, 46 Drawing Sheets

(51) Int. Cl.
  *H01J 49/00*  (2006.01)
  *G16C 20/70*  (2019.01)
(58) Field of Classification Search
  CPC .... H01J 49/02; H01J 49/0009; H01J 49/0027; H01J 49/0031; H01J 49/0036; H01J 49/26
  USPC .................................. 702/19; 250/281, 282
  See application file for complete search history.

(56) References Cited

U.S. PATENT DOCUMENTS

2014/0138537 A1* 5/2014 Grothe, Jr. .............. H01J 49/26
                                                       250/282
2015/0168292 A1   6/2015 Otsuka

OTHER PUBLICATIONS

Frasinski L.J, et al., "Covariance mapping techniques," *Journal of Physics B, Atomic Molecular and Optical Physics*, vol. 49, No. 15 (Jul. 2016).
Marshall D.D. et al., "Combining DI-ESI-MS and NMR datasets for metabolic profiling," *METABOLOMICS*, vol. 11, No. 2 (Jul. 2014).
Worley B. et al., "Generalized adaptive intelligent binning of multiway data," *Chemometrics and Intelligent Laboratory Systems*, vol. 146, (May 2015).
Worley B. et al., "Mvapack: A Complete Data Handling Package for NMR Metabolomics," *ACS Chemical Biology*, vol. 9, No. 5 (Feb. 2014).
Byrnes CH. I. et al., "A New Approach to Spectral Estimation: A Tunable High-Resolution Spectral Estimator," *IEEE Transactions on Signal Processing, IEEE Service Center*, New York, NY, vol. 48, No. 11 (Nov. 2000).

* cited by examiner

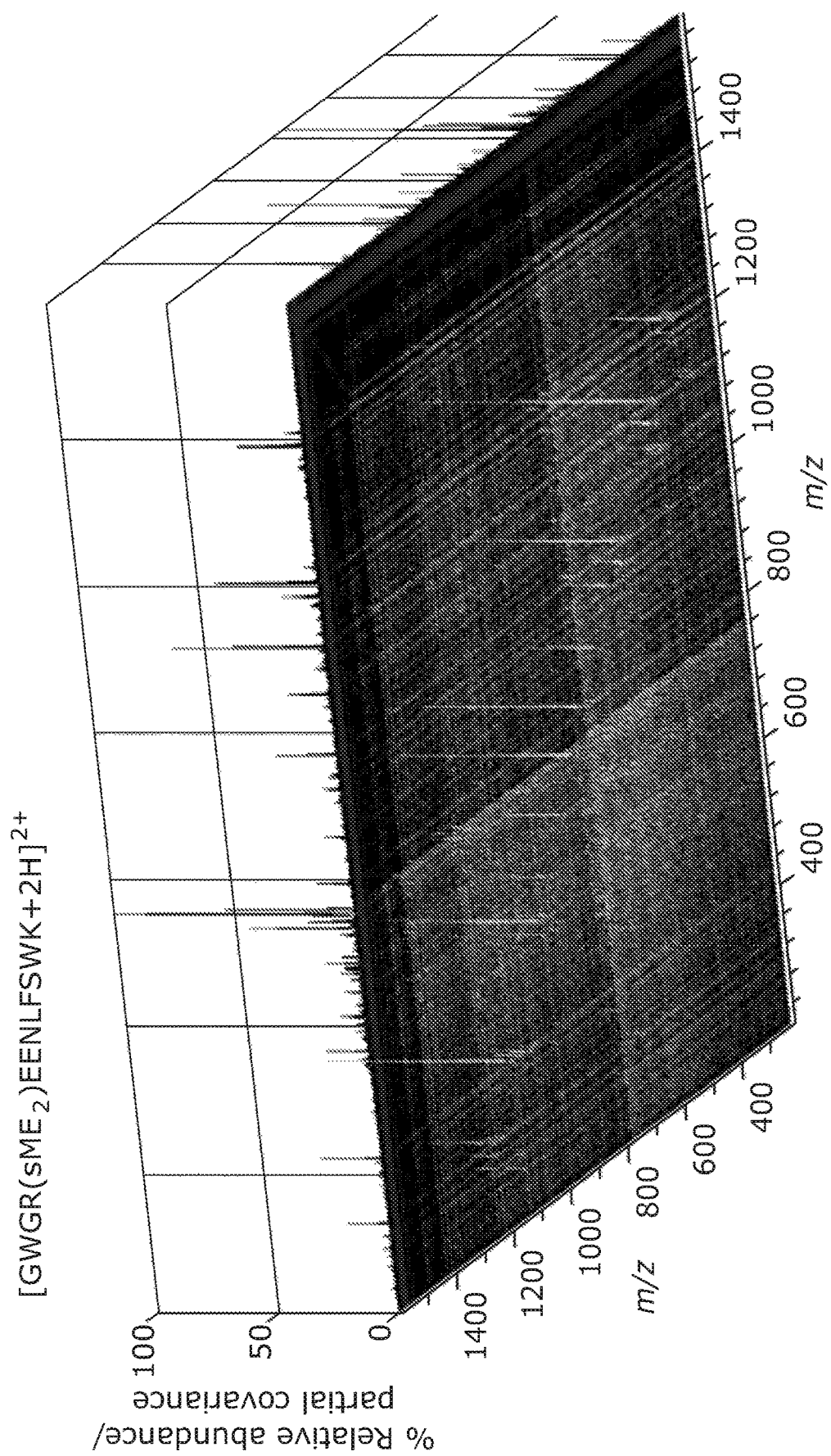

1D mass spectrometry

54/95 intensity-filtered peaks identified as structural signal 2D pC2DMS

35/30 intensity-filtered peaks identified as structural signal 1D mass spectrometry 23/24 intensity-filtered peaks identified as structural signal 2D pC2DMS 26/25 intensity-filtered peaks identified as structural signal Mascot MS/MS ions search Protein Prospector MS-Tag search 1D mass spectrometry 25/40 intensity-filtered peaks identified as structural signal 2D pC2DMS 22/21 intensity-filtered peaks identified as structural signal

1D mass spectrometry

25/40 intensity-filtered peaks identified as structural signal

2D pC2DMS

19/23 intensity-filtered peaks identified as structural signal

Mascot MS/MS ions search

Protein Prospector MS-Tag search 1D mass spectrometry

33/41 intensity-filtered peaks identified as structural signal 2D pC2DMS

31/30 intensity-filtered peaks identified as structural signal 1D mass spectrometry 33/50 intensity-filtered peaks identified as structural signal 2D pC2DMS 23/20 intensity-filtered peaks identified as structural signal Mascot MS/MS ions search Protein Prospector MS-Tag search 1D mass spectrometry 23/29 Intensity-filtered peaks identified as structural signal 2D pC2DMS 18/18 Intensity-filtered peaks identified as structural signal

*Mascot MS/MS ions search*

Protein Prospector MS-Tag search
No way to search with the required sucstitution

METHODS AND SYSTEMS FOR ANALYSIS OF MASS SPECTROMETRY DATA

TECHNICAL FIELD

The present invention relates to methods of analysing chemical and/or biological samples to determine the structure of one or more of the component parts of the sample. The present invention also relates to systems and apparatus for performing such methods.

BACKGROUND

Laboratory analytical techniques and equipment have advanced to such a degree of power and sensitivity that they are able to produce large quantities of data when analysing even relatively simple samples. The challenge for the analyst is then in reviewing this data to derive useful information about the sample. This is particularly the case when the sample under analysis is a complex mixture of materials and/or represents a sample of biological origin, such as one or more proteins or peptides, nucleic acids or metabolites.

Mass spectrometry (MS) is a popular and effective method for analysing the structure of biomolecules such as proteins, DNA, lipids or metabolites. The major applications of biomolecular MS in clinical biology are in protein studies (proteomics). The primary aim of proteomic MS analysis is to establish the sequence of the biomolecular building blocks, (i.e. amino acids), and the covalent post-translational modifications (PTMs) of particular proteins. To do so, the biomolecules are typically first cut into smaller fragments, e.g. acting on proteins with enzymes to obtain peptides, the peptides are sent to a mass spectrometer via soft ionisation techniques [such as electrospray ionisation (ESI) or matrix assisted laser desorption-ionisation (MALDI)], where in tandem mass spectrometry (MS/MS) they are fragmented even further to obtain peptide structure details (often by collision induced dissociation, CID), and the spectral information is pieced together to deduce the full structure of the original biomolecule.

A reliable data interpretation of complex biomolecular fragment spectra generated during the MS/MS step is one of the biggest challenges of current MS technology. This crucial step of interpreting the data output from the spectrometer has been achieved by (i) matching the measured spectrum to the expected "theoretical" one on the basis of the structure of the known peptides derived from a protein database combined with general peptide fragmentation rules, (ii) matching the measured mass spectrum to a database of experimental spectra, or finally (iii) a first-principles structural reconstruction using the measured spectrum and the peptide fragmentation rules only (so-called de novo algorithms). In each case, the strength of a match between a given peptide structure and the measured mass spectrum is expressed as a peptide score, and those scores exceeding an empirical threshold or sufficiently separated from scores for all other candidate peptide structures are taken to correspond to correct identifications. Low-confidence (low-score) assignment of a given spectrum to correct structure, or best-match to incorrect structure, turns out to be a quite common place.

These methods have low success rates of interpretation, meaning that 50% or more of the measured MS spectra can be wasted. The poor efficiency of assignment, even often of very high quality fragment mass spectra, arises from MS/MS method limitations, strong sequence-dependent character of peptide fragmentations, unexpected protein PTMs, insufficient signal to noise ratio of multiple sequence-informative peaks, genetic mutations, signal overlapping (in particular for longer peptide and protein sequences) and other causes.

To alleviate this ambiguity mass resolution has been increased far beyond integer mass-to-charge (m/z) ratio to identify atoms of MS fragments from their accurate masses, e.g. to tell apart two nitrogen atoms (28.007 Da) from one carbon and one oxygen atom (27.995 Da). Although this high resolution MS reduces considerably the number of prospective hits (e.g. peptide sequence options in the case of proteomics) generated by matching the experimental data to databases or derived directly from the mass spectra (such as in de-novo sequencing), it does not provide by itself any experimental evidence for the assumed origin of the biomolecular fragments that is derived from the observed mass-to-charge ratios. This leads to multiple false positive/negative results in the identification of fragments characterised by highly accurate m/z, limiting significantly the capability and reliability of biomolecular structural analysis using MS.

Fragment mass spectra of peptides and proteins commonly display signals of unusual origin caused by the strong dependence of the fragmentation patterns on amino acid sequence, peptide length, charge state, modifying groups and other factors. A significant proportion of these fragment ions miss identification or do not undergo a correct interpretation, frequently causing the spectrum-to-structure matching failure. Furthermore, low relative peak intensities ("relative abundances") and poor signal to noise ratios of standard fragments of a well-known origin are also very common, which leads to them being missed by the existing MS interpretation algorithms. Indeed, any interpretation of a mass spectrum must employ some threshold on the relative abundance of spectral peaks, below which those peaks within a certain mass-to-charge (m/z) range are not taken into consideration. As a result of the finite signal-to-noise ratio, structure determining algorithms work using a limited number of spectral signals ('good peaks'), which is currently limited to being defined purely on the grounds of relative intensities. If low-intensity MS peaks bearing crucial structural information are not taken into consideration, the algorithm will produce low-confidence structural assignment that eventually leads to lack of successful spectral interpretation and correct sample component analysis. Increasing the mass accuracy and mass resolution of the MS instruments can only partially solve this problem by resolving overlapping signals and reducing a number of candidate fragment ions for relatively intense "unknown" fragments. So, to an extent, can alternative fragmentation techniques by causing different fragmentation patterns. However, a general solution for the poor interpretation efficiency of the tandem mass spectra, independent of the fragment origin complexity or the ion relative abundance, is clearly lacking.

SUMMARY OF THE DISCLOSURE

It is therefore desired to provide means for analysing data such as that produced by a mass spectrometer to reduce wasted data sets and/or to more accurately and reliably determine the structure of compounds under analysis.

In a first aspect, the invention provides a method of analysing a structure of a composition of matter in a sample comprising:
  obtaining a data set comprising a plurality of spectra from the composition, from a first method of analysis;
  dividing each of the spectra into a plurality of bins;

determining a control parameter or parameters indicative of synchronised fluctuations in signal intensity across some or all bins, resulting in universal correlation between said bins;

determining a partial covariance of different bins across the plurality of spectra using the control parameter or parameters to correct the correlation of intensity fluctuations between said bins.

The term "bin" is intended to refer to a channel, section or region of a spectrum relating to a value or range of values associated with a physico-chemical property.

Preferably, the method further comprises two-dimensional mapping the partial covariance between said different bins of the spectra. This may comprise mapping the partial covariance of the correlation of the fluctuation of intensities in the spectra, the correlation being corrected according to the values of the control parameters. Mapping refers to the representation of the partial covariance between said different bins as a two-dimensional map.

The inventors have found that some calculated partial covariance peaks on the maps exhibit portions which are negative. However, such peaks may be considered specious because while they may be superficially plausible they can be incorrect as in the idealised model partial covariance cannot be negative. The method preferably further comprises identifying one or more specious partial covariance peaks having a negative component of a magnitude greater than 100% of its total positive magnitude and removing the specious partial covariance peaks from the map.

In some embodiments, the data set comprises a plurality of nuclear magnetic resonance (NMR) spectra, electron spin resonance (ESR) spectra, infra-red (IR) spectra, Raman spectra, UV/fluorescence spectra or photoelectron spectra. Correspondingly, the method of analysis may comprise NMR spectroscopy, ESR spectroscopy, IR spectroscopy, Raman spectroscopy, UV/fluorescence spectroscopy or photoelectron spectroscopy.

All of these measurement methods are suited to the analysis approach as the data comprises a plurality of spectra that can be divided into bins. In all it is possible to identify a control parameter that is indicative of synchronised fluctuations that can be employed in the partial covariance analysis.

In a preferred embodiment, the data set comprises a plurality of mass spectra. Preferably, each of the mass spectra comprises a relative abundance or intensity measurement versus a mass to charge ratio.

In preferred embodiments, the composition of matter comprises a plurality of ions, generated under decomposition analysis.

In some embodiments, the method further comprises determining a statistical significance of each peak or element in the partial covariance map. Such a method may comprise computing a statistical significance $S(X,Y)$ according to the equation $$S(X,Y)=V[p\ \mathrm{Cov}(X,Y;I)]/\sigma(V)$$

where V is a volume under a partial covariance peak or a volume of a section of the partial covariance function $p\mathrm{Cov}(X,Y;I)$, and $\sigma(V)$ comprises a measure of the variance of the volume under the peak or the variance of a volume under the section, for example using jacknife resampling.

In some embodiments, the method comprises determining a statistical significance of each peak or section comprises computing a statistical significance $S(X,Y)$ according to the equation $$S(X,Y)=p\ \mathrm{Cov}(X,Y;I)/\sigma(p\ \mathrm{Cov}(X,Y;I))$$

where $p\mathrm{Cov}(X,Y;I)$ is the value of the partial covariance between bin X and bin Y or a measure of the combined partial covariance between bin or bins X and bin or bins Y and $\sigma(p\mathrm{Cov}(X,Y;I))$ comprises a measure of the variance of the value of the partial covariance between bins X and Y or a measure of the variance of a measure of the combined partial covariance between bin or bins X and bin or bins Y.

Preferably, the control parameters comprise an operating parameter or parameters of the apparatus generating the data sets and/or one or more measures of the experimental conditions under which the plurality of spectra was generated, for example mechanical, electrical, chemical, magnetic, optical and/or thermal conditions.

In preferred embodiments, the method of analysis comprises mass spectrometry and the control parameter comprises a measure of any of the following operating parameters: total ion current for each spectrum; a total number of ions generated for each spectrum; a measure of signal intensity over one or more parts of the spectrum; a prescan ion current; a relative sample density; a pressure of gas in an ion trap, ion guide and/or collision cell; a rate of flow of ions into a mass analyser; an intensity and/or pulse duration of ionising radiation; electrospray ionisation capillary voltage; rf and dc voltages applied to an ion trap; ion trap q-value; a voltage applied to one or more of a tube lens, gate lens, focusing lens, ion tunnel or multipole ion guide of the mass spectrometer, a time for which a voltage is applied to one or more of a tube lens, gate lens, focusing lens, ion tunnel or multipole ion guide of the mass spectrometer.

Preferably, the control parameter comprises a measure of intensity of at least a selected portion of each of the spectra.

Preferably, the control parameters are derived from an integration over at least a portion of each spectrum.

The spectra may relate to mass to charge ratio, kinetic energy or time of flight of analyte particles, absorption or emission frequency or chemical shift, for example according to the particular method of analysis used.

In a preferred embodiment, the method of analysis comprises mass spectrometry and the control parameter is derived from an integration of the spectra at one or more detected mass to charge ratios (m/z). Preferably, the control parameter comprises an integration of the spectrum across all detected mass to charge ratios.

In preferred embodiments, the method of analysis comprises tandem mass spectrometry. In such embodiments, the control parameter is derived from an integration of each spectrum at or about an m/z ratio corresponding to a parent ion or neutral loss thereof or a fragment ion or a neutral loss thereof. Additionally or alternatively, the method of analysis may comprise dissociating one or more parent ions by means of one or more of collision induced dissociation (CID), electron transfer dissociation (ETD), electron capture dissociation (ECD), electron detachment dissociation (EDD), photodissociation, laser induced dissociation or surface induced dissociation (SID).

In preferred embodiments, the sample comprises one or more peptides or proteins. Such a sample may, prior to analysing, be exposed to one or more enzymes to at least partially digest one or more of the proteins or peptides present, optionally followed by chromatographic separation of the digested proteins or peptides.

Preferably, the method comprises comprising ranking statistical significance of each spectral correlation in the partial covariance map relative to the most statistically significant peak. Preferably the spectra are mass spectra and the ranking provides information indicative of a parent ion origin of one or more daughter or granddaughter ions.

In preferred embodiments, the ranking provides information indicative of the probability of a partial covariance signal representing a true correlation between fragment ions, a true correlation between fragment ions providing information indicative of a parent ion origin of one or more daughter or granddaughter ions. Preferably, the information indicative of the probability of a partial covariance signal representing a true correlation between fragment ions is provided as a map or list of pairs of statistically significant correlating fragment ions. It is preferred that the map or list of pairs of statistically significant correlating fragment ions is compared to one or more spectral databases to determine at least part of the structure of the composition of matter.

Preferably, the sample comprises one or more proteins or peptides and the information indicative of the parent ion origin of one or more daughter or granddaughter ions is used to determine a structure of the proteins or peptides. Additionally or alternatively, the sample comprises DNA, human or animal metabolites or lipids and the information indicative of the parent ion origin of one or more daughter or granddaughter ions is used to determine a structure of the DNA, RNA, human or animal metabolites or lipids.

BRIEF DESCRIPTION OF THE DRAWINGS

Embodiments of the present invention will now be described with reference to the following drawings.

DETAILED DESCRIPTION

Figure 1A:
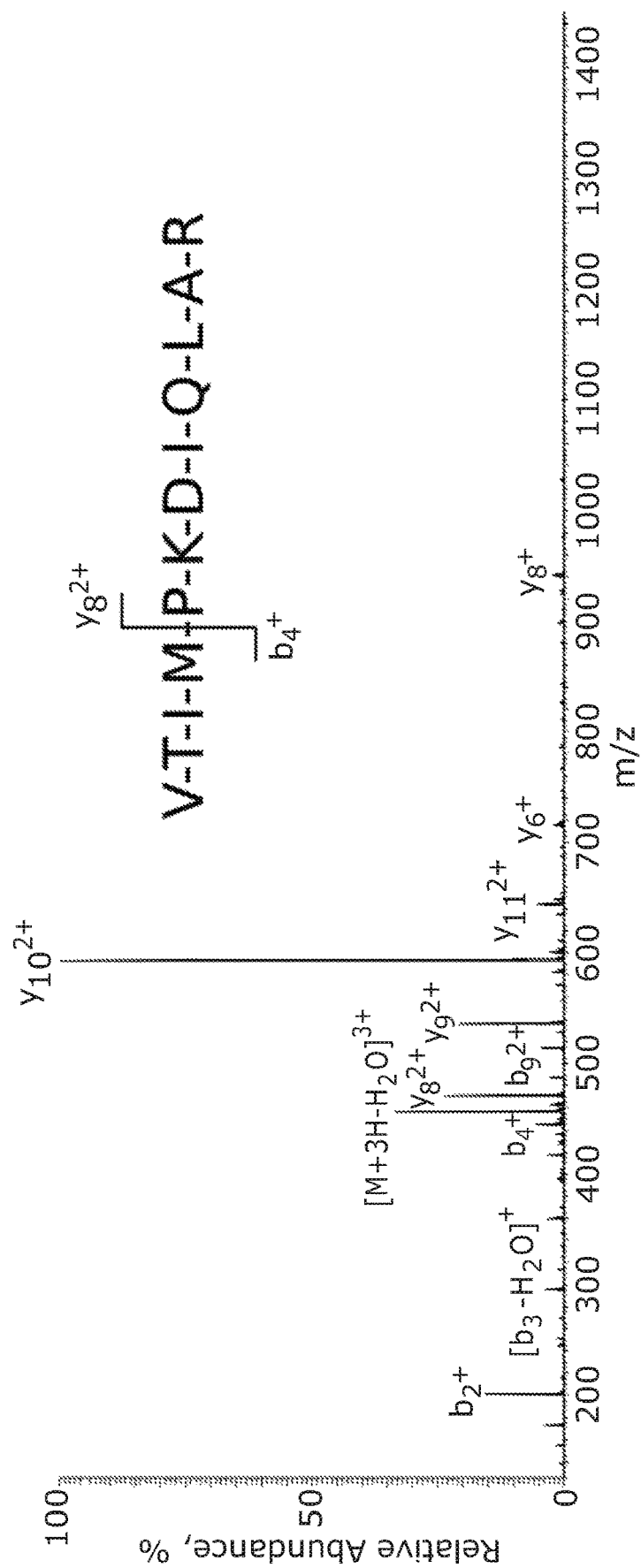
FIG. 1(a) shows a CID spectrum of [VTIMPK(Ac)DIQLAR+3H]$^{3+}$, main fragments are annotated.

Embodiments of the present invention provide methods for analysing the structure of one or more compounds by obtaining a data set containing data indicative of a physical and/or chemical property of the compound and determining a partial covariance of at least a portion of the data.

Covariance mapping mass spectroscopy was developed as an alternative tool to coincidence techniques for the study of mechanisms of radiation-induced molecular fragmentation. Whilst true coincidence measurements deterministically trace the simultaneously detected fragment ions and electrons to a single parent atom, molecule or cluster, covariance mapping exploits statistical correlations between the shot-to-shot fragment intensities to obtain the same information. This can be used in situations, where there are multiple decompositions, which completely precludes the possibility of coincidence detection.

Covariance mapping rests upon calculation of the covariance function, Cov(X,Y), between the intensity at each pair of different signal channels, $X_i$ and $Y_i$, over a series of i=1, 2, . . . , N measurements:

$$\mathrm{Cov}(X,Y) = \langle (X - \langle X \rangle)(Y - \langle Y \rangle) \rangle, \quad (1)$$

where the angular brackets denote averaging over the N measurements, e.g.

$$\langle X \rangle = \frac{1}{N} \sum_{i=1}^{N} X_i.$$

Positive covariance means that the two intensities fluctuate together, indicating the common origin from the same parent Z, either directly: Z→X+Y, or via an intermediate decomposition stage: Z→X+X$_1$, X$_1$→Y+Y$_1$. Zero covariance indicates lack of correlation, meaning the fragments originate from unrelated decomposition processes. Interpretation of a negative covariance, although sometimes assumed to indicate the origin of the fragments from competing processes, is in fact more complicated. It is possible to display the fragment covariance functions as a two-dimensional map, where the x- and y-axes correspond to m/z ratios of the various fragments, while the covariance value may be colour-coded.

A three-dimensional analogue of covariance mapping spectroscopy, exploiting statistical correlations between three fragments, has also been developed for some applications. The basic requirement for the successful application of the covariance mapping technique is close enough to 100% fragment detection efficiency (typically 70% or higher). Indeed, if a substantial number of X or Y fragments is lost, their statistical fluctuations reflect inefficient detection instead of a common origin.

Covariance mapping spectroscopy has previously been effective, for example, in unravelling the decomposition mechanisms of so-called 'hollow atoms'—unstable states of matter formed by intense X-ray irradiation—or in correlating photoelectron emission with fragmentation of hydrocarbons in intense infrared fields. Nevertheless, covariance mapping is often plagued by spurious correlations stemming from fluctuations in some global parameter that lead to the simultaneous increase or decrease of all fragment abundances.

In laser-induced decomposition experiments, it is most often the intensity of the laser pulse that, by exhibiting pulse-to-pulse instability, causes fragments born in completely different decomposition processes to show positive covariance simply because each such process is highly intensity-dependent. A solution to such physical situations is provided by the partial covariance (pCov) mapping technique, where the universal correlations of all fragments to a single measured parameter, I, are mathematically removed:

$$p\ Cov(X,Y;I)=Cov(X,Y)-Cov(X,I)Cov(Y,I)/Cov(I,I) \quad (2)$$

where Cov(I,I) is the variance of the fluctuating parameter.

The present inventors have found that the application of methods of partial covariance mapping may be used to deduce a structure of analysed compounds. In the embodiments described below, all synthetic peptide samples were protonated in a solution of 50% acetonitrile/2% formic acid and directly infused into the mass spectrometer.

All measurements were performed with a LTQ XL (Thermo Scientific) linear ion trap mass spectrometer, with peptide ions infused via a nano-electrospray ion source (Thermo Scientific) at a flow rate of 3-5 µl/min. The temperature of the desolvation ion transfer capillary was held constant at 200° C. The peptide ion of interest was isolated in the linear ion trap and fragmented by collisional induced dissociation at normalised collision energy of either 20% or 35%, activation time of 30 ms and Mathieu q-value of 0.25.

1D spectra peak picking was performed by the vendor software, with further deisotoping and conversion to the Mascot general format (mgf) done using the open source ProteoWizard MSConvert software. The parent ion m/z was manually adjusted to mimic the performance of a high-resolution Orbitrap mass analyser.

For the analysis according to the present invention, software written in the Python language takes the raw data and performs all partial covariance, additional statistical and other required analysis. First, a partial covariance map of the data is calculated, using the total ion count across all m/z channels as a partial covariance parameter. Then those features on the map which may correspond to a true correlation are subjected to analysis of their statistical significance upon jackknife resampling. These features are ordered according to their calculated statistical significance, and further a priori filtering of the features according to the m/z of the parent ion is applied. Finally, this filtered set of features is converted to a peak list of individual mass-to-charge values.

Database searches were performed with a parent ion mass tolerance of 7 parts-per-million (ppm) and a fragment ion mass tolerance of 0.8 Daltons (Da). The searches were performed over the fully annotated SwissProt database, the fixed and variable modifications specified were sequence specific. There was no restriction given on the specificity of enzymatic cleavage. Mascot Server (Matrix Science) and the open source MS-Tag (Protein Prospector) database searching software were utilised.

In one embodiment, the invention provides for a method of applying partial covariance mapping technique to mass spectrometric data, producing two-dimensional mass spectra. This offers a range of advantages over the traditional one-dimensional MS in the structural analysis of proteins by collision-induced dissociation. The method provides an analytical application of the partial covariance mapping concept, providing a covariance mapping principle for species as large as peptides with molecular masses of the order of kDa. The method may be performed using industry standard mass spectrometry benchtop instrumentation enabling immediate utilisation as a practical tool.

This embodiment is exemplified by an analysis of a peptide that produces abundant structure confirming fragment ions. The inventors performed ESI-MS measurements on the Histone H3 peptide VTIMPKDIQLAR, choosing its triply protonated ion $[M+3H]^{3+}$ for collision induced dissociation (CID) fragmentation.

Figure 1B:
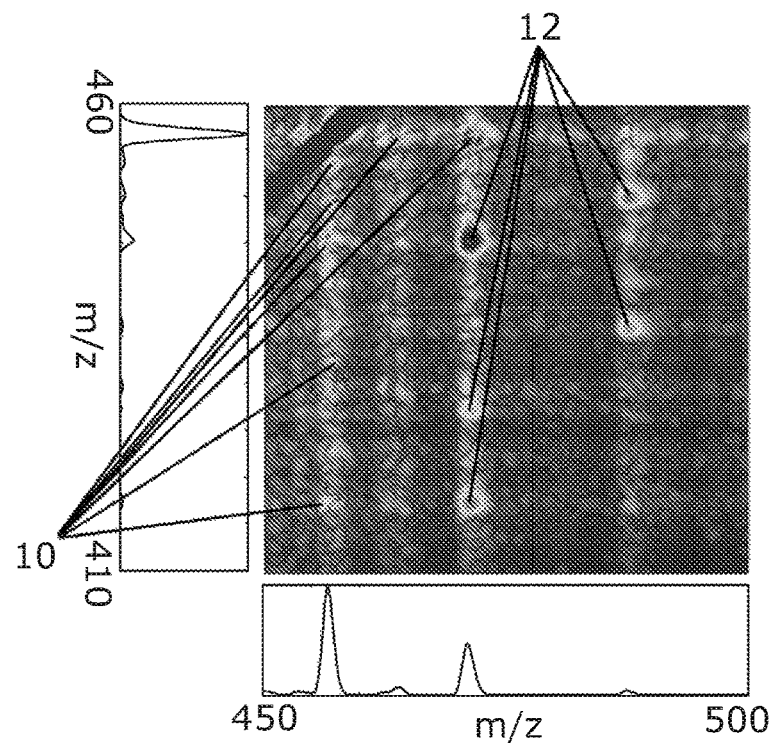
FIG. 1(b) shows a region in the simple 2D covariance map of the same peptide showing both true (intrinsic, shaded region 12) and false (extrinsic, shaded region 10) correlations.

FIG. 1a shows the conventional 1D CID mass spectrum of $[VTIMPKDIQLAR+3H1]^{3+}$ ion with abundant peaks of so-called b-type and y-type ions, comprising the N-terminus and C-terminus of the peptide, respectively, and resulting from cleavages along the peptide backbone, e.g. [VTIMPKDIQLAR+3H]3+→$y_8^{2+}$+$b_4^+$. A 2D covariance map can be built for this ion using Eq. (1), where index i corresponds to one microscan of the linear ion trap. As expected, however this map exhibits so-called spurious or extrinsic peaks corresponding to correlations between any arbitrary pair of fragments (see FIG. 1b). Without wishing to be bound by any particular theory, it is postulated that this is due to the scan-to-scan fluctuations of a number of experimental parameters affecting the abundance of every fragment ion: helium pressure in the ion trap, spray quality, ion focusing and ion trap voltages, etc.

In a standard MS experiment, none of these parameters are monitored on a scan-to-scan basis and some of them are even unknown, such that a direct application of the partial covariance formula (2) to suppress the spurious correlations seems to be impossible. Nevertheless, the invention provides a simple solution to this difficulty: since the fluctuations in experimental conditions lead eventually to fluctuations in the total number of fragment ions detected at each scan comprising one microscan and the latter is well-characterised in a standard MS measurement, we take a sum of the integrals across each m/z channel, correlating to the total ion current of the spectrum, as a single fluctuating parameter, I, to be used for partial covariance mapping, see Eq. (2). In this embodiment the total number of fragment ions detected is used as an internal standard to allow shot-to-shot normalisation of the data and thereby remove extrinsic fluctuations that would otherwise appear as strong correlations, which would in turn mask the correlations due to the fragmentation itself.

Figure 1C:
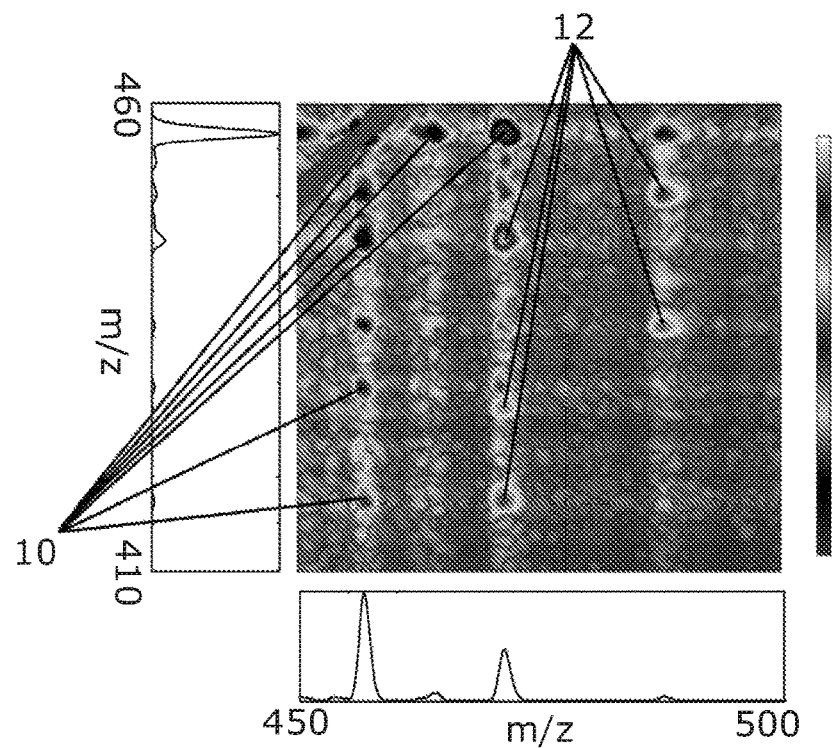
FIG. 1(c) shows the same region as FIG. 1(b) but of the 2D partial covariance map, revealing full suppression of the false (extrinsic, shaded region 14) correlations and survival of all the true (intrinsic, shaded region 12) correlations.
Figure 1D:
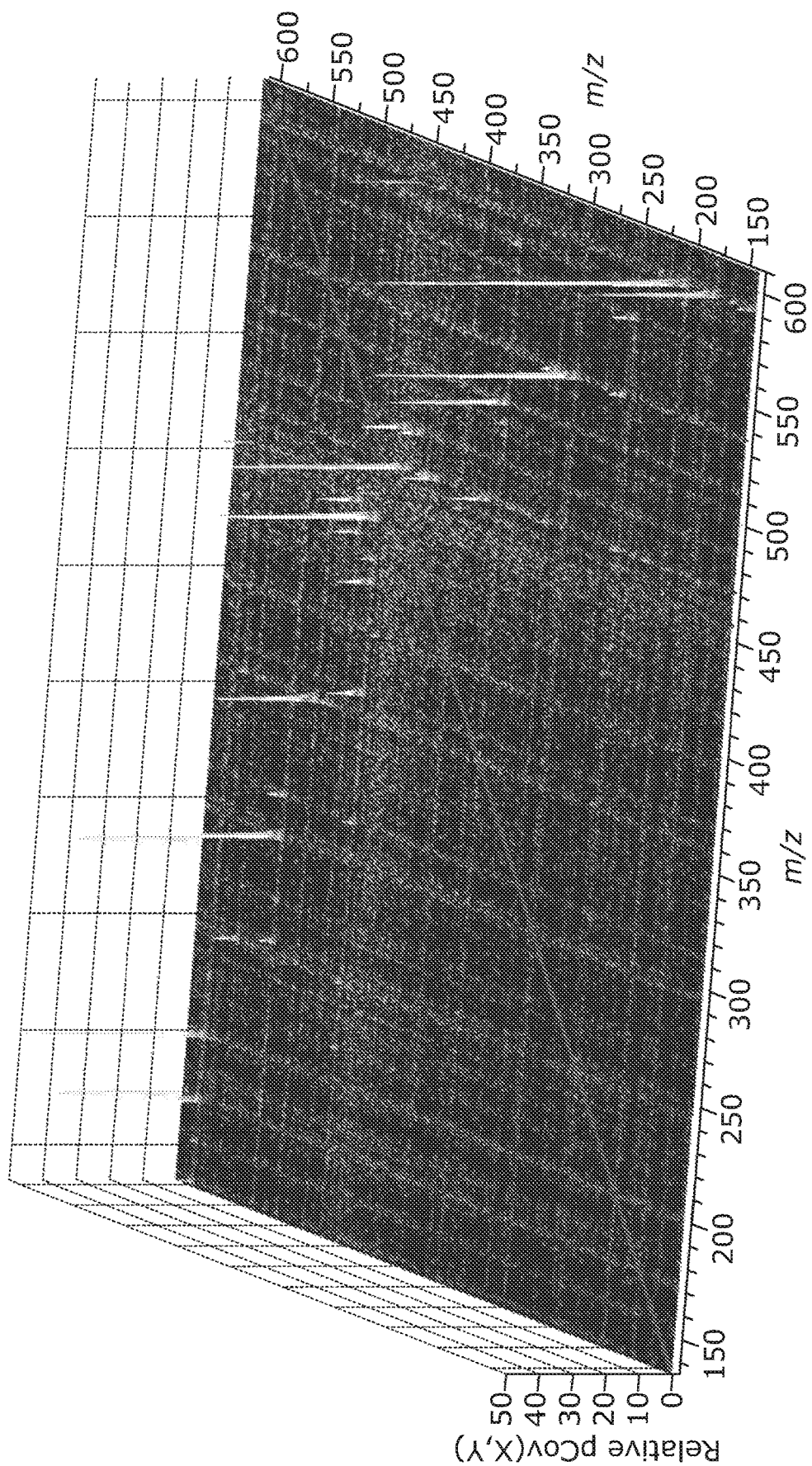
FIG. 1(d) shows a 3D view of the m/z 135-m/z 610 region of the partial covariance map of [VTIMPKDIQLAR+3H]$^{3+}$ in which the overwhelming majority of the peptide fragment ion correlations are observed. In (b-d) the autocorrelation line signals have been removed for clarity)
Figure 2A:
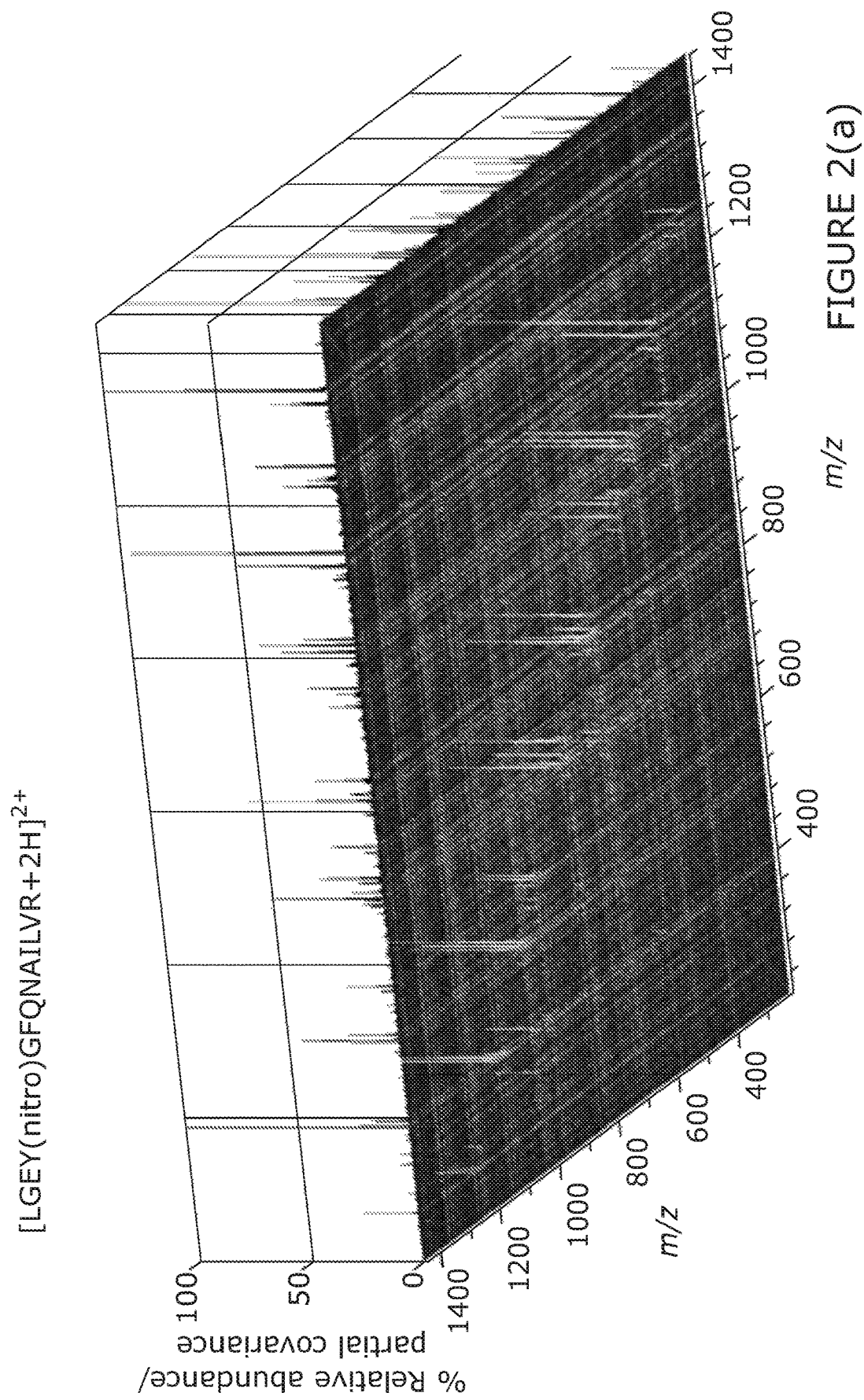
FIGS. 2 to 11 show (a) partial covariance maps of fragmentation of various peptide ions and (b) scatter plots showing the relative abundance and relative significance calculated according to embodiments of the present invention for those fragment ions of those peptide ions.
Figure 2B:
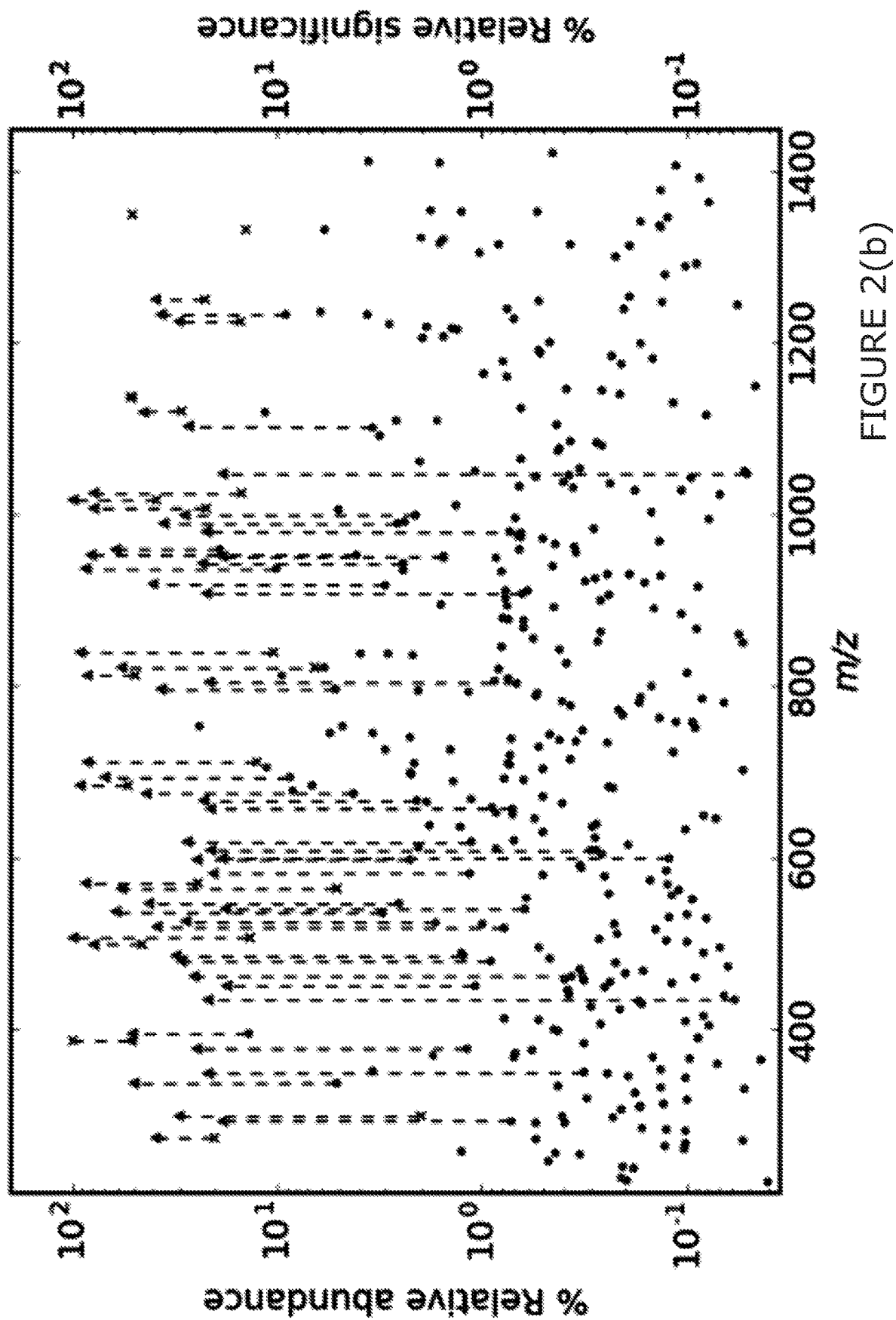
Figure 3A:
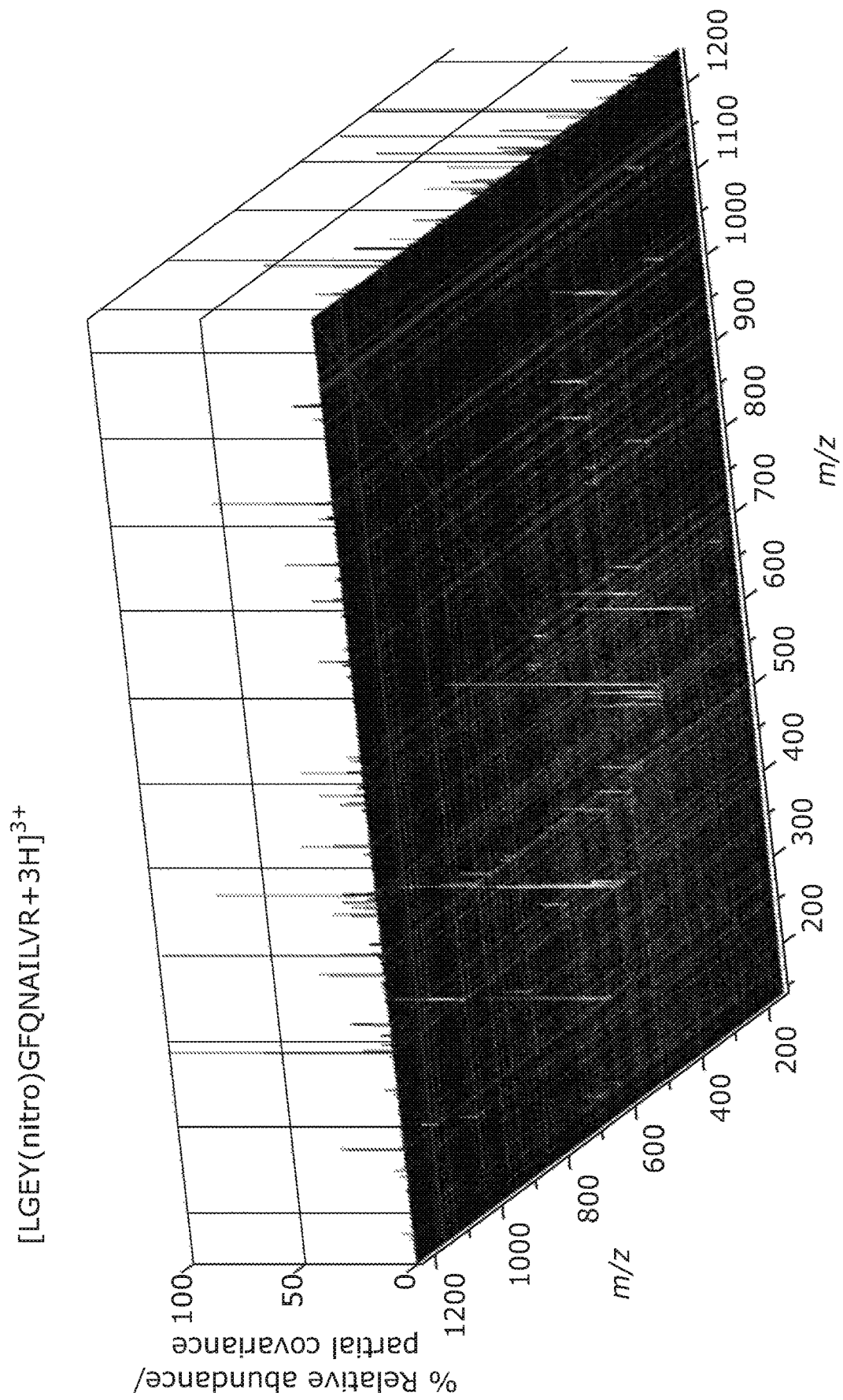
Figure 3B:
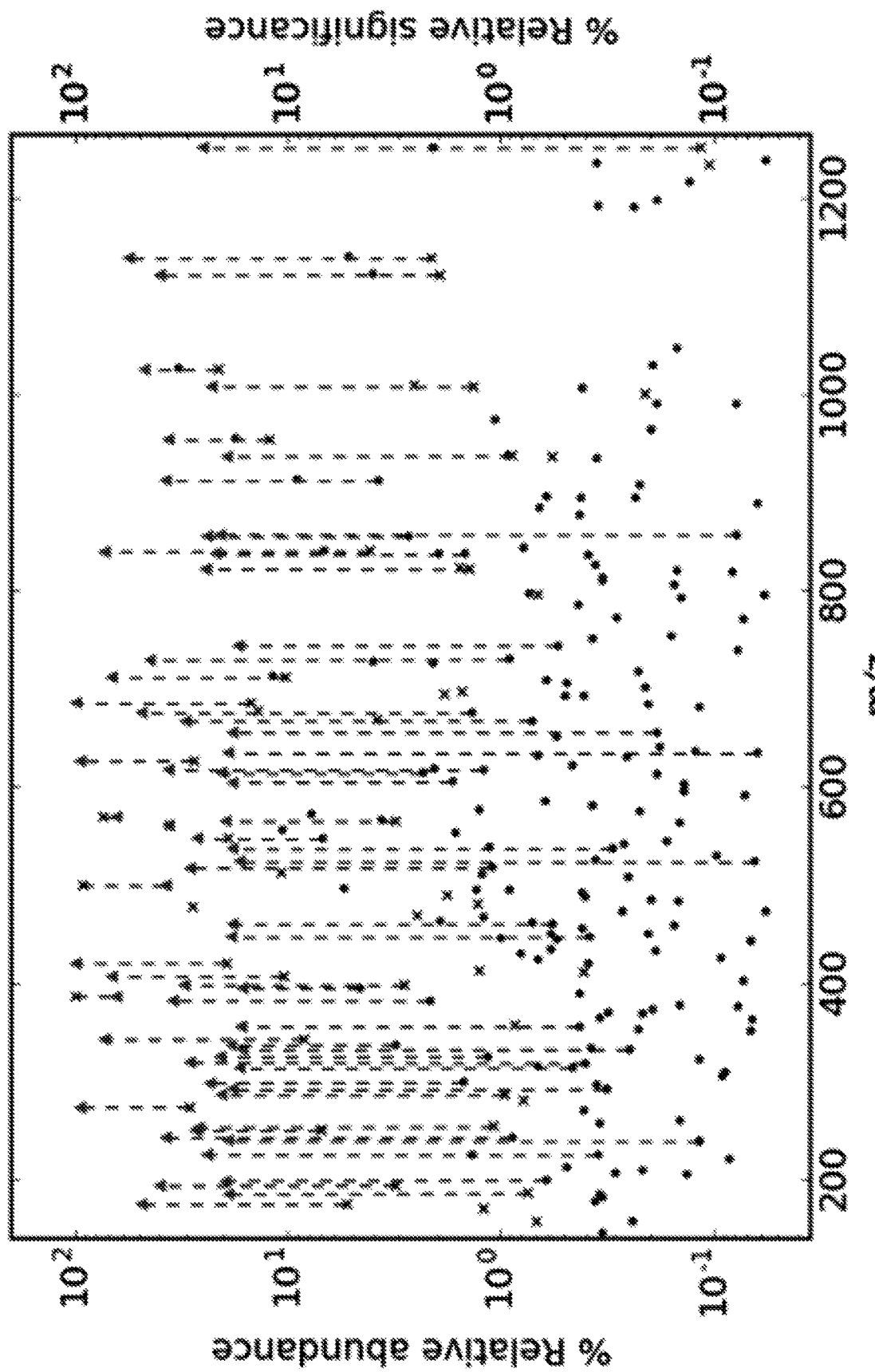
Figure 4A:
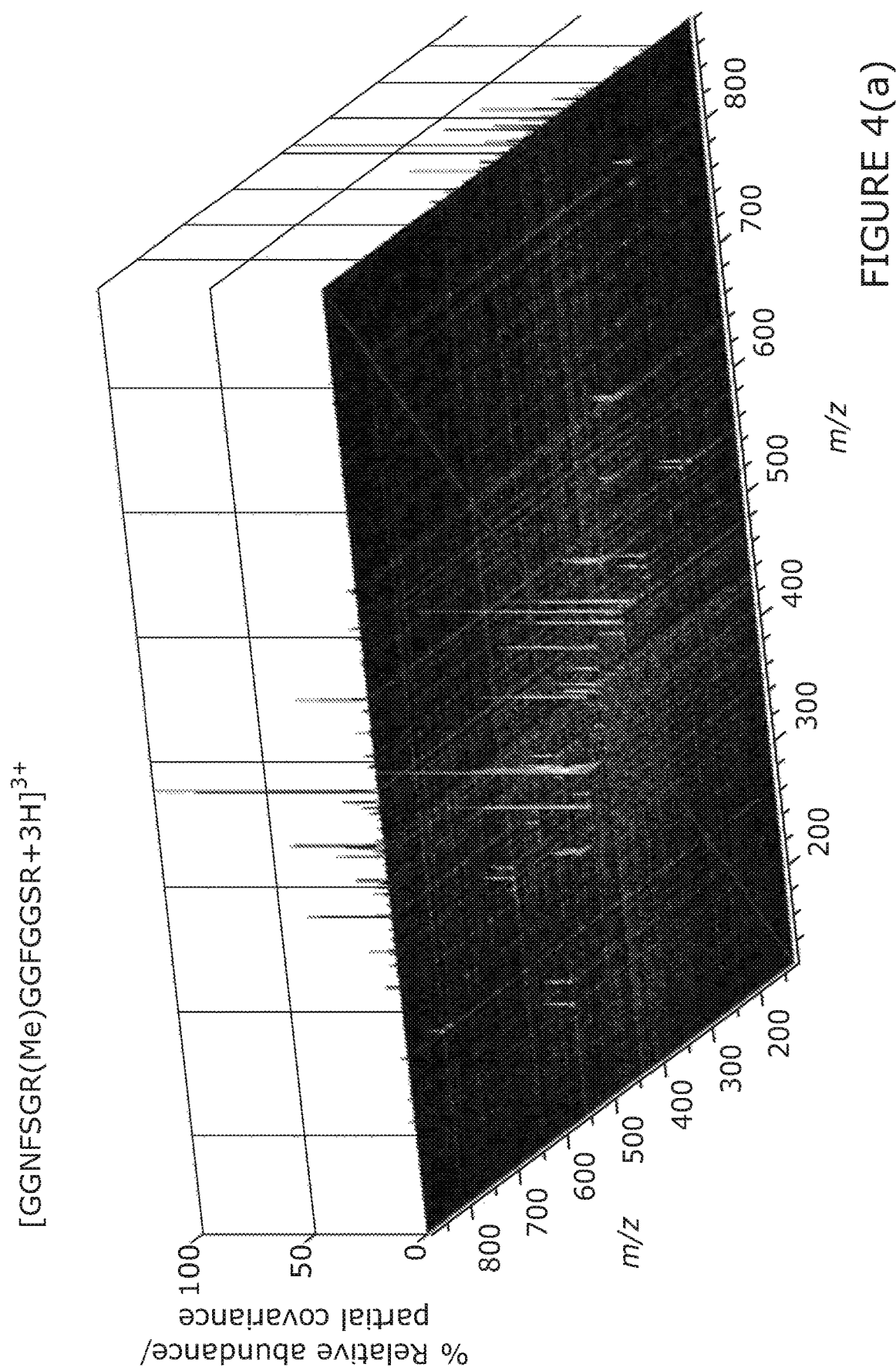
Figure 4B:
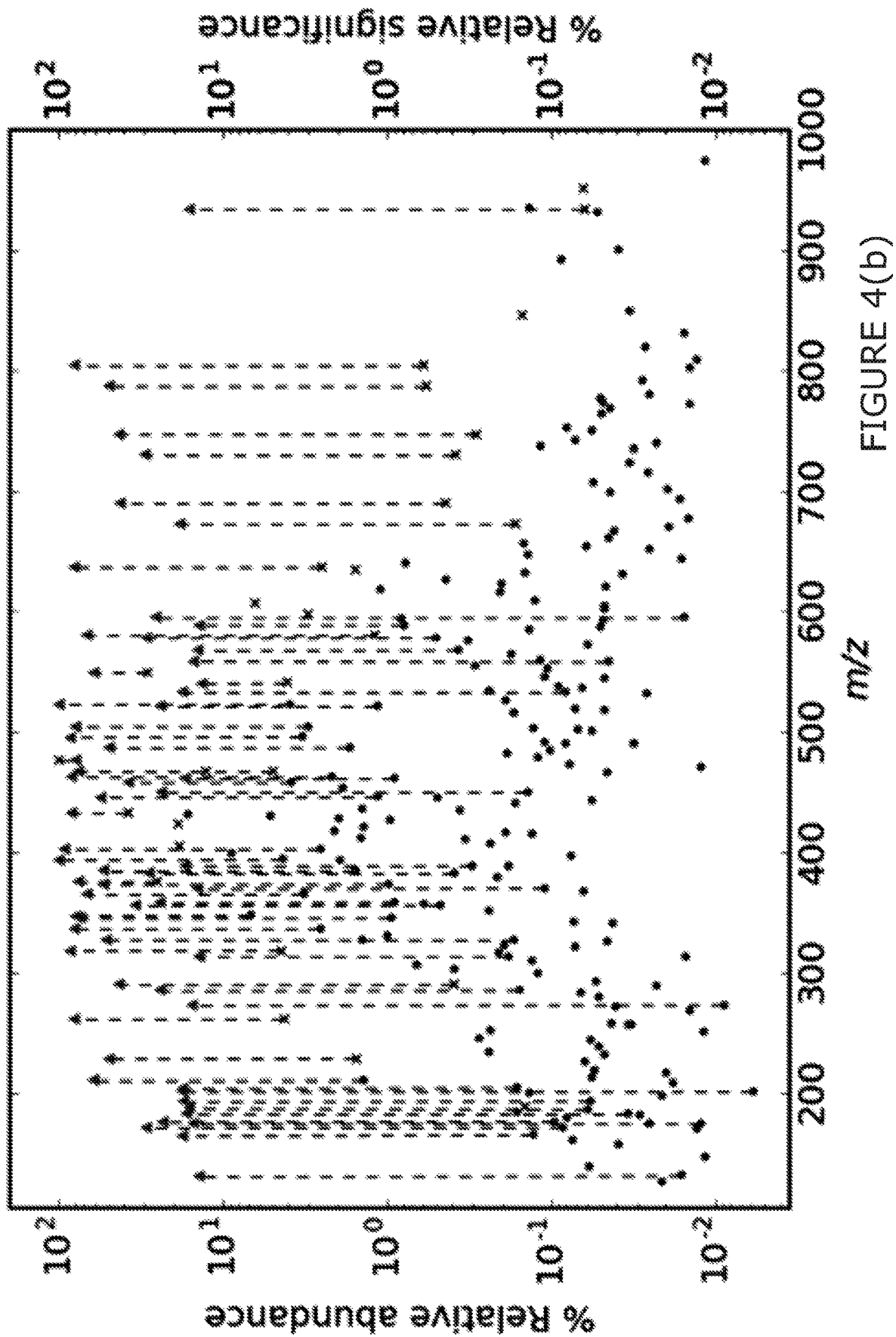
Figure 5B:
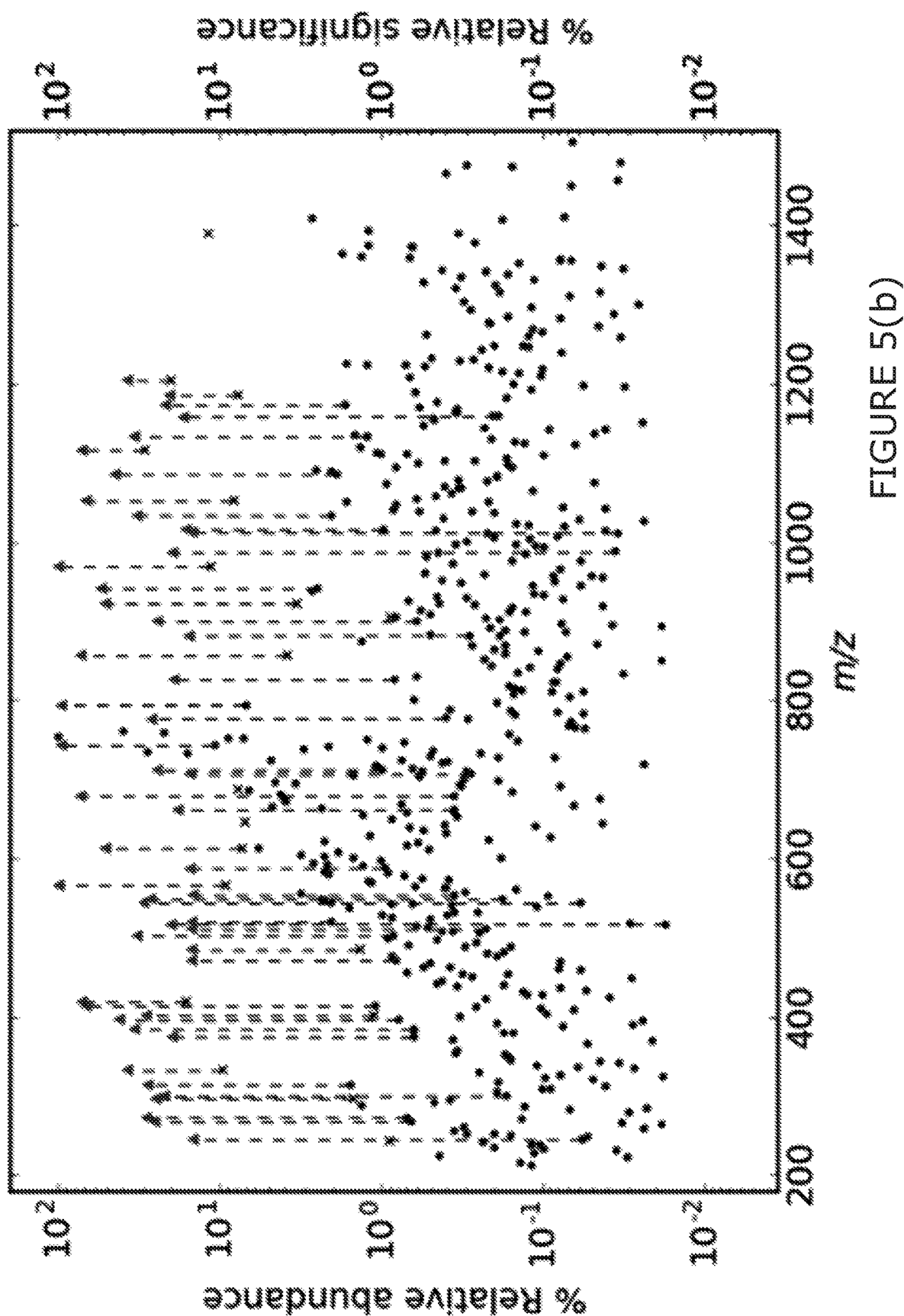
Figure 6A:
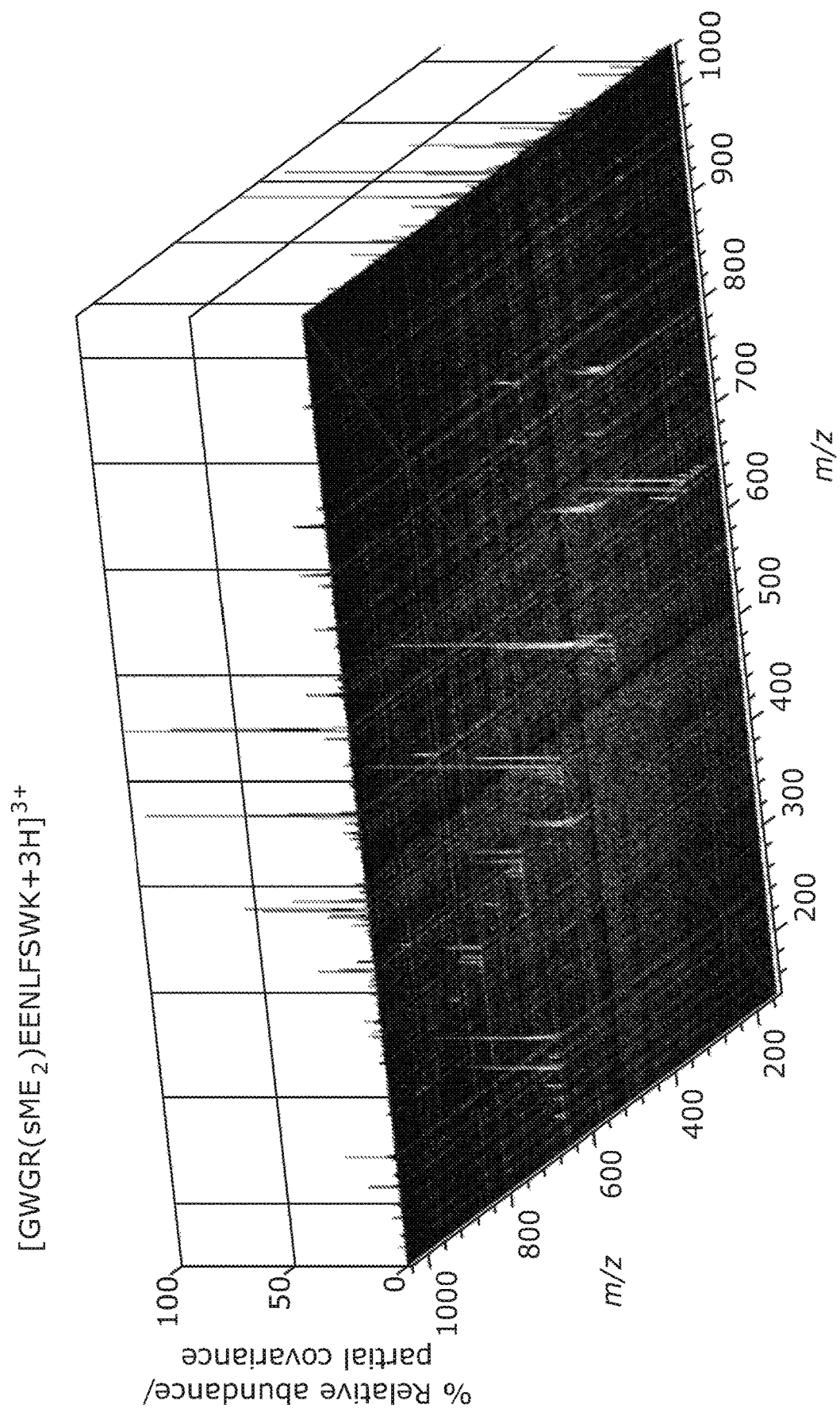
Figure 6B:
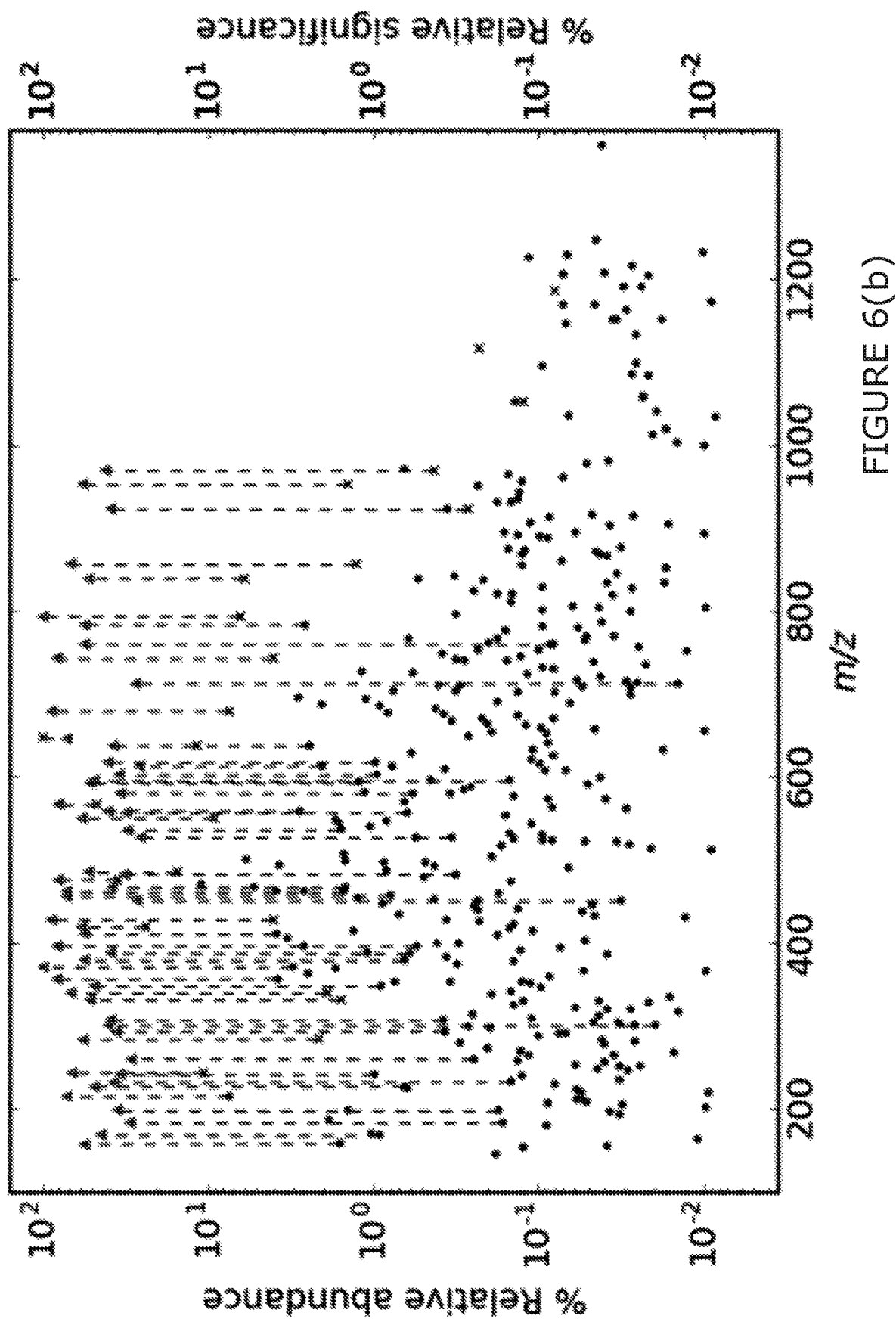
Figure 7A:
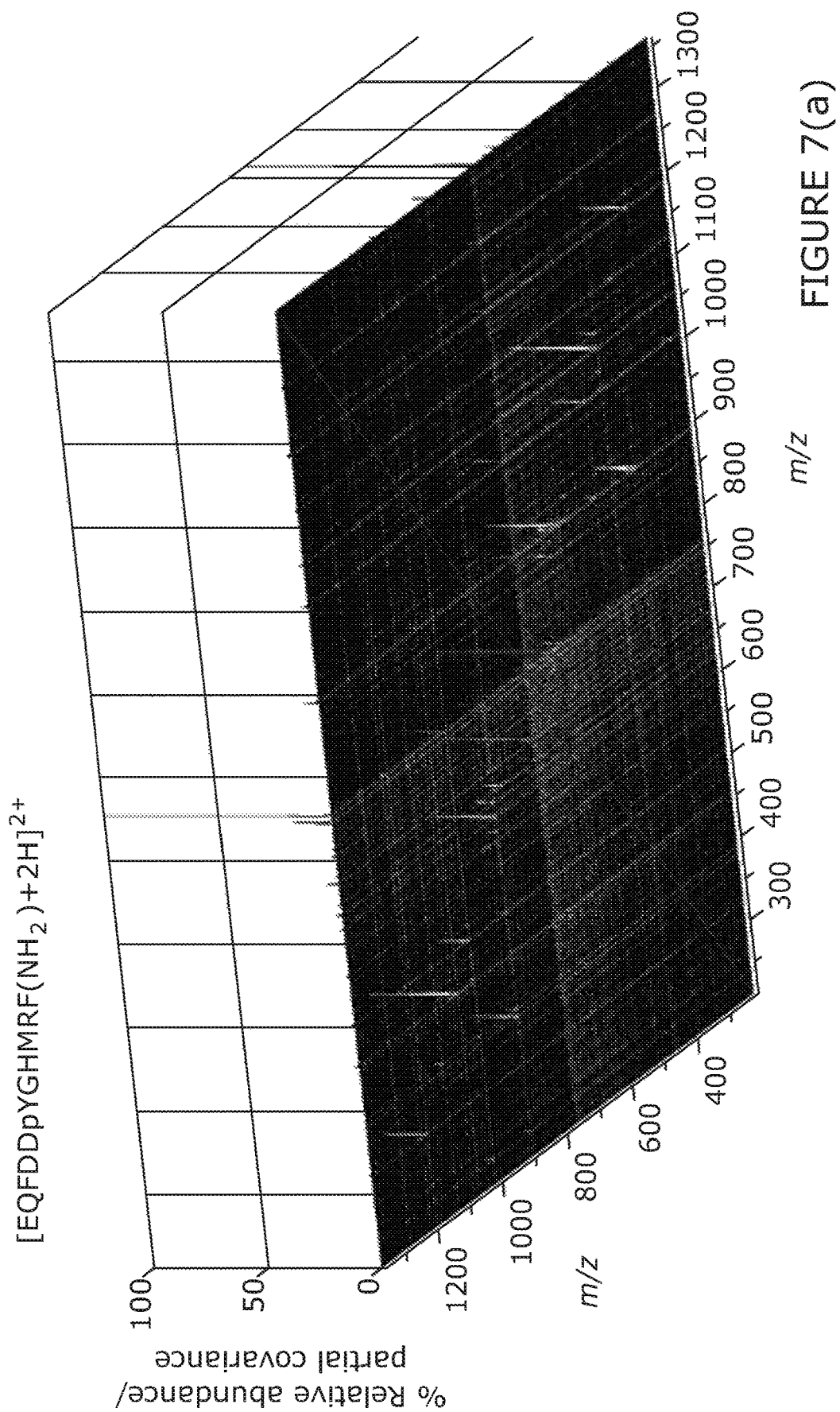
Figure 7B:
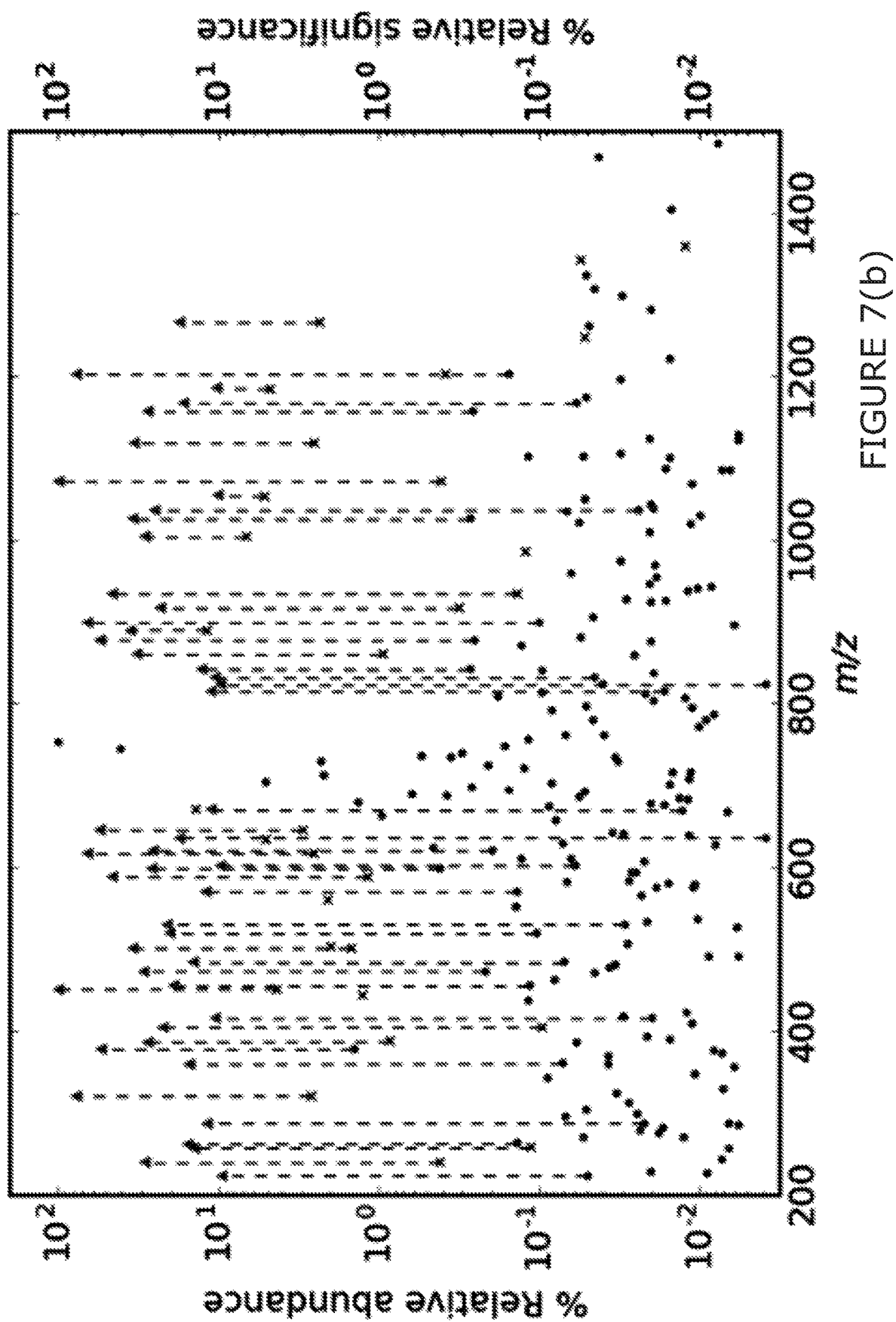
Figure 8A:
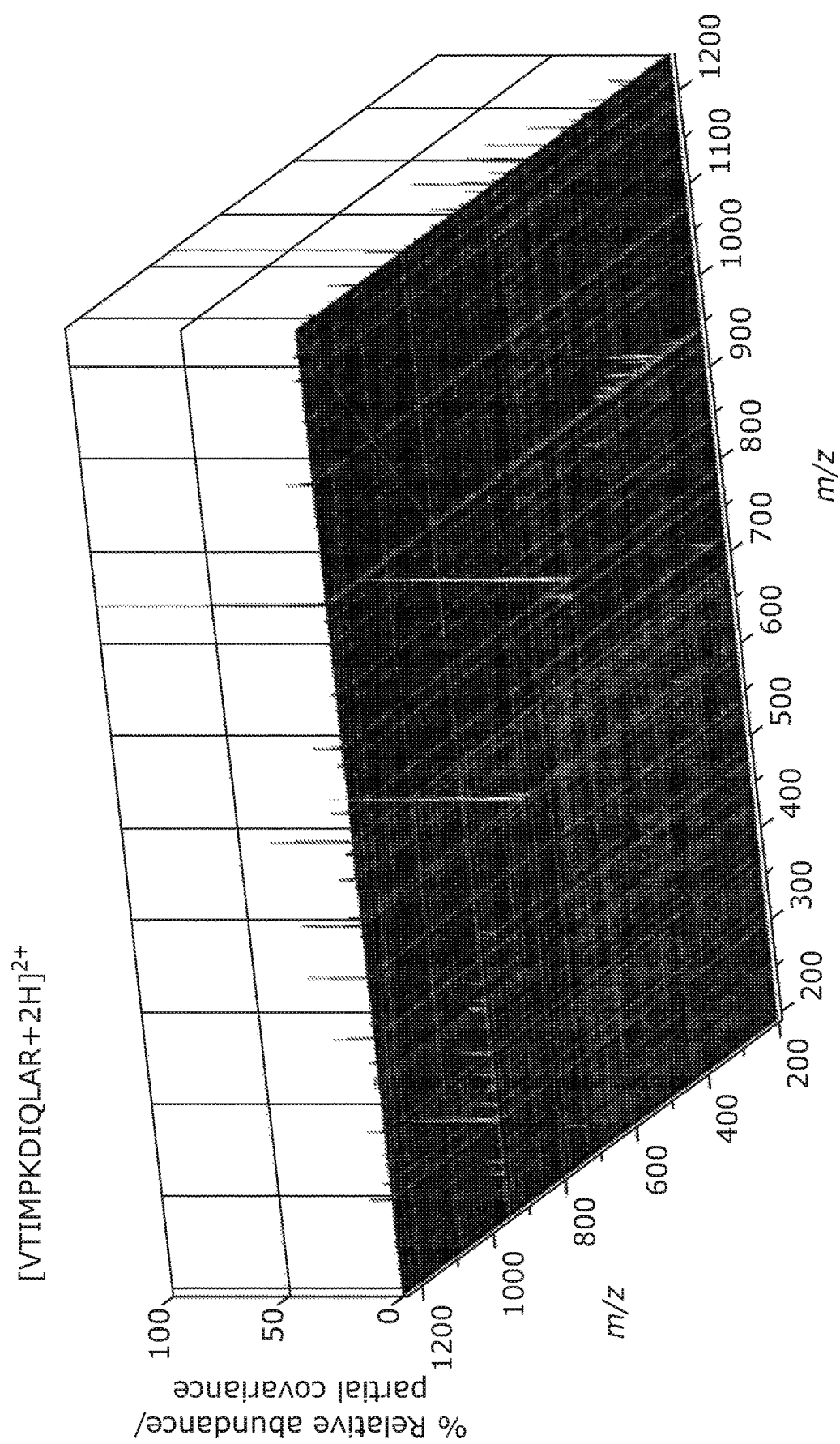
Figure 8B:
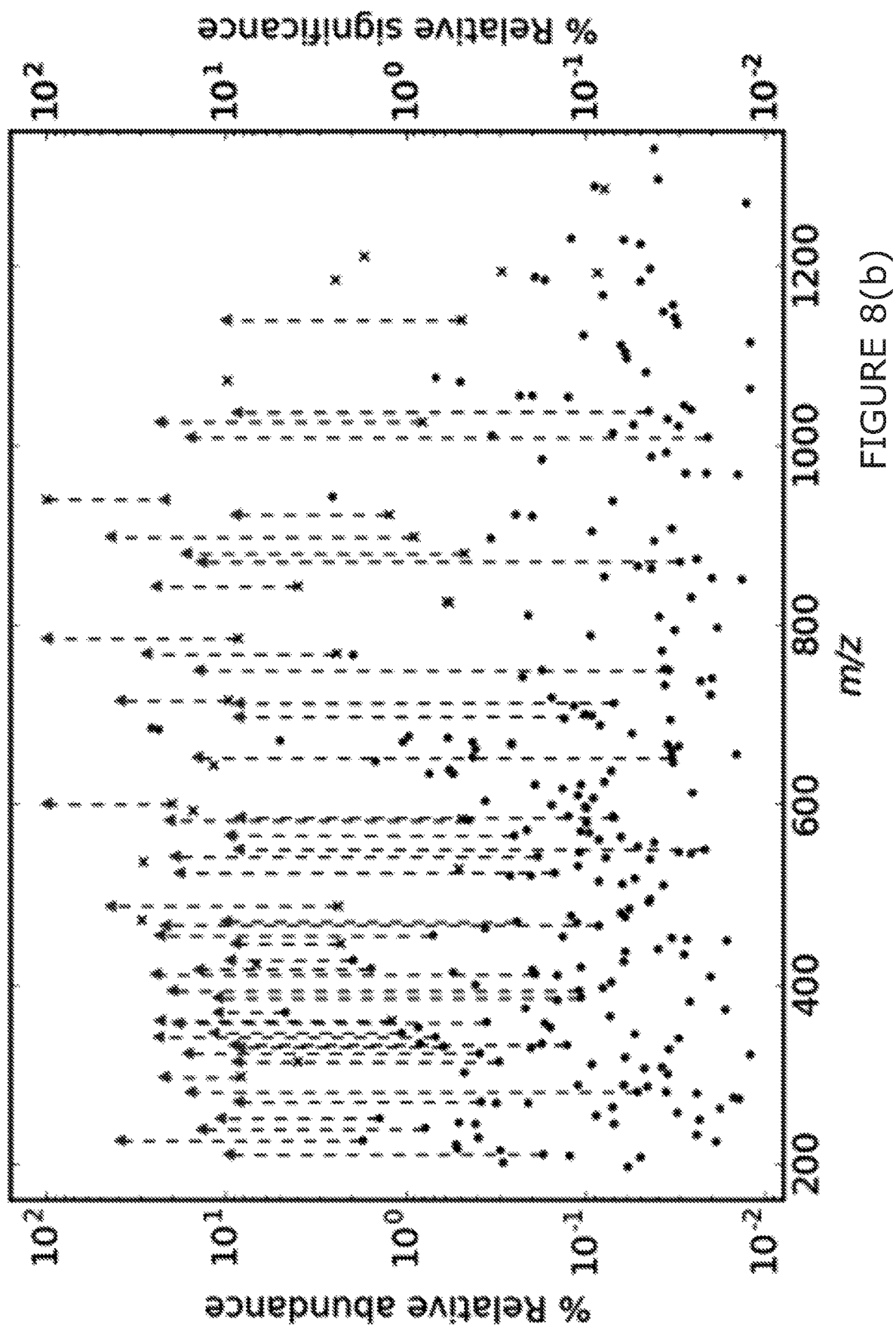
Figure 9A:
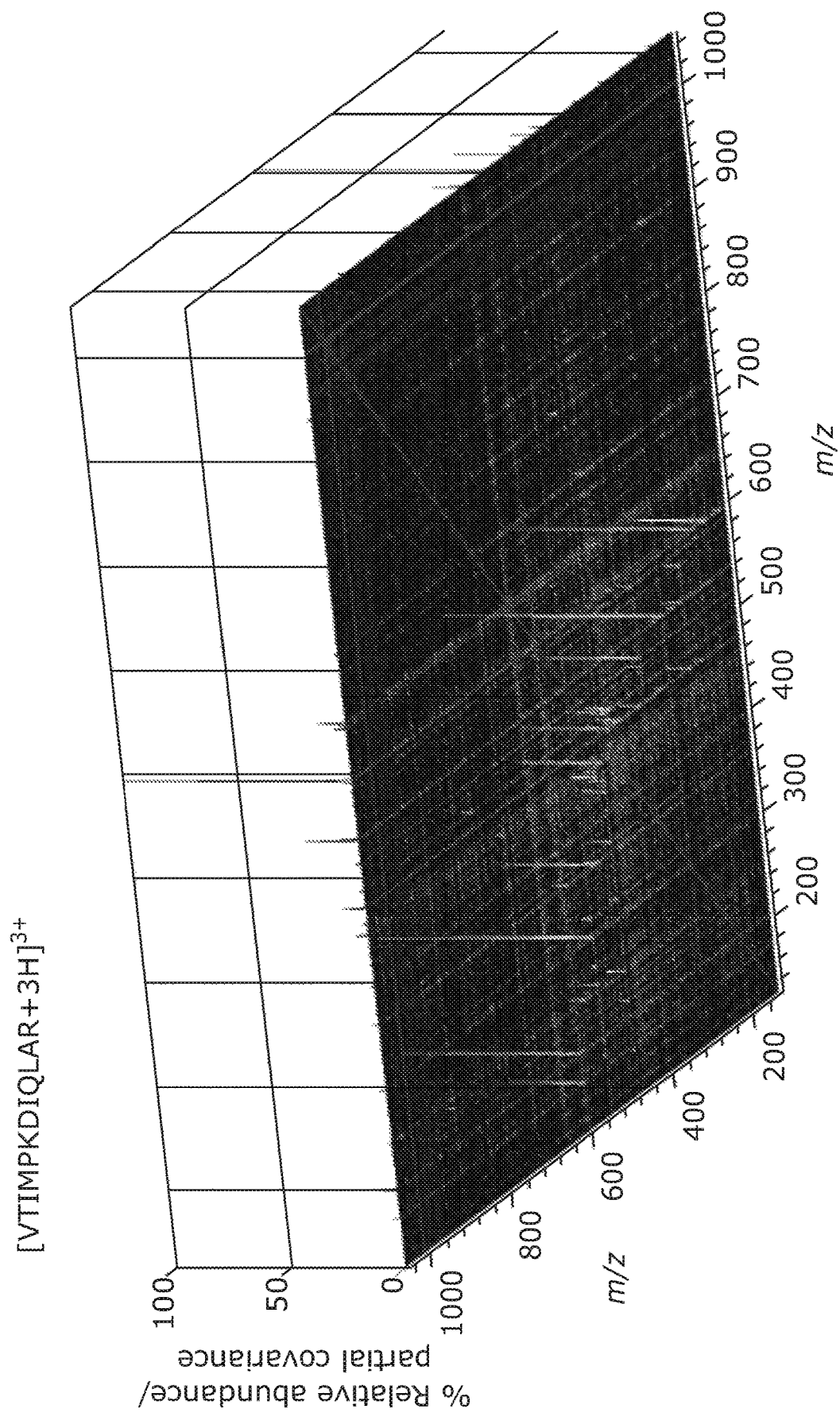
Figure 9B:
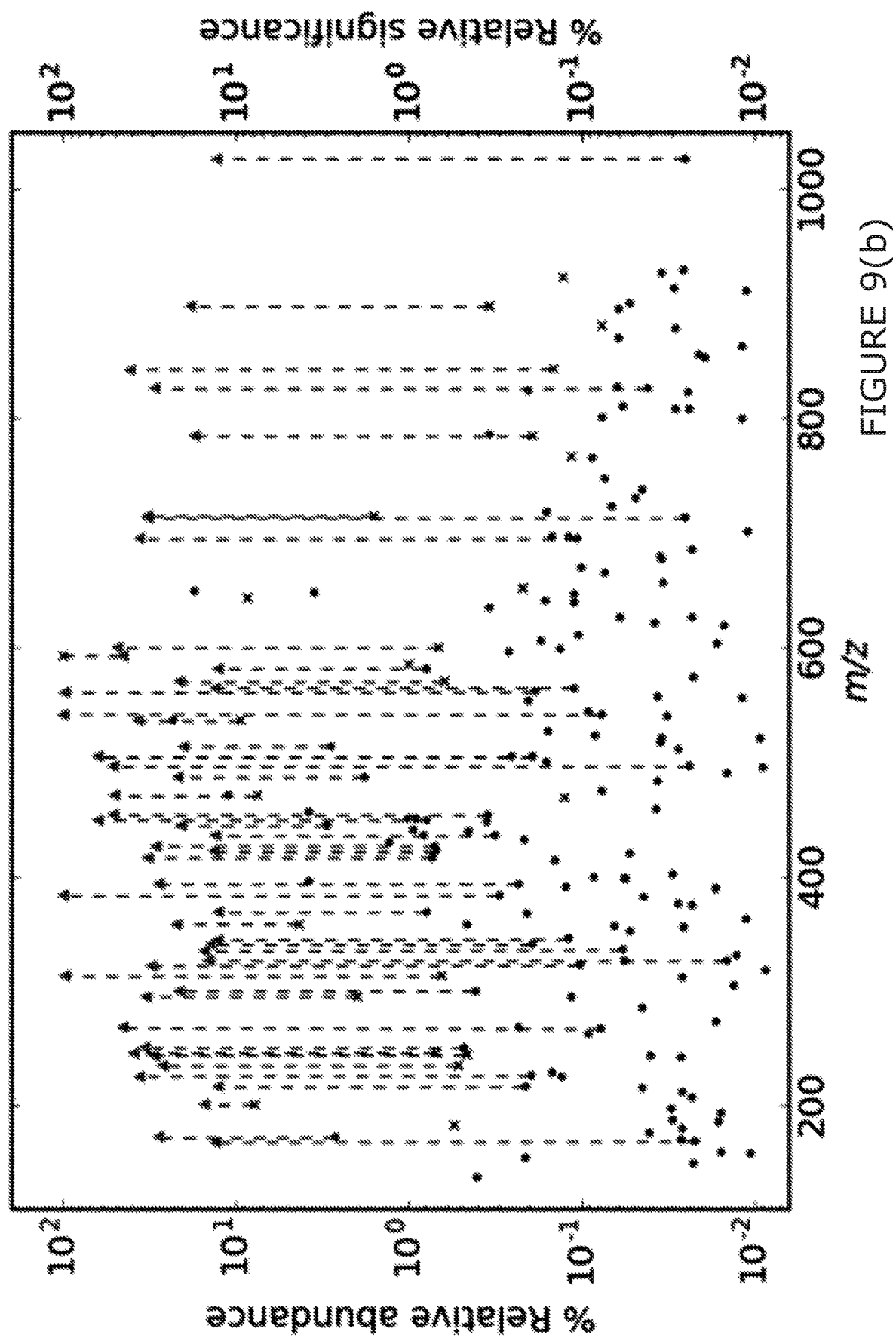
Figure 10A:
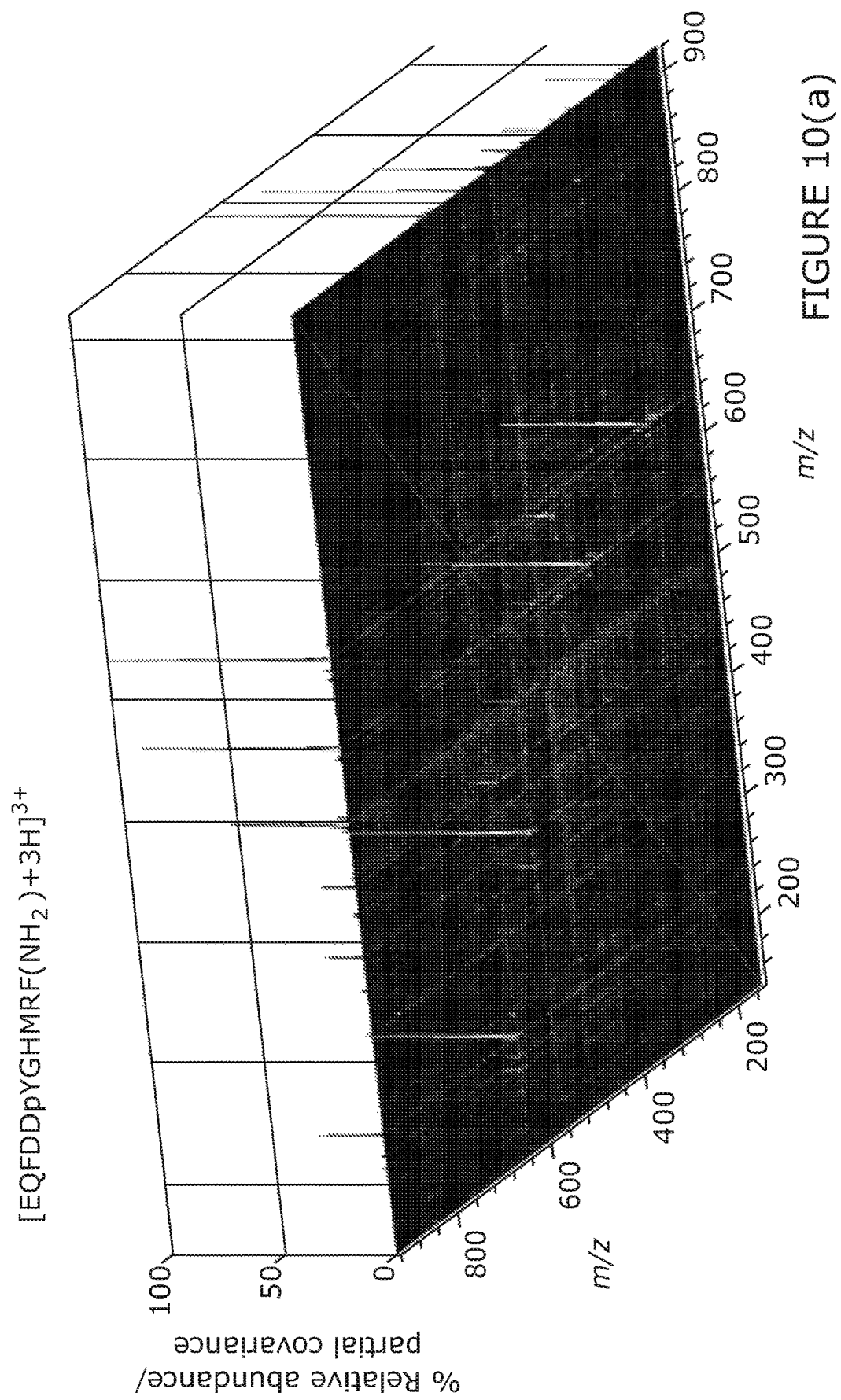
Figure 10B:
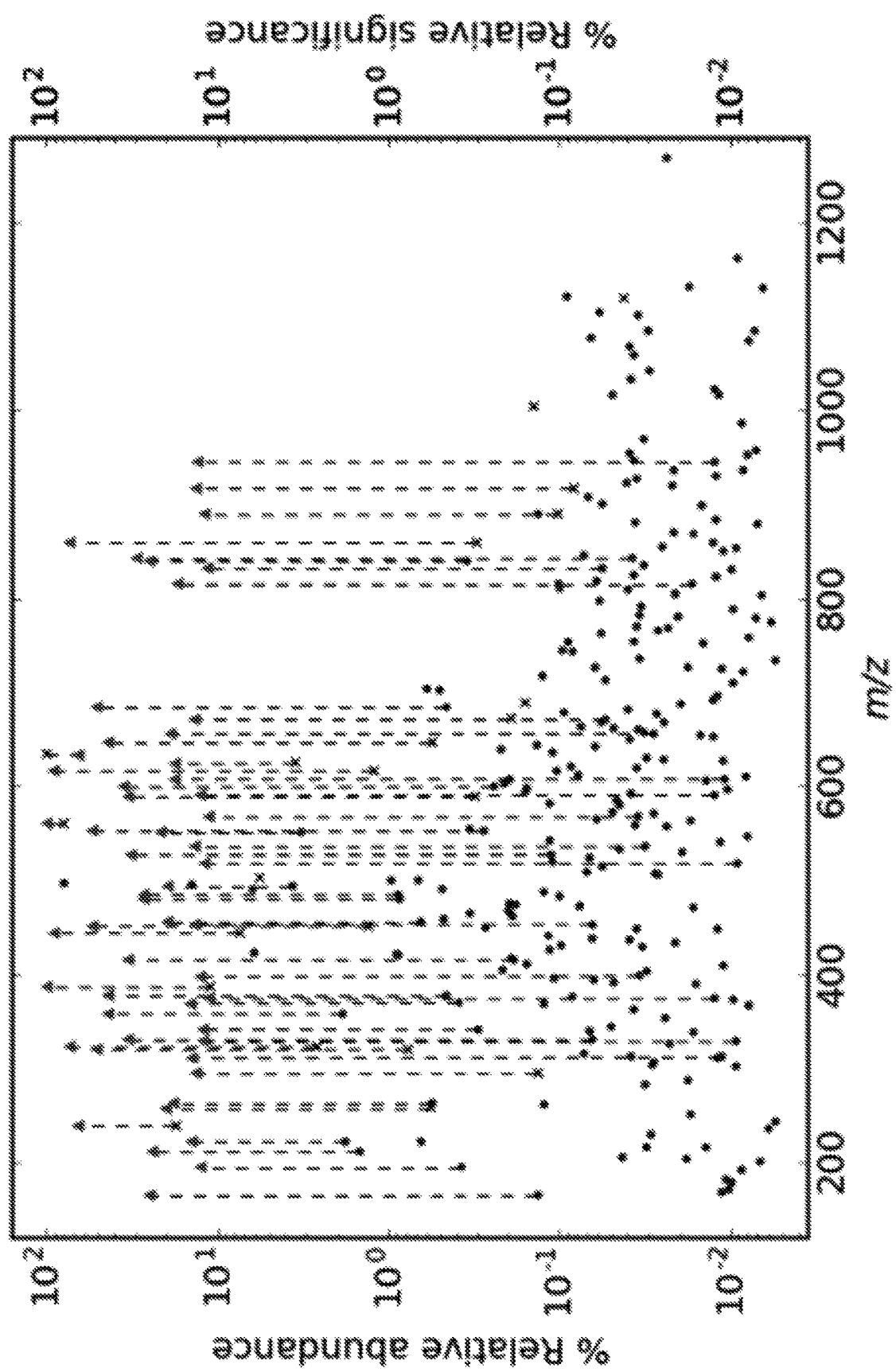
Figure 11A:
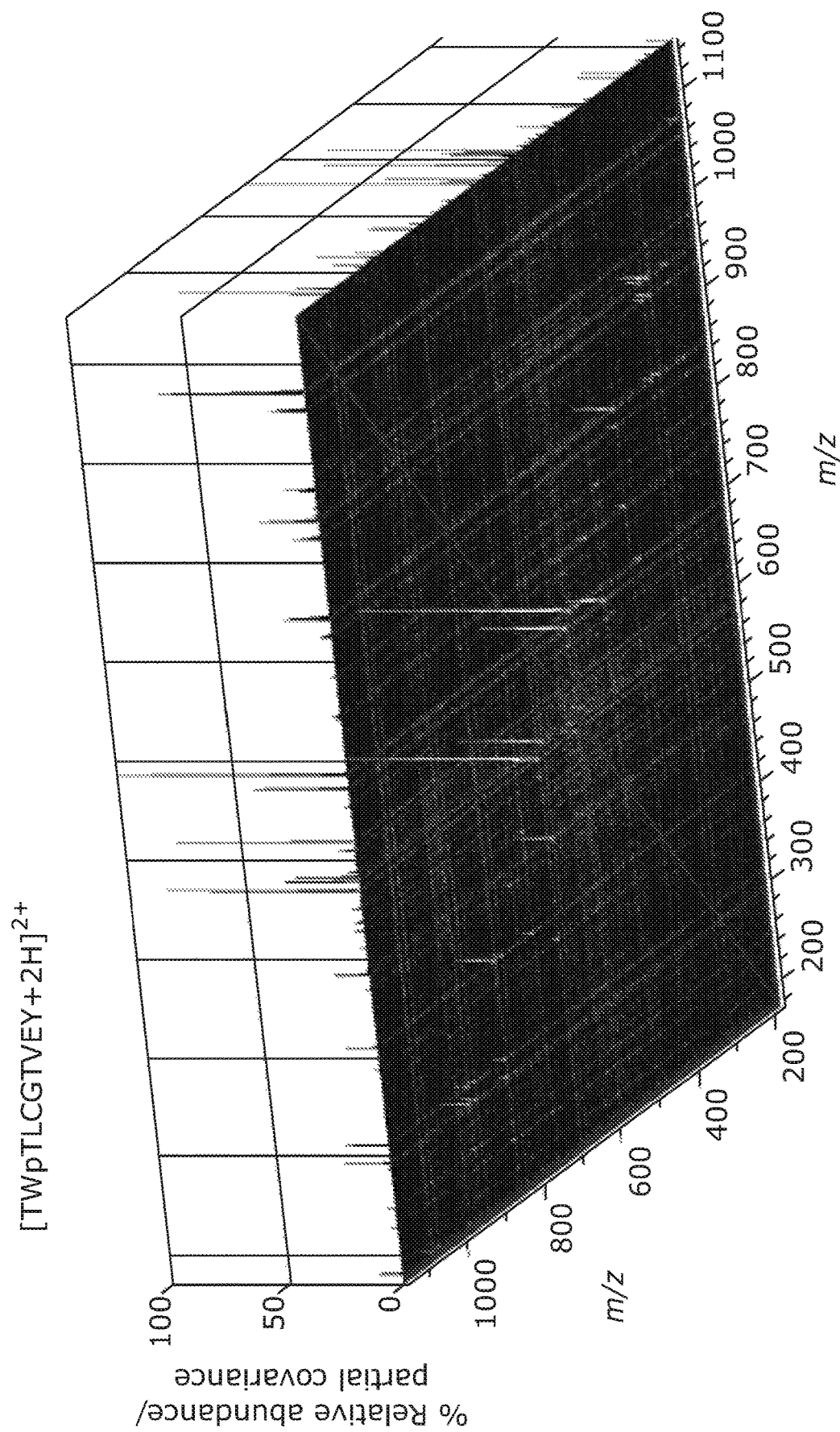
Figure 11B:
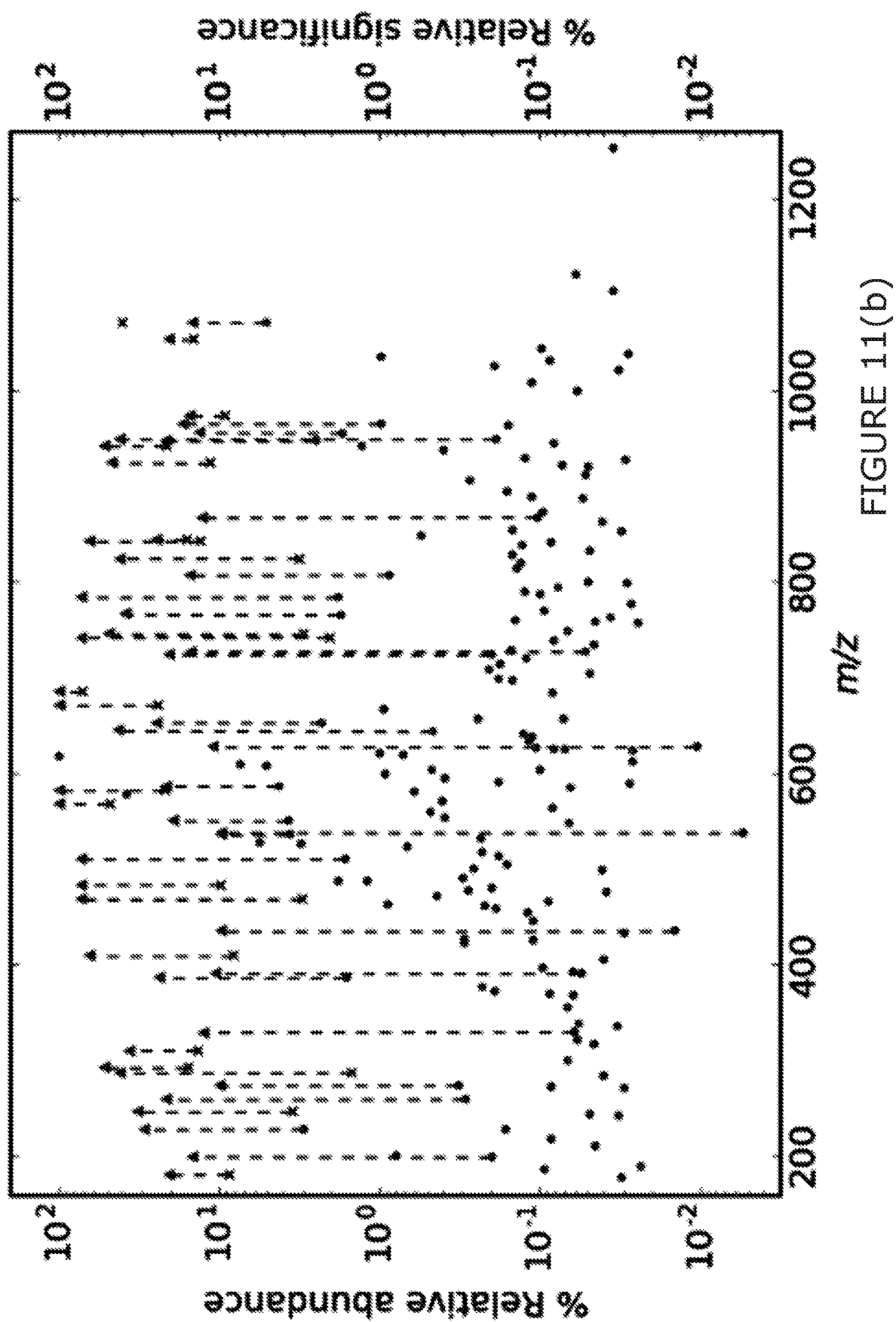

Application of the partial covariance formula (2) leads to the result shown in FIG. 1c: all the extrinsically induced (false) correlations become suppressed (shaded regions 10 in (b) become shaded regions 14 in (c)) and a series of peaks reflecting the expected connectivity between corresponding y- and b-type ions and their consecutive decomposition products (neutral losses and further backbone ruptures of the peptide), are revealed as sharp features in the partial covariance spectrum. While the complementary b-ion/y-ion correlations of the peptide are arranged along one of the two mass-conservation lines (each corresponding to a specific charge partition between y- and b-type ion series) of the peptide, consecutive decomposition fragments lead to the formation of horizontal and vertical peak series relatively to each main peak enabling a rapid assignment of both the primary and secondary fragments of the peptide. This demonstrates that the detection efficiency of the linear ion trap system is high enough to enable the application of the partial covariance technique to trapped peptide ions, while showing that the scan-to-scan change in the total ion current is a confident measure of the significant fluctuations in numerous experimental parameters.

To confirm these conclusions, we have successfully tested the validity of the proposed partial covariance mapping on a representative sample of peptide ions including unmodified structures and peptide sequences bearing various PTMs (phosphorylation, sulphation, nitration, methylation), the data being shown in FIGS. 2-11.

Each of FIGS. 2 to 11 shows a 3D plot of partial covariance map and illustration of multiple order of magnitude enhancement of signal intensity for structurally informative peaks using the partial covariance-based two-dimensional mass spectrometry of the present invention.

In each, part (a) shows a partial covariance map of the fragmentation of the relevant parent peptide molecule upon collisional-induced dissociation. The plot is of the partial covariance map with total ion count as the partial covariance parameter. The m/z values of the correlated peaks are plotted along the x- and y-axes whilst the surface represents the partial covariance function values, normalised to the highest peak on the partial covariance map. The autocorrelation line, which trivially correlates each peak to itself, has been manually cut from each map along a width of 5.67 Da. The line graph plotted against the back walls of the partial covariance map is the 1D mass spectrum.

In each part b), there is shown an illustration of the enhancement of structural signals using the method of the present invention. Crosses represent relative abundances of those peptide sequence informative peaks in the 1D spectrum which were identified by the automatic database search engine. Triangles represent those peaks identified as structurally informative by the method of the invention, represented by their calculated relative significance. Diamonds represent signals were not assigned to an expected peptide fragmentation. It should be noted that relative abundance and relative significance values are plotted on the same logarithmic scale to illustrate the relative amplification of multiple structural signals by several orders of magnitude in the data subjected to the analysis of the invention. Circles represent those peaks in the 1D spectra which could not be identified by the automatic database search engine as structurally informative sequence ions. Dashed lines connect the relative significance signals identified as structurally significant to the corresponding relative abundance signals in the 1D mass spectrum.

The example considered in relation to FIG. 1 shows the principle of the method of the invention using peptides with abundant sequence-specific fragmentation ions. The method of the invention has crucial advantages over the standard one dimensional approach, particularly where fragmentation signals are suppressed and/or their origin is poorly understood.

Figure 12A:
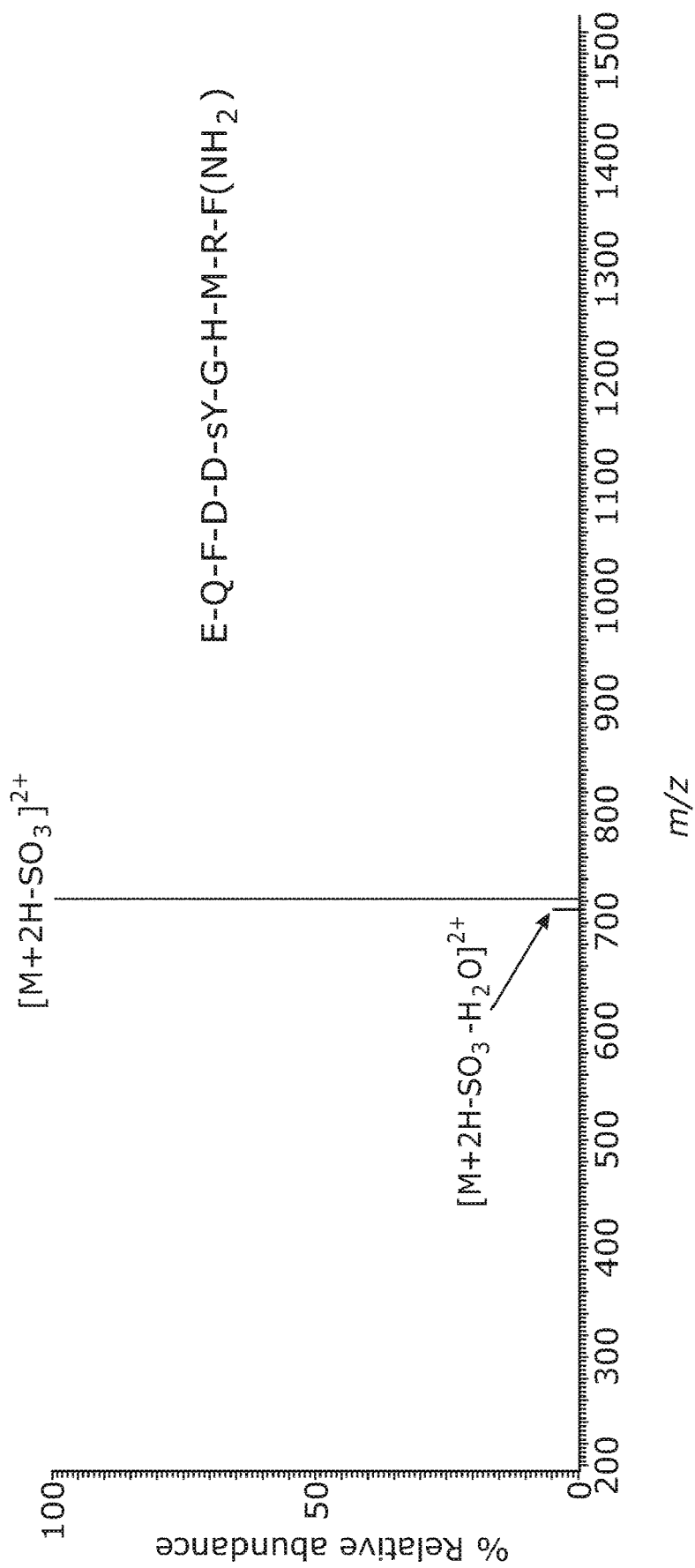
FIG. 12(a) shows a CID spectrum of the [EQFDDsYGHMRF(NH2)+2H]$^{2+}$ sulfopeptide showing prominent SO$_3$ neutral loss that causes a strong suppression of the peptide sequence-specific fragments, sY=sulfotyrosine.

As a further example, the CID spectrum of doubly protonated perisulfakinin sequence [EQFDDsYGHMRF(NH$_2$)+2H]$^{2+}$, which is dominated by neutral loss of sulphur trioxide with sequence specific peaks of y- and b-type ions being strongly suppressed, may be considered, see FIG. 12a. This is an example of a peptide ion that is either assigned an incorrect structure by standard automatic analysis tools or else is assigned the correct structure with low confidence, still leading to lack of identification.

Figure 12B:
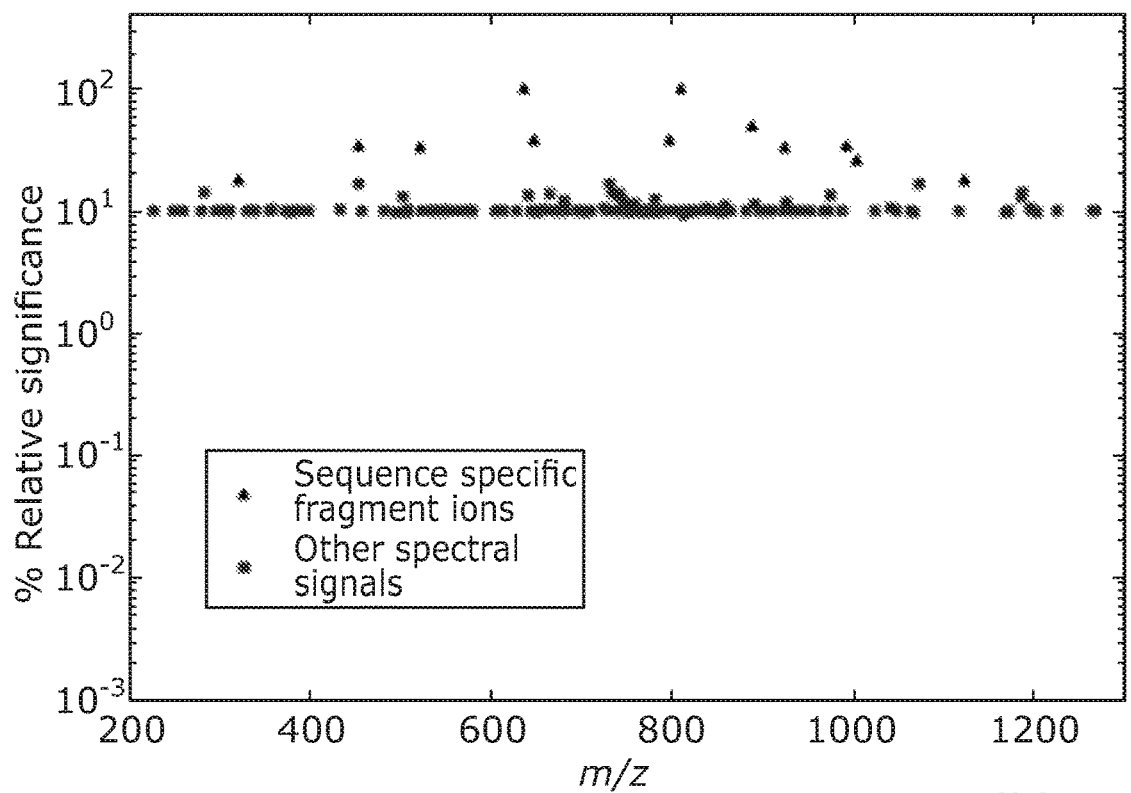
FIG. 12(b) shows a logarithmic plot of relative significances derived from the pC2DMS map according to Eq. (3), sequence specific fragment peaks are shown as triangles, other peaks are shown as squares, the two groups of peaks are well separated.
Figure 12C:
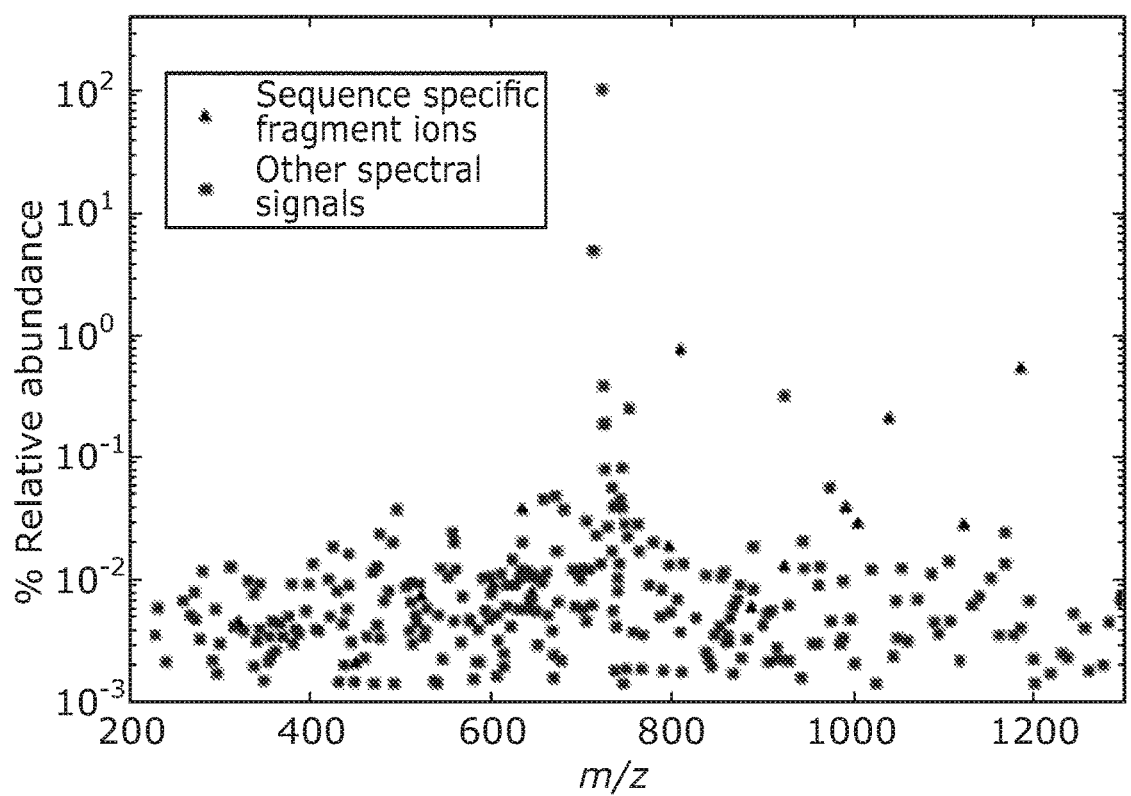
FIG. 12(c) shows a logarithmic plot of relative abundances in 1D spectrum of the [EQFDDsYGHMRF(NH2)+2H]$^{2+}$ ion showing that most of the structure-reporting peaks are at the noise level, i.e. mixed with the square peaks. The relative significances (FIG. 12b) of the structure-reporting peptide peaks are enhanced relatively to their relative abundances (FIG. 12c) by 2-4 orders of magnitude.
Figure 13:
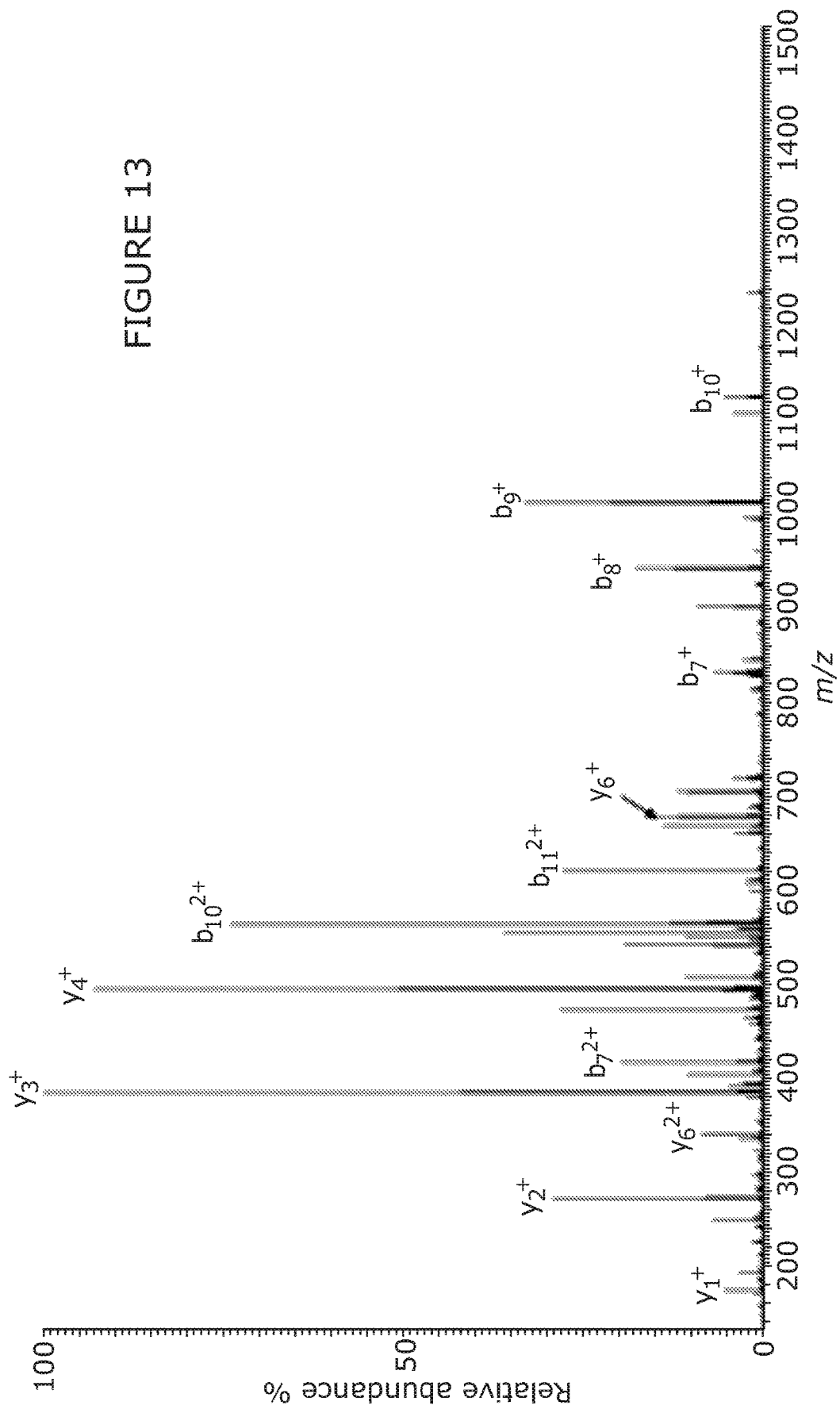
FIGS. 13-19 show the standard 1D MS/MS spectra of the model peptide ions with main signals annotated (the top centre panel); logarithmic plots of the results of the Mascot search performed on the standard 1D MS/MS data (left) and on the relative significance list of the pC2DMS (right), together with pie charts showing the enhancement of the pC2DMS relative significances relatively to the 1D MS relative abundances and the resulting higher rate of pC2DMS peak assignment. Shown below are the results of the structure assignment by the Mascot and Protein Prospector on the basis of the 1D MS (left) and pC2DMS (right) data.
Figure 13:
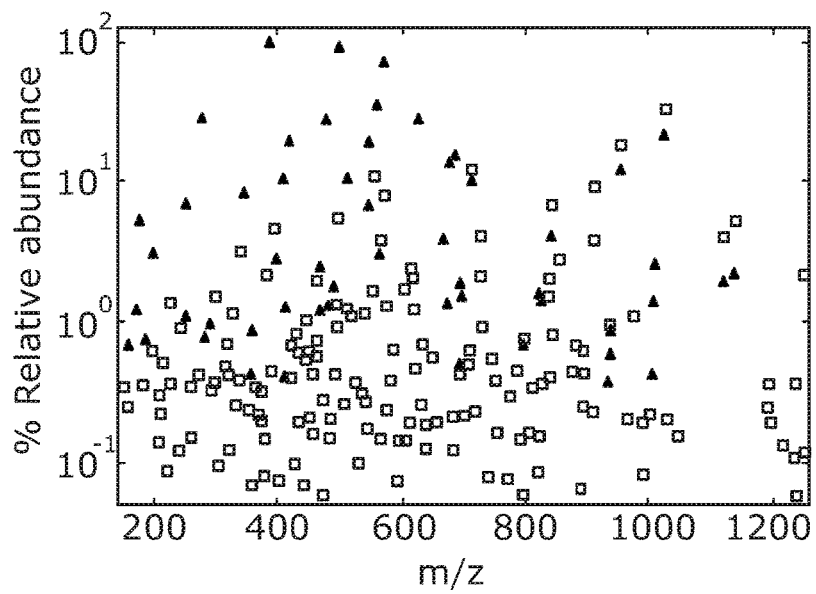
Figure 13:
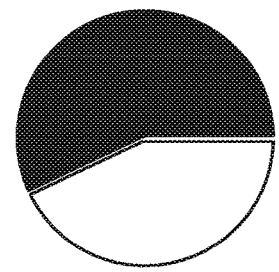
Figure 13:
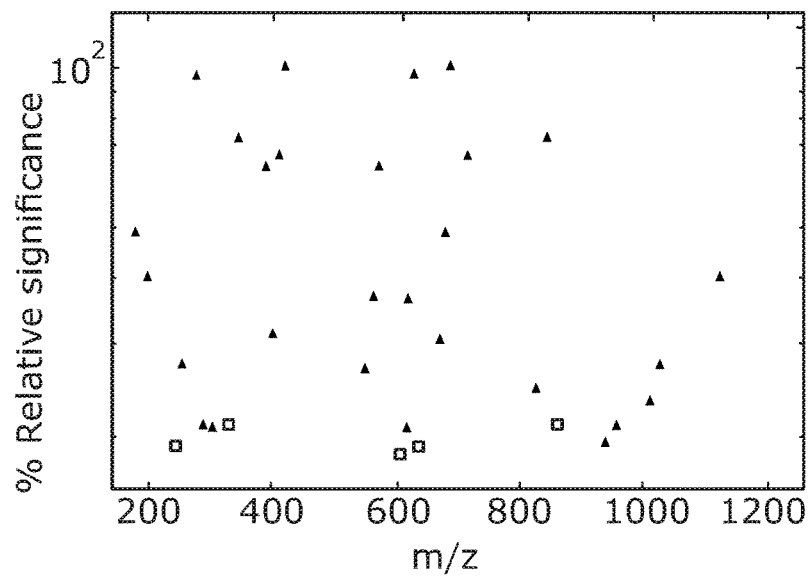
Figure 13:
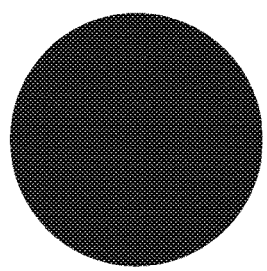
Figure 13:
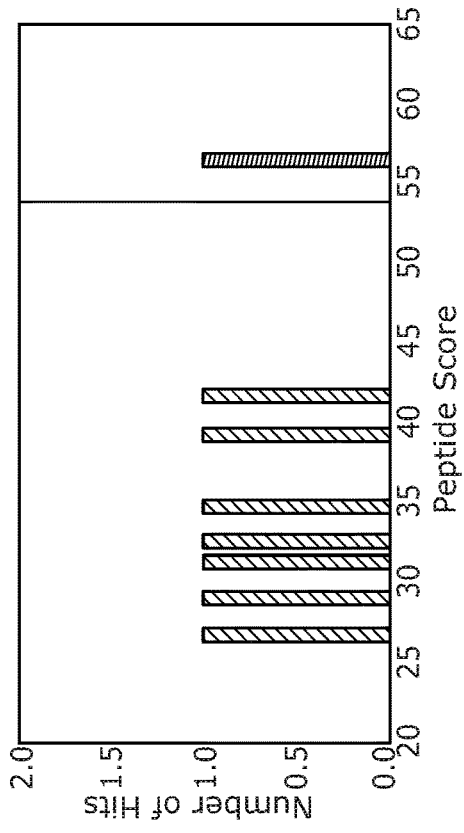
Figure 13:
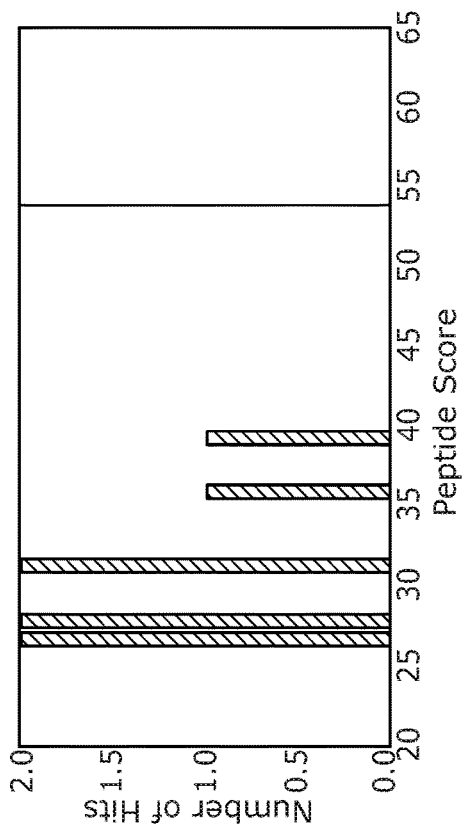
Figure 13:
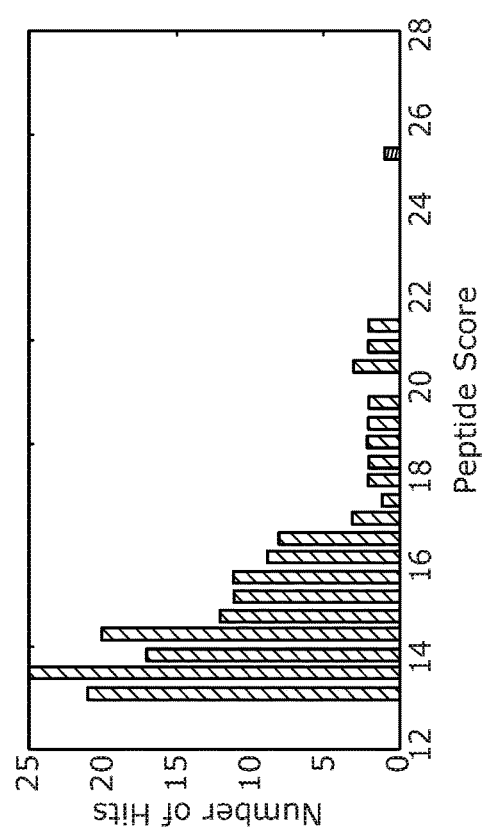
Figure 13:
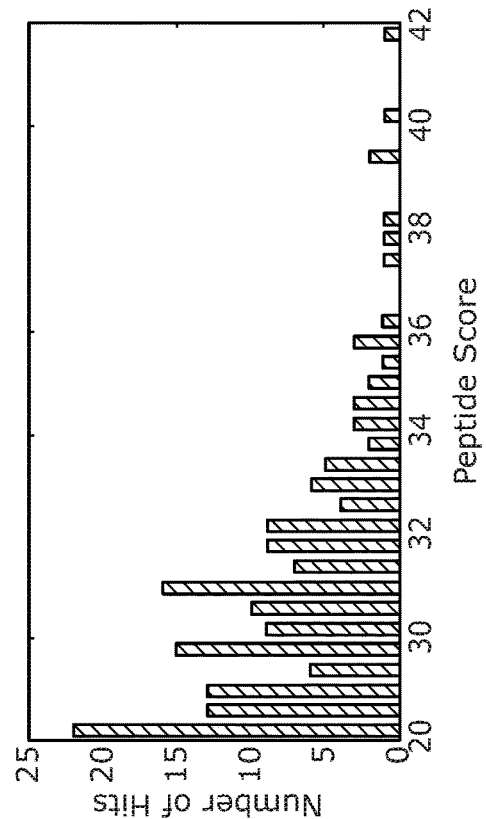
Figure 14:
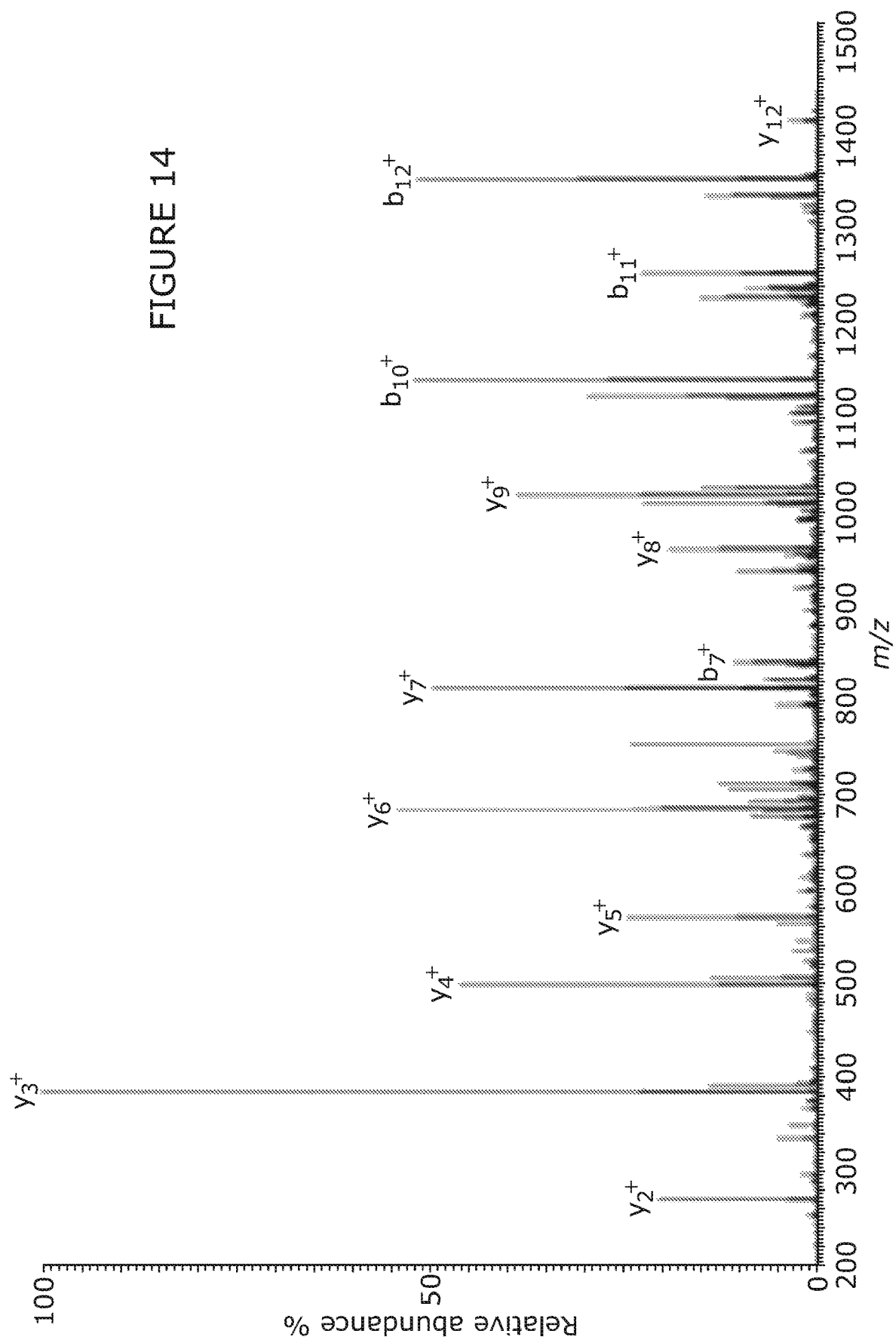
Figure 14:
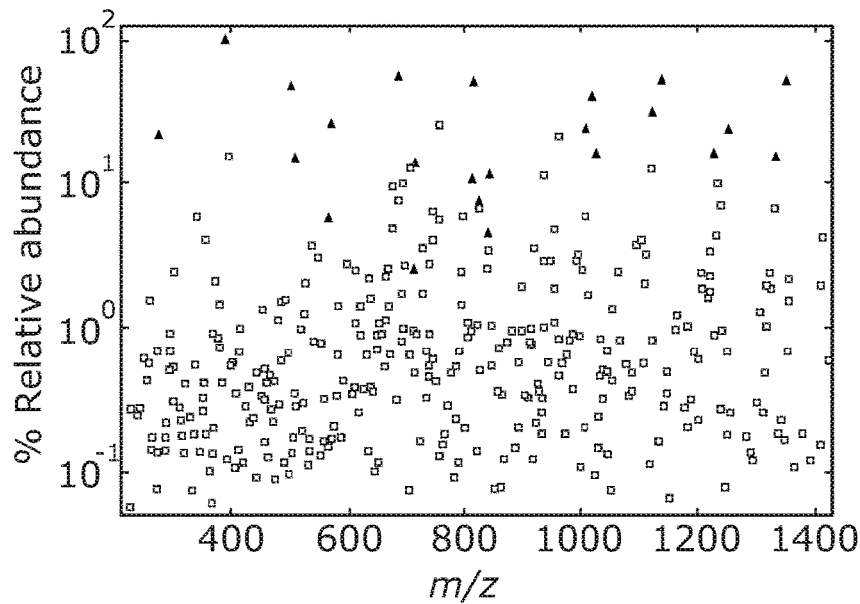
Figure 14:
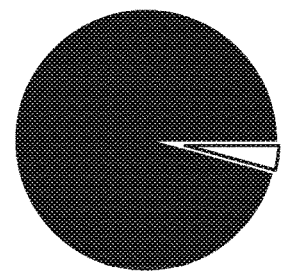
Figure 14:
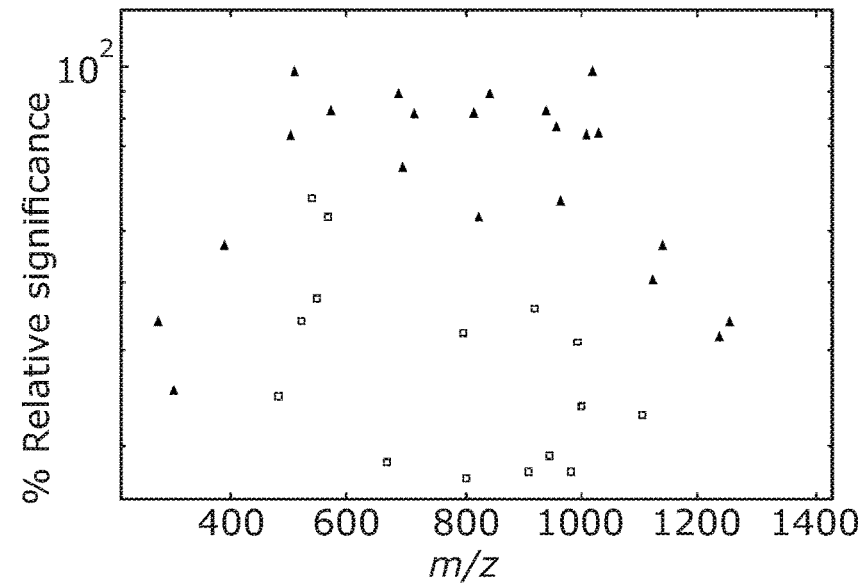
Figure 14:
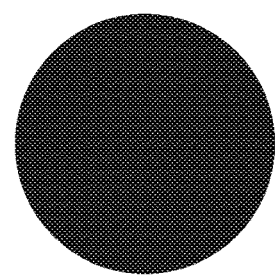
Figure 14:
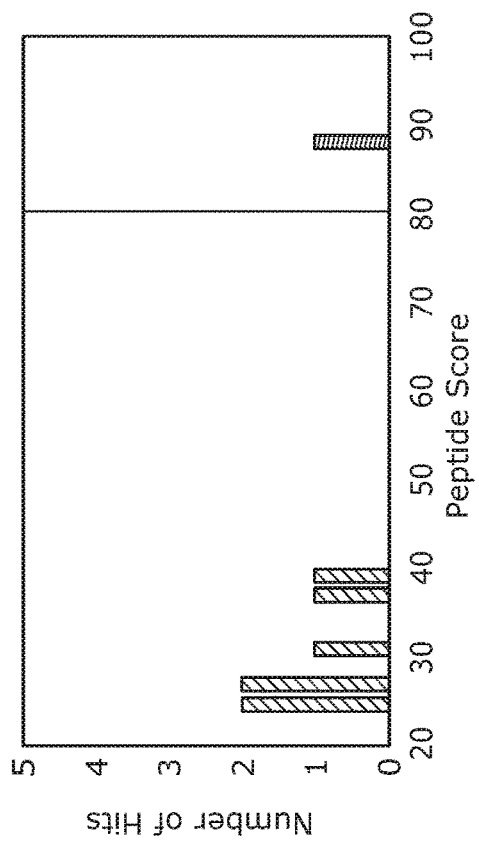
Figure 14:
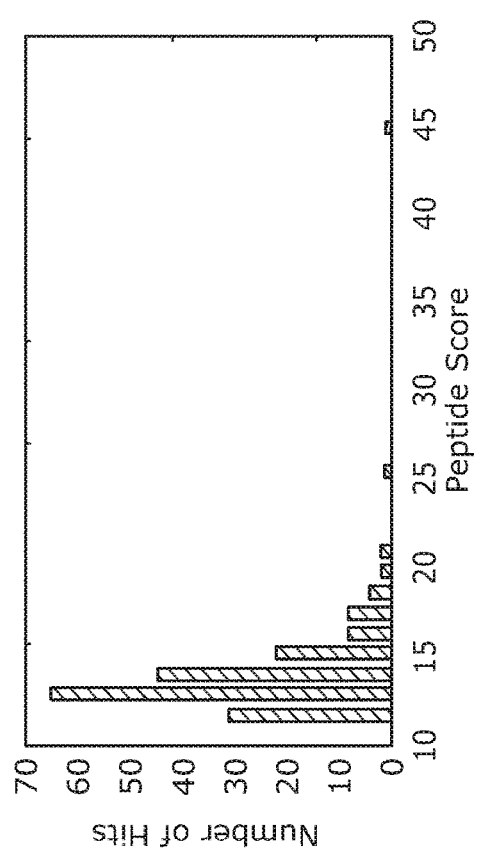
Figure 14:
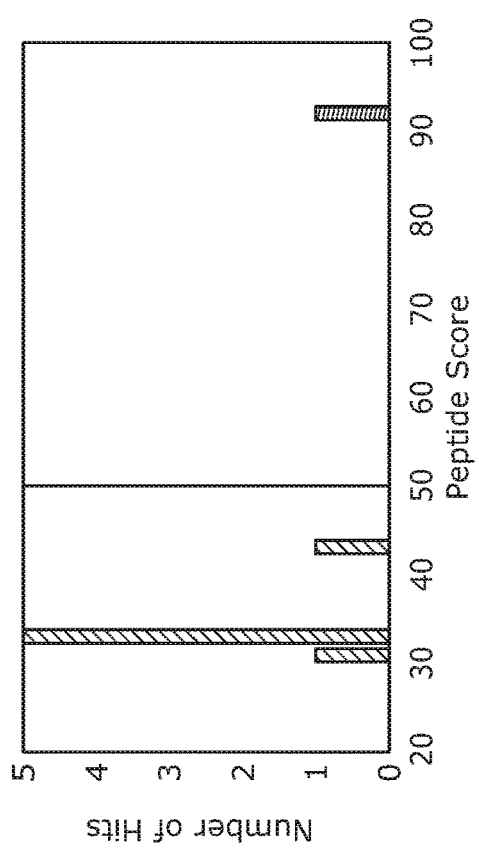
Figure 14:
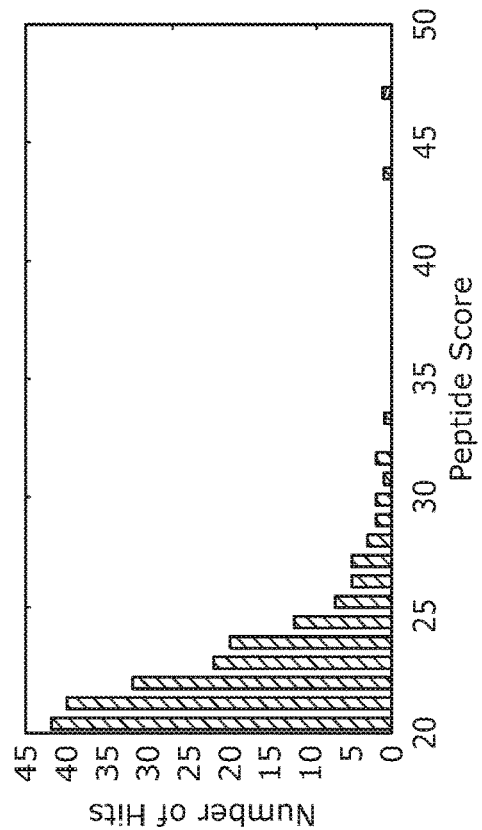
Figure 15:
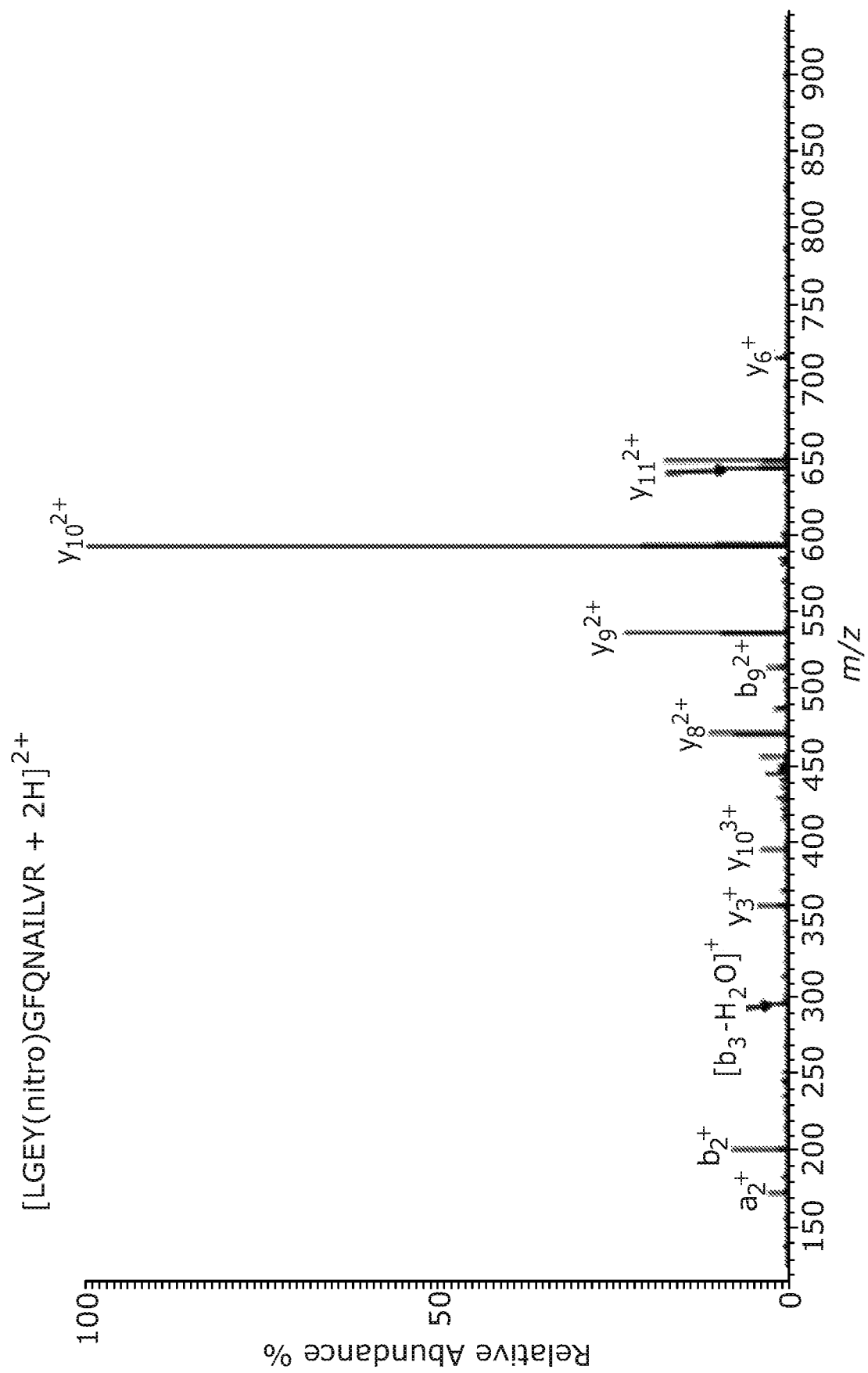
Figure 15:
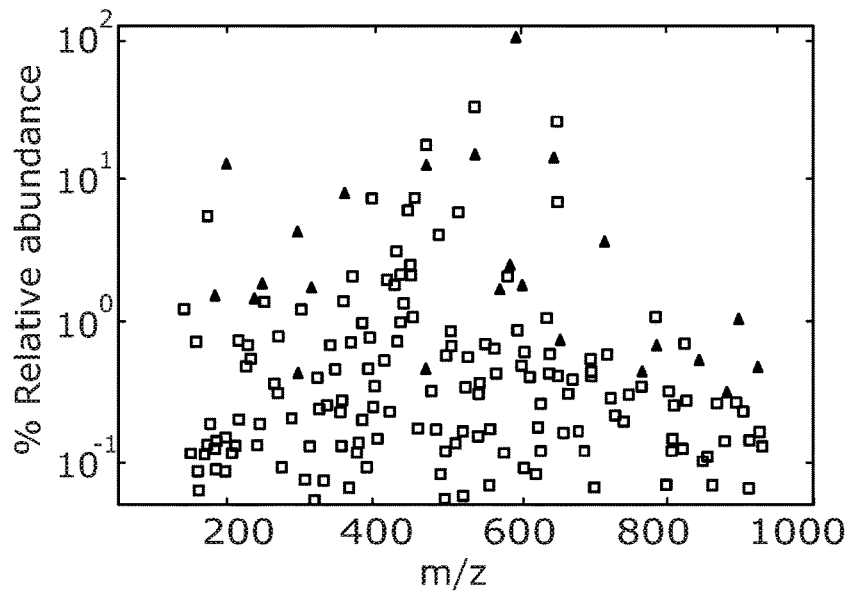
Figure 15:
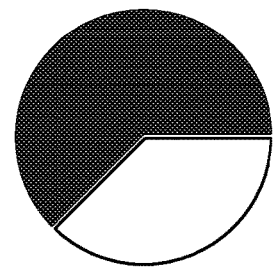
Figure 15:
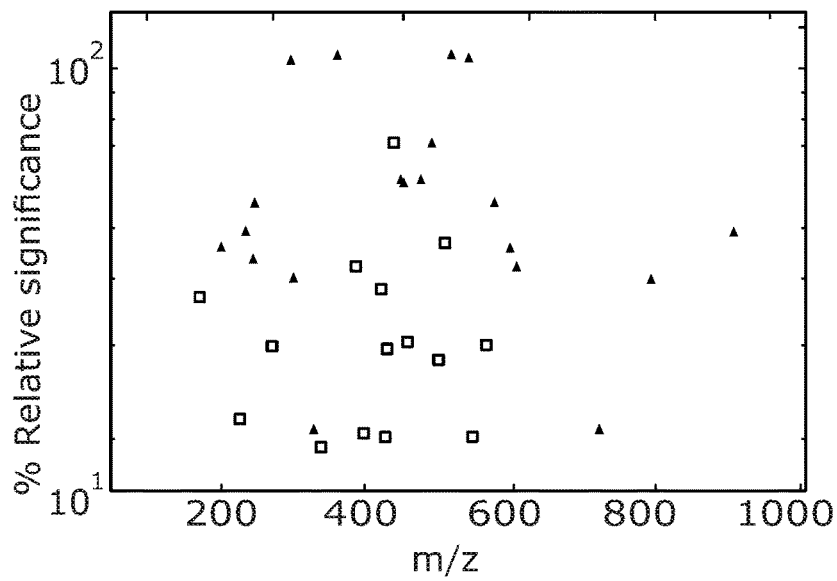
Figure 15:
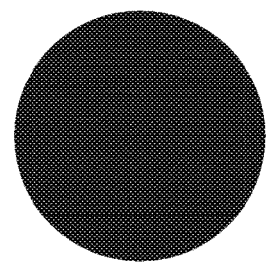
Figure 15:
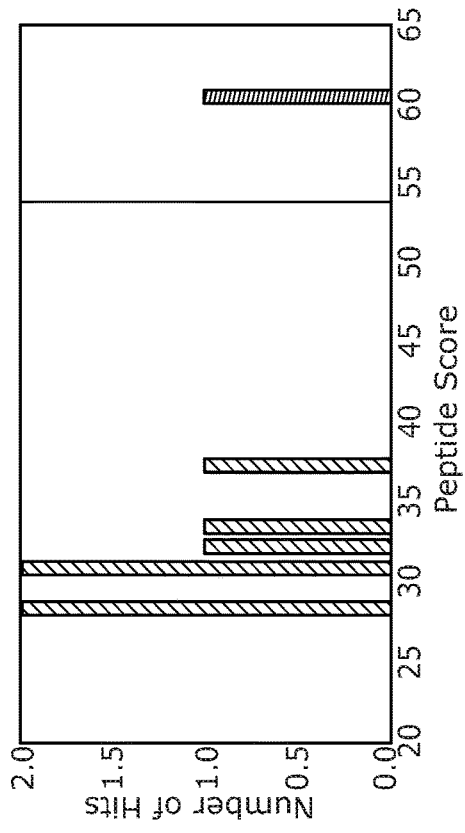
Figure 15:
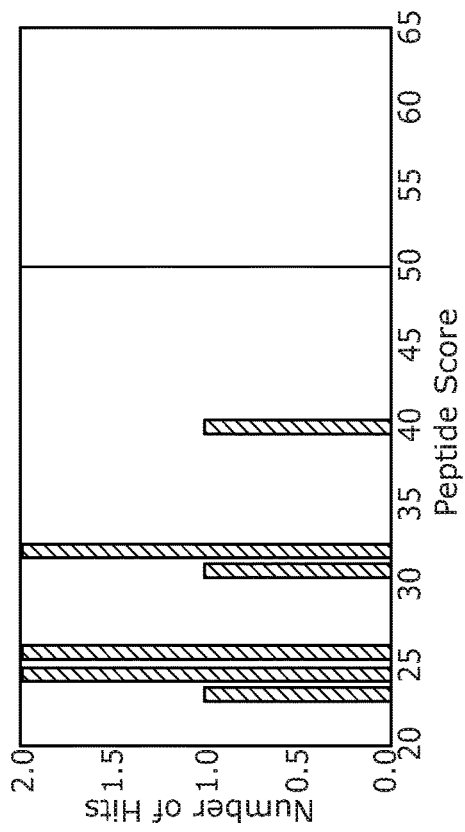
Figure 15:
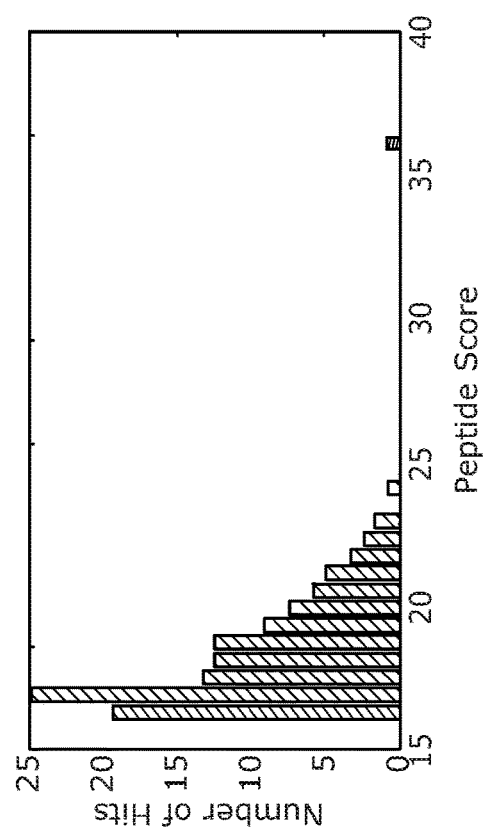
Figure 15:
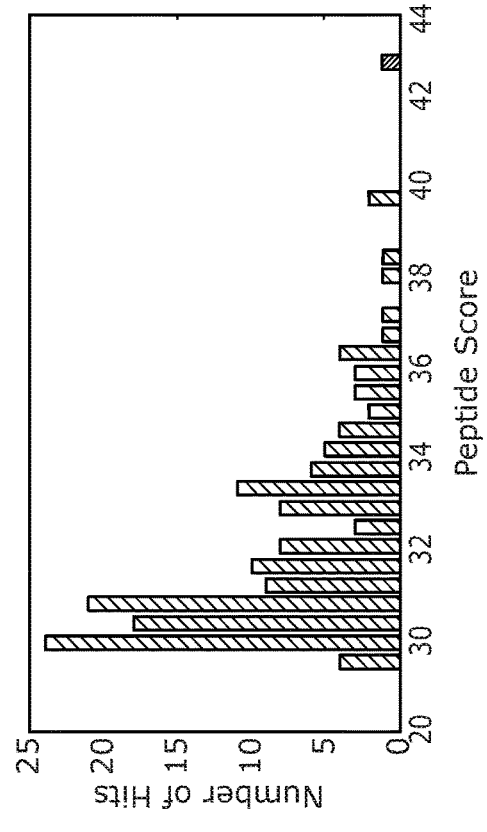
Figure 16:
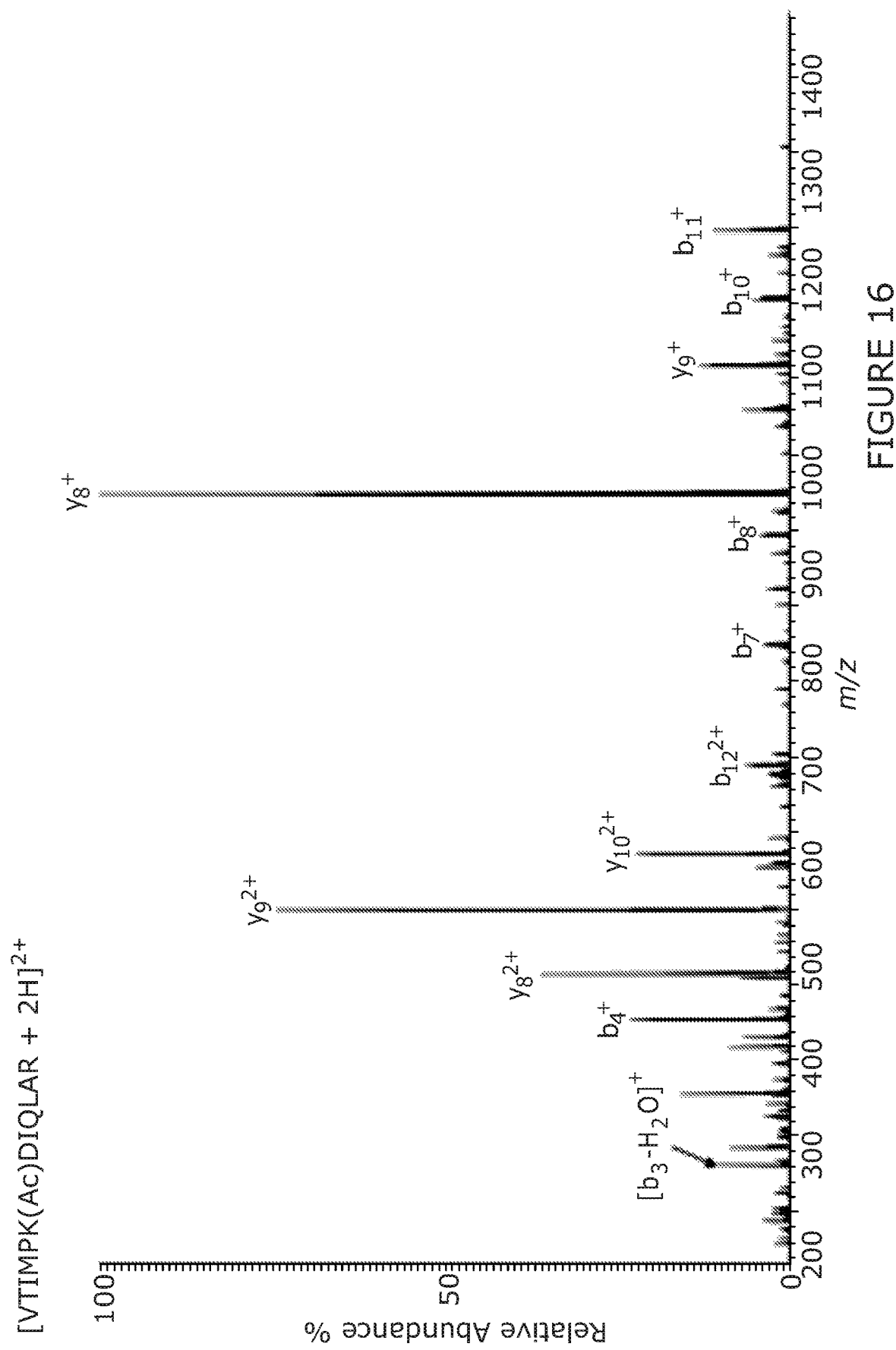
Figure 16:
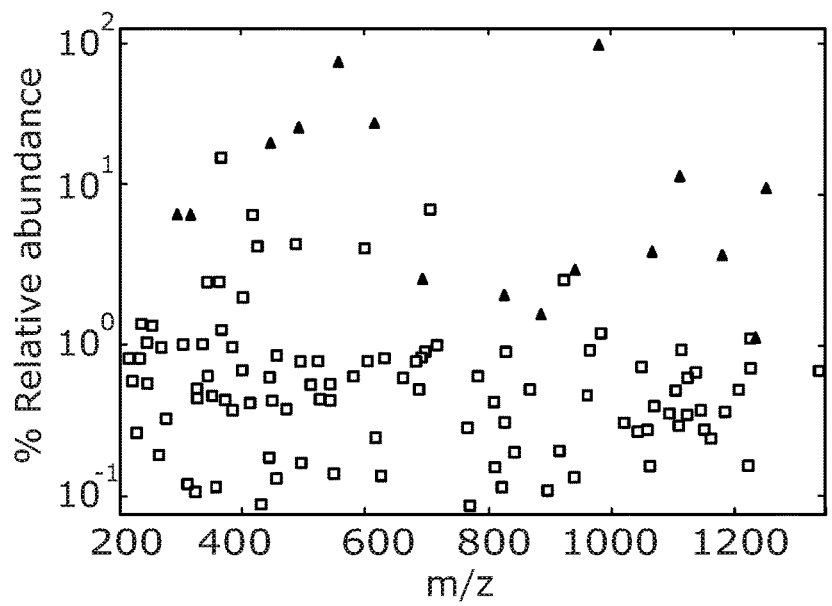
Figure 16:
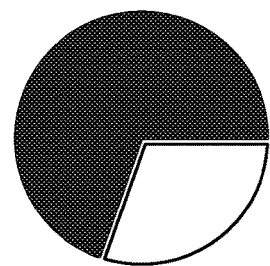
Figure 16:
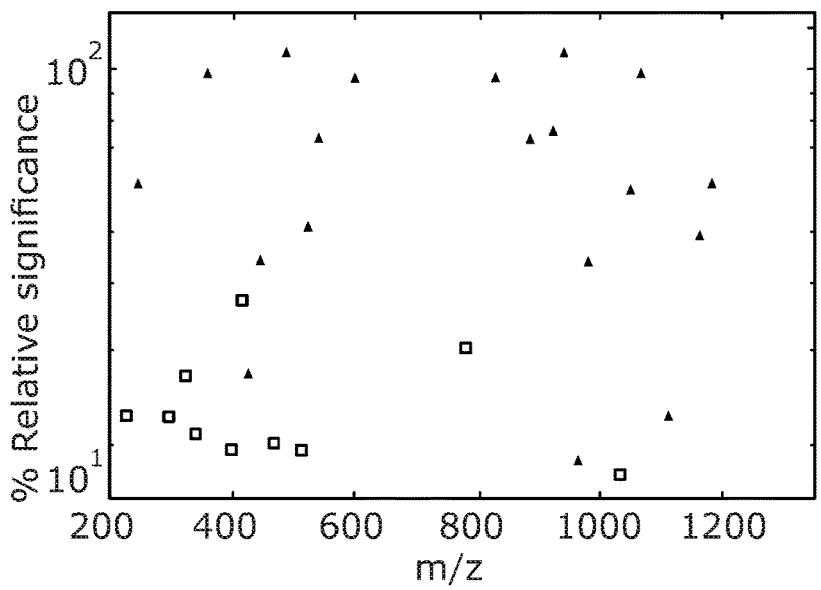
Figure 16:
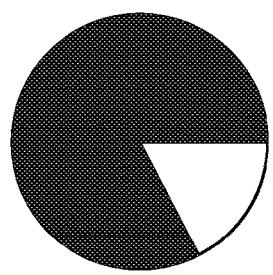
Figure 16:
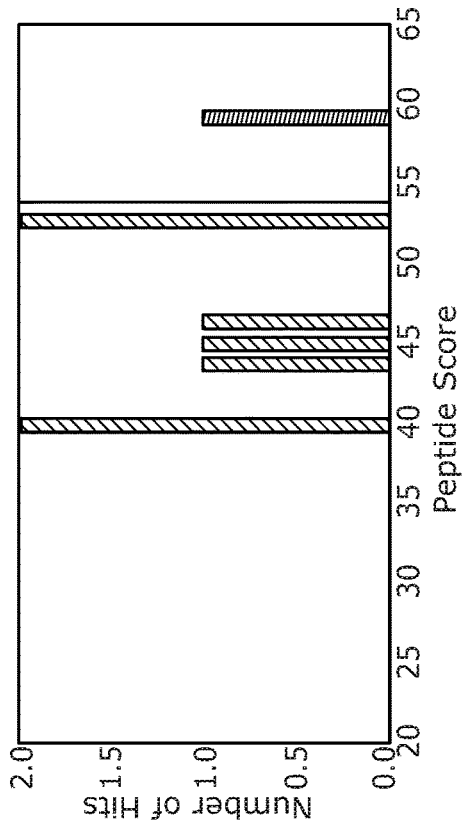
Figure 16:
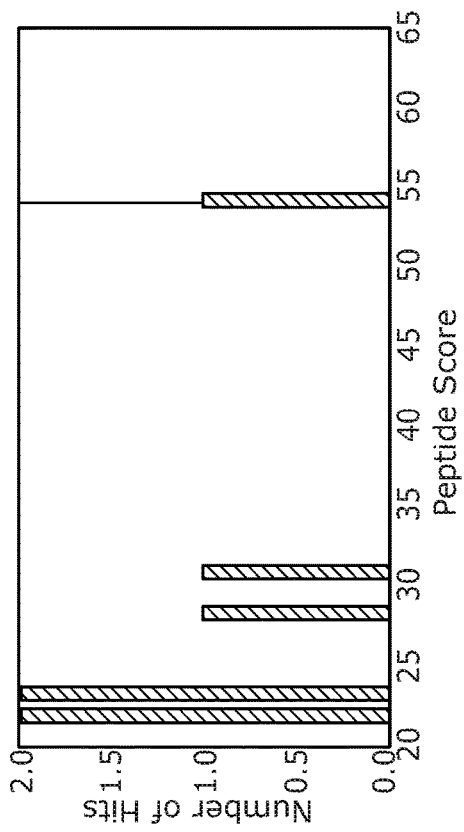
Figure 16:
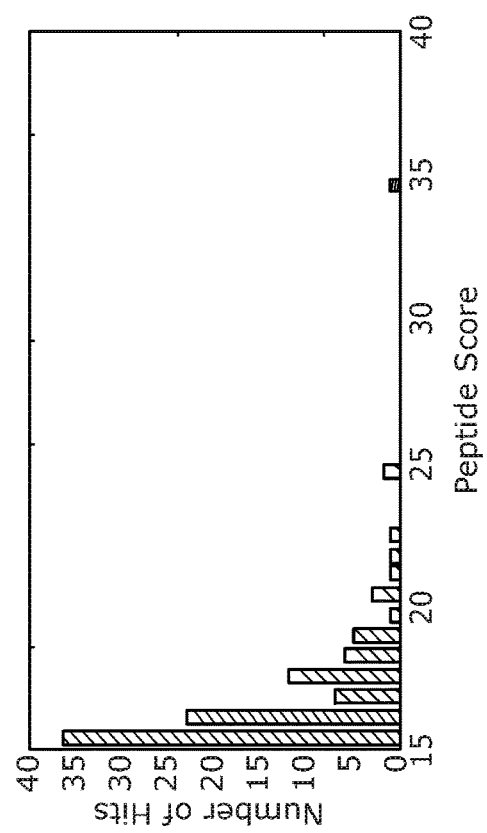
Figure 16:
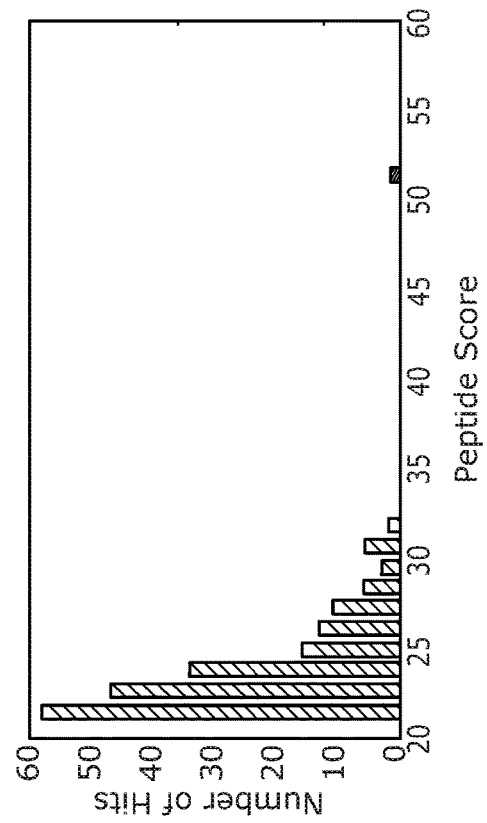
Figure 17:
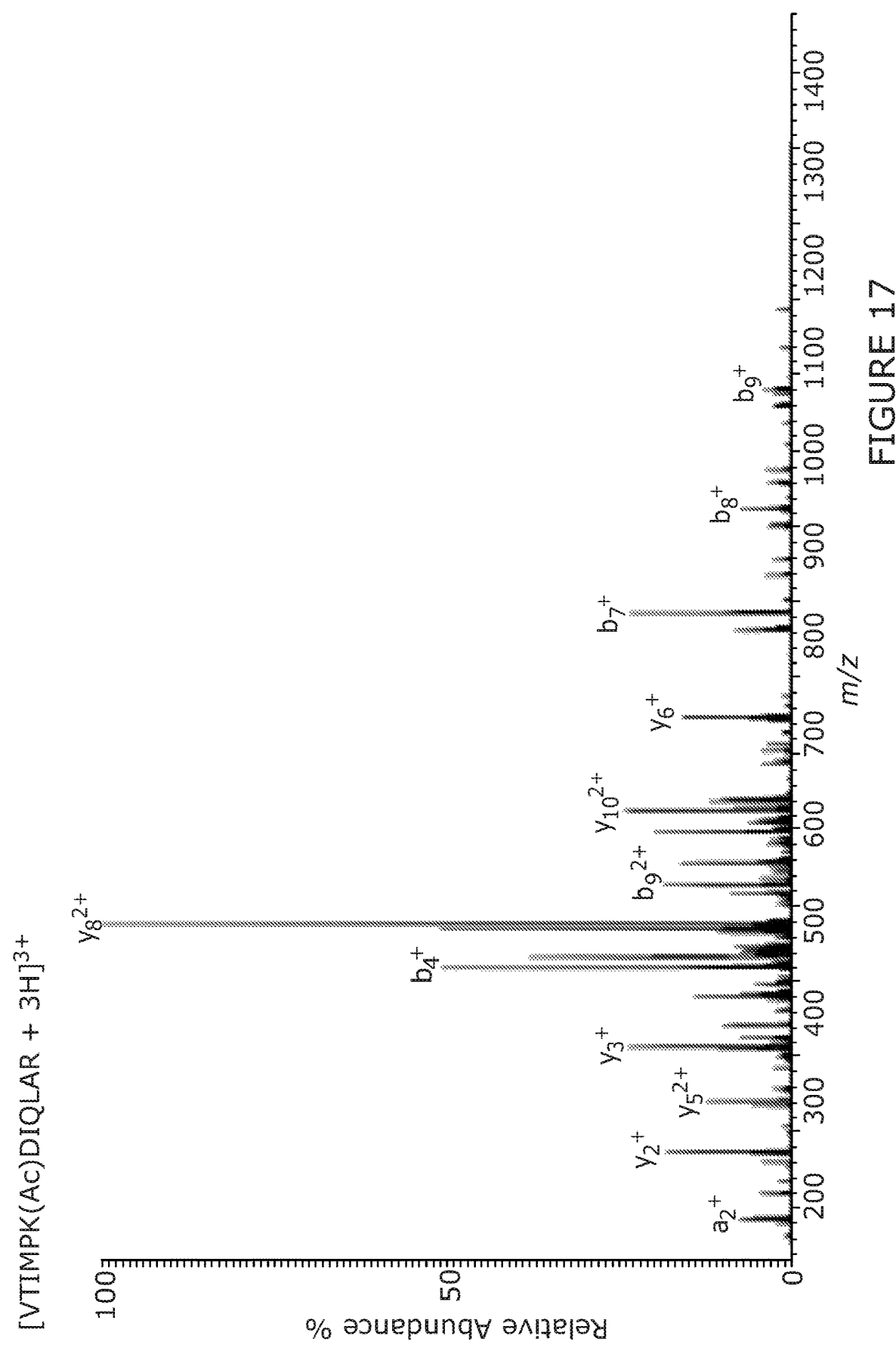
Figure 17:
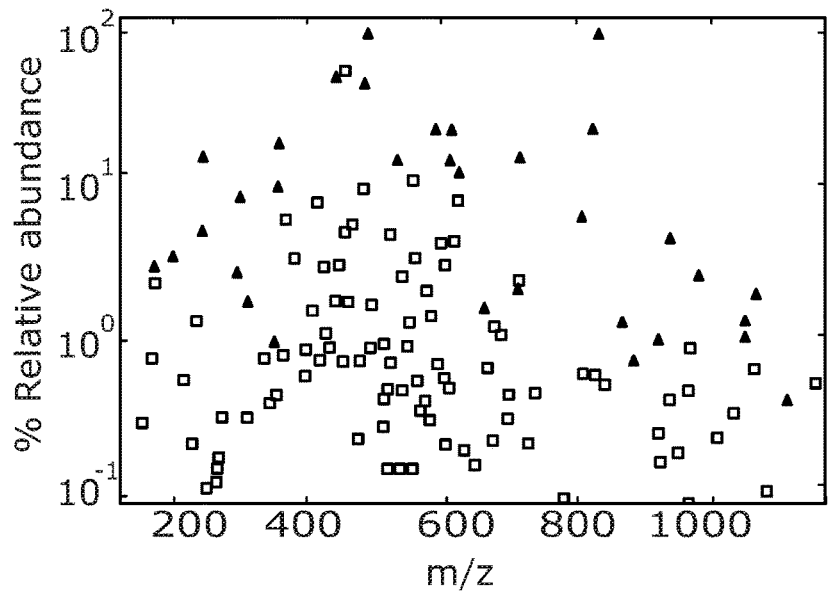
Figure 17:
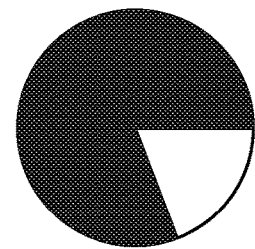
Figure 17:
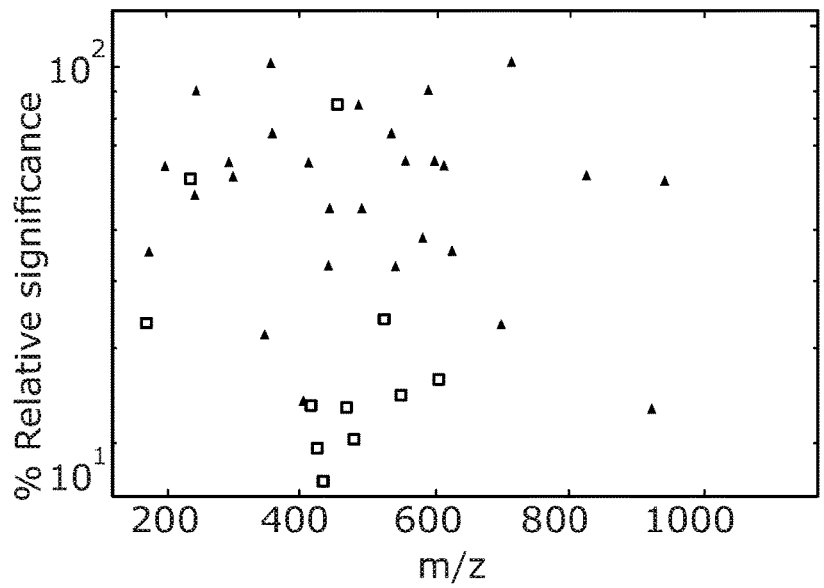
Figure 17:
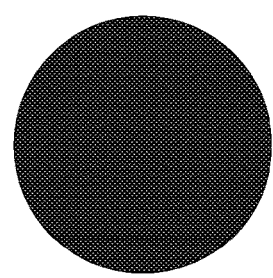
Figure 17:
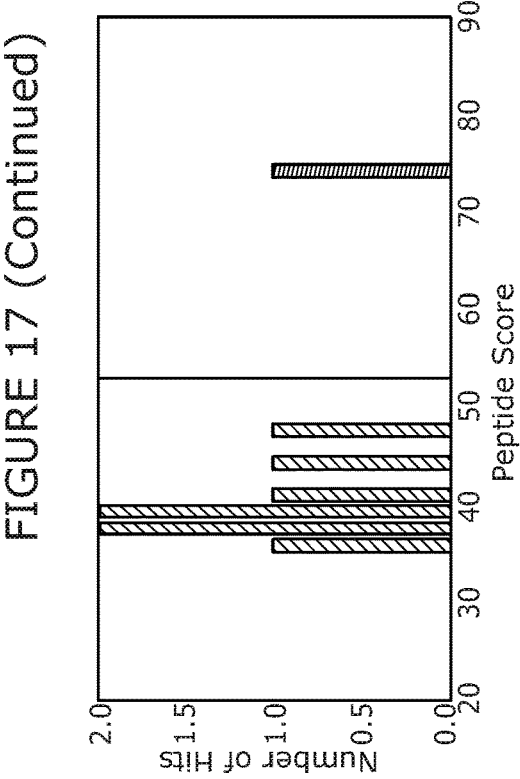
Figure 17:
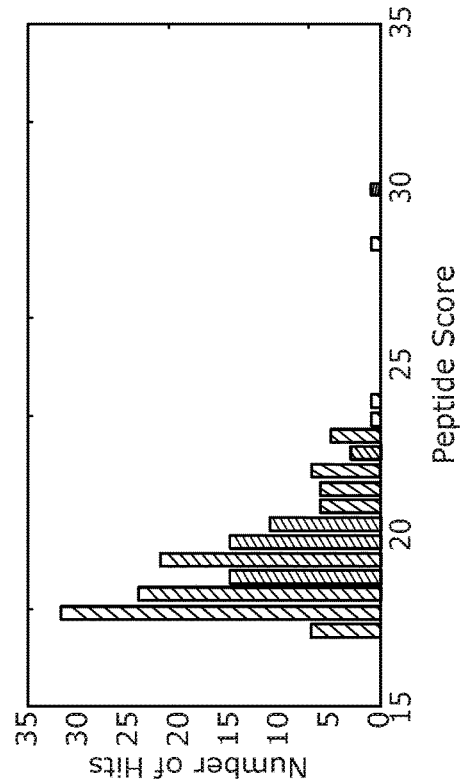
Figure 17:
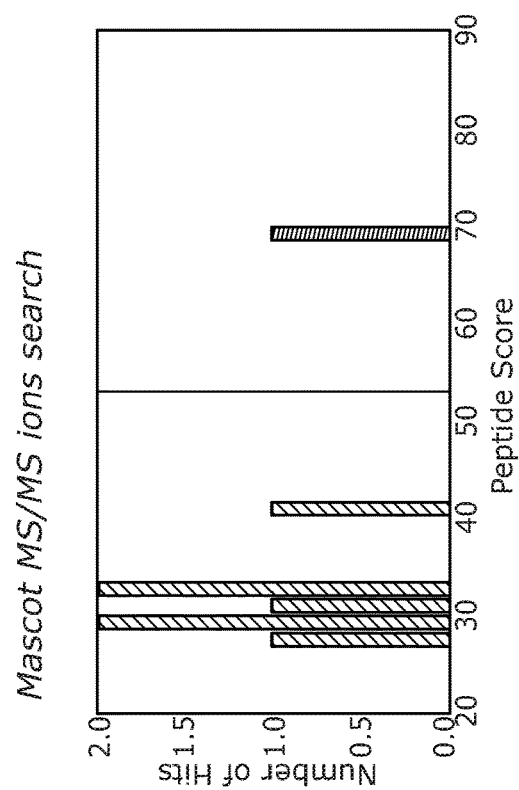
Figure 17:
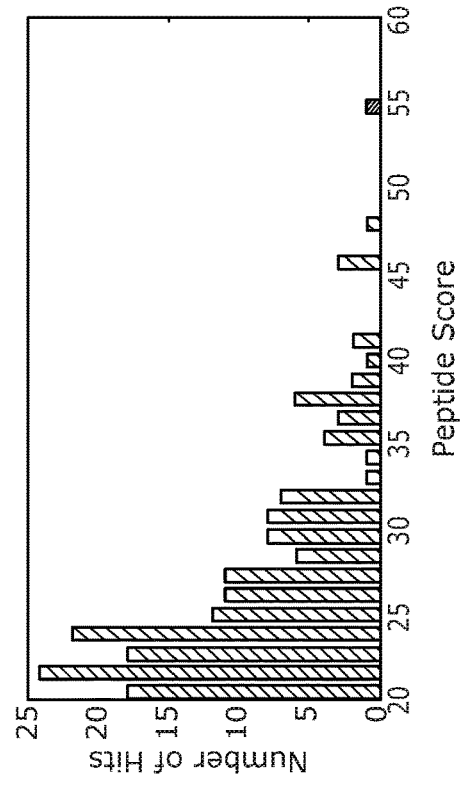
Figure 18:
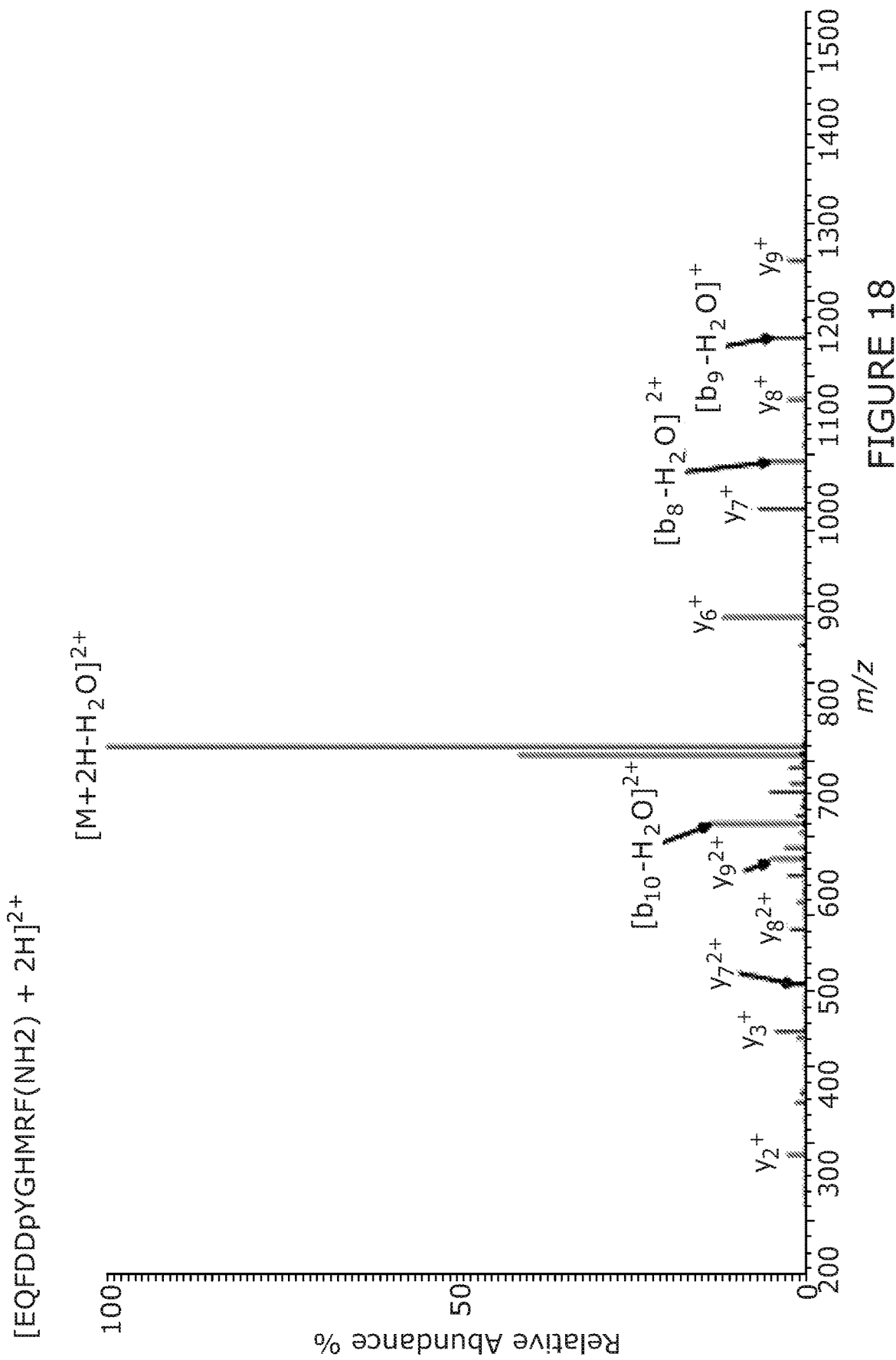
Figure 18:
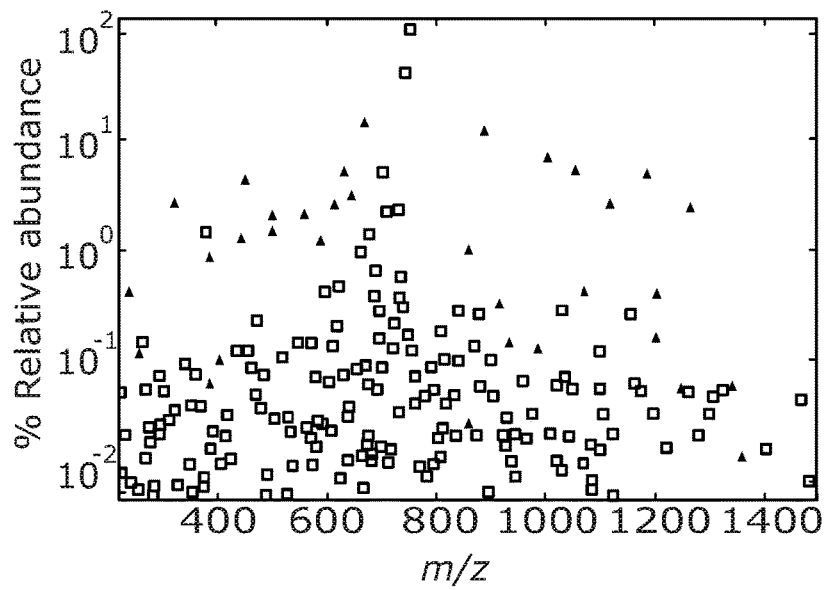
Figure 18:
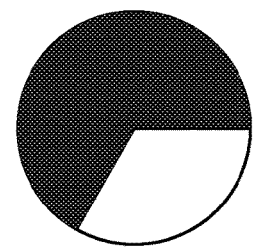
Figure 18:
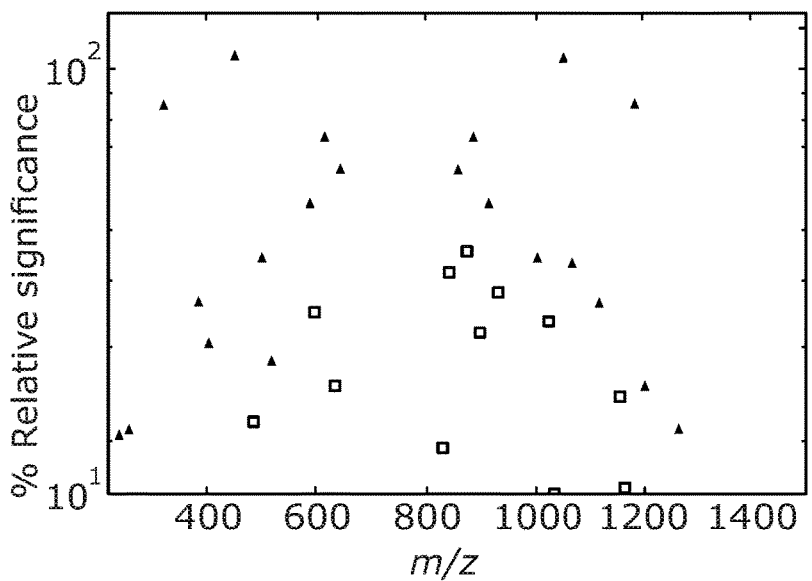
Figure 18:
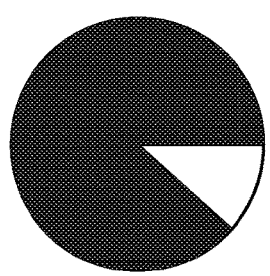
Figure 18:
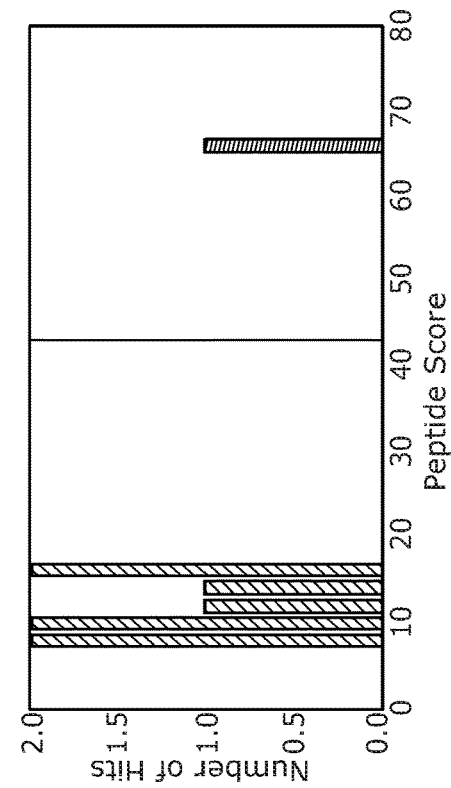
Figure 18:
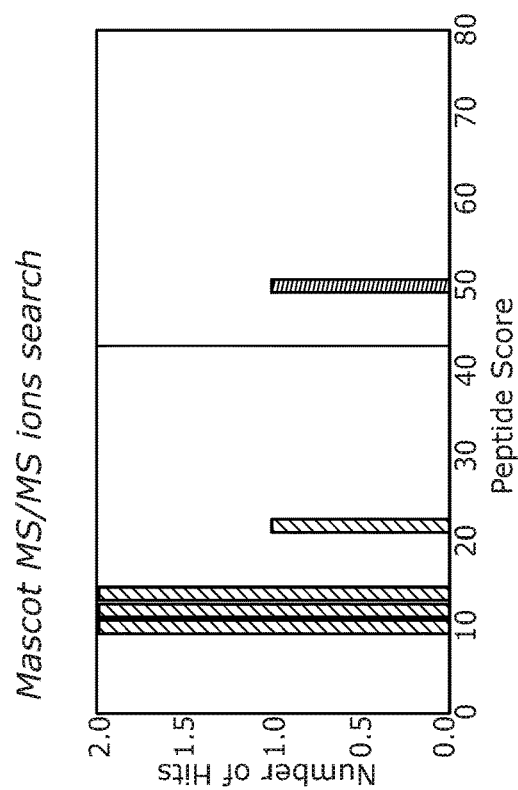
Figure 18:
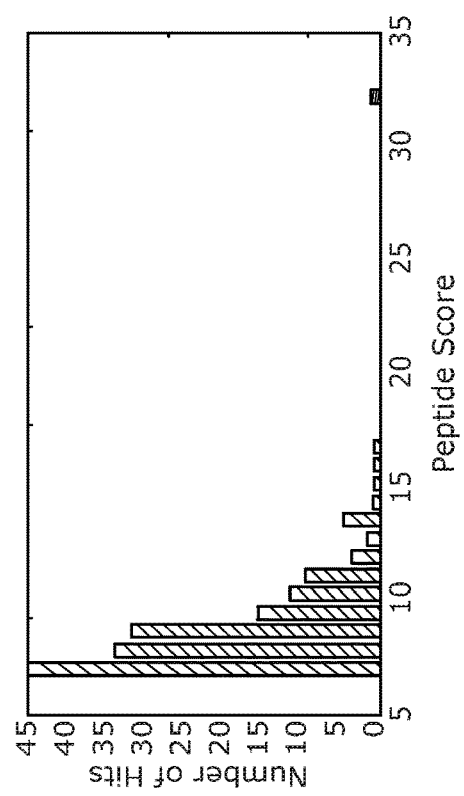
Figure 18:
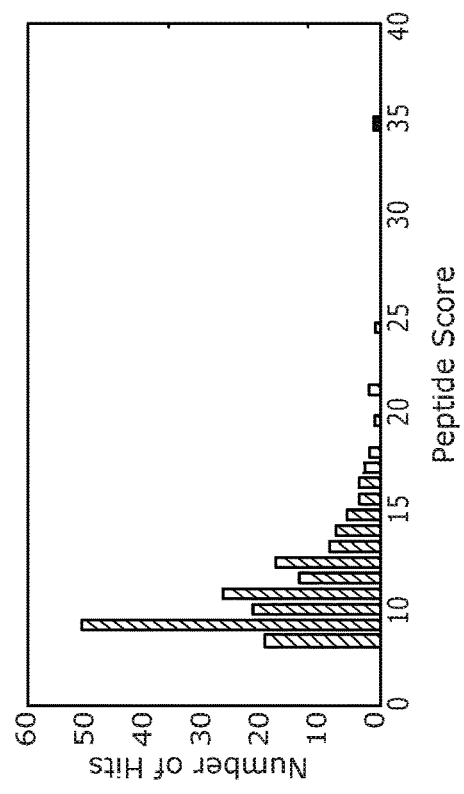
Figure 19:
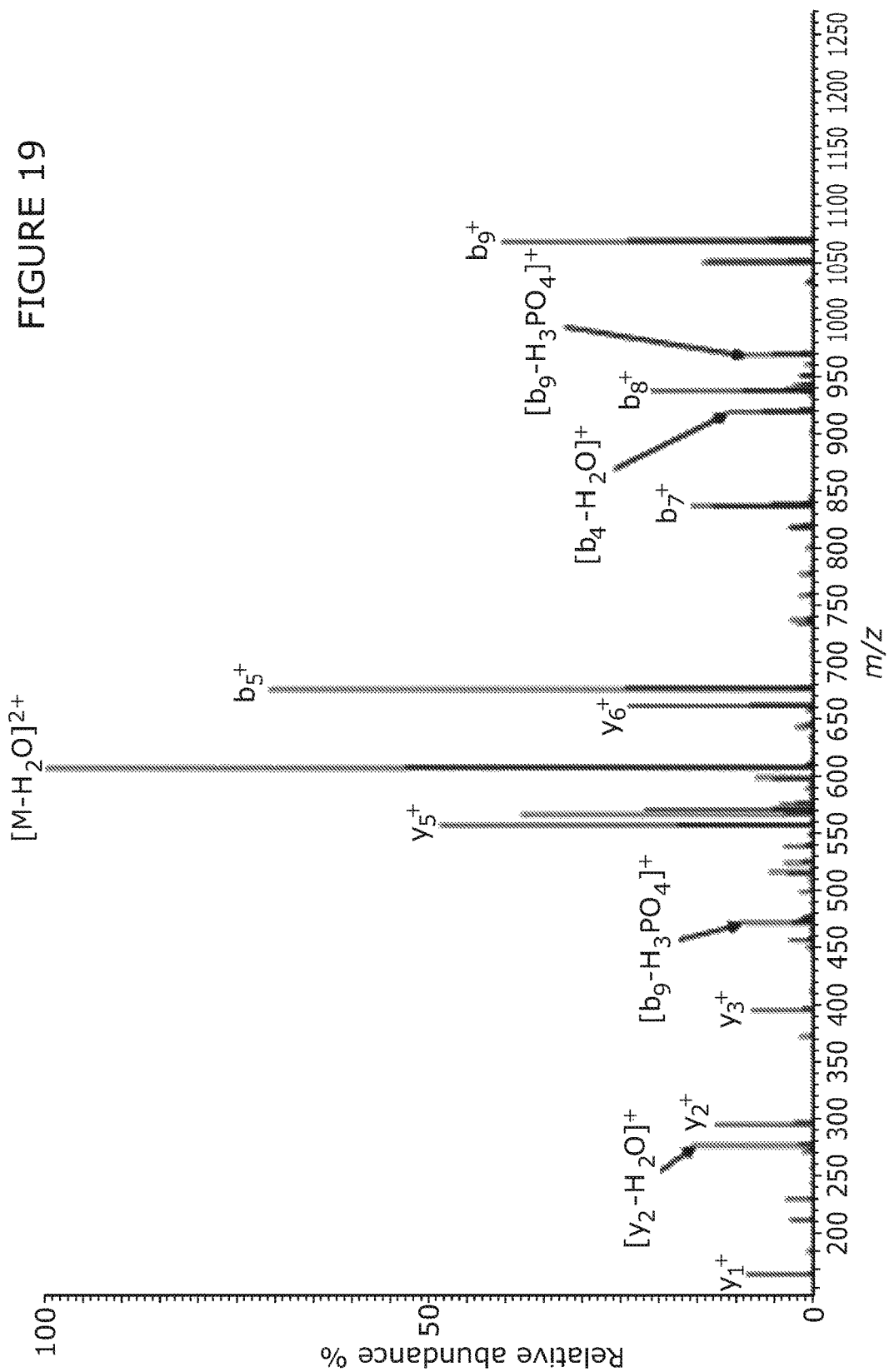
Figure 19:
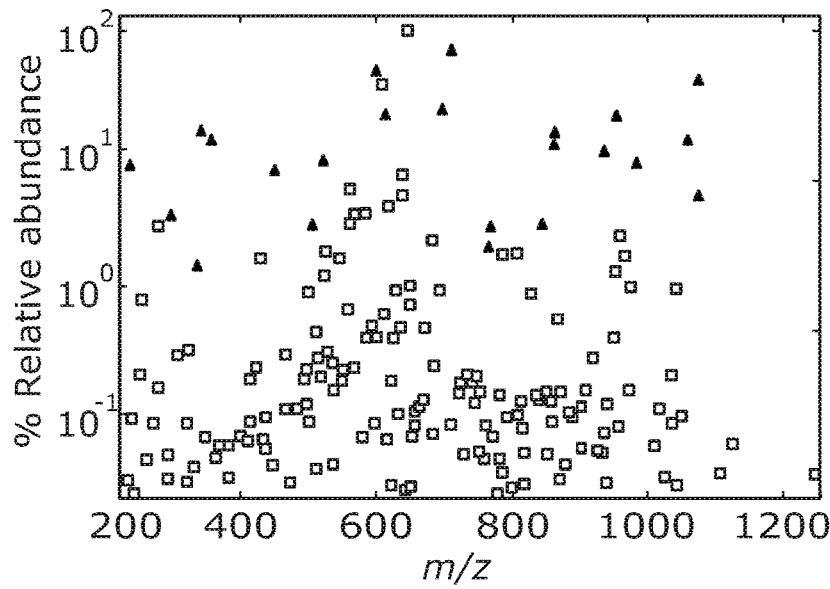
Figure 19:
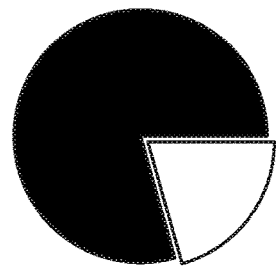
Figure 19:
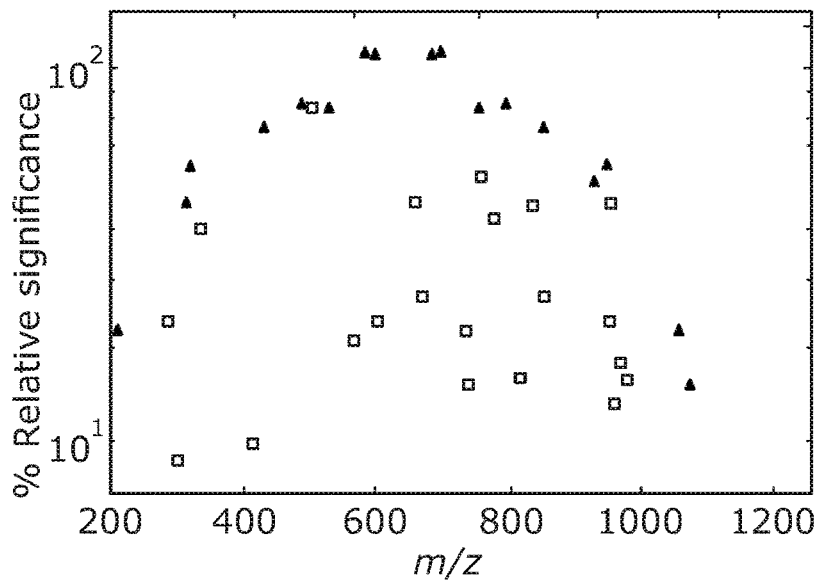
Figure 19:
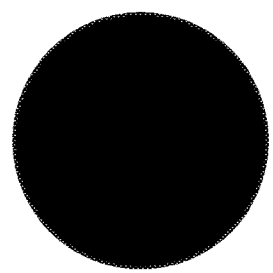
Figure 19:
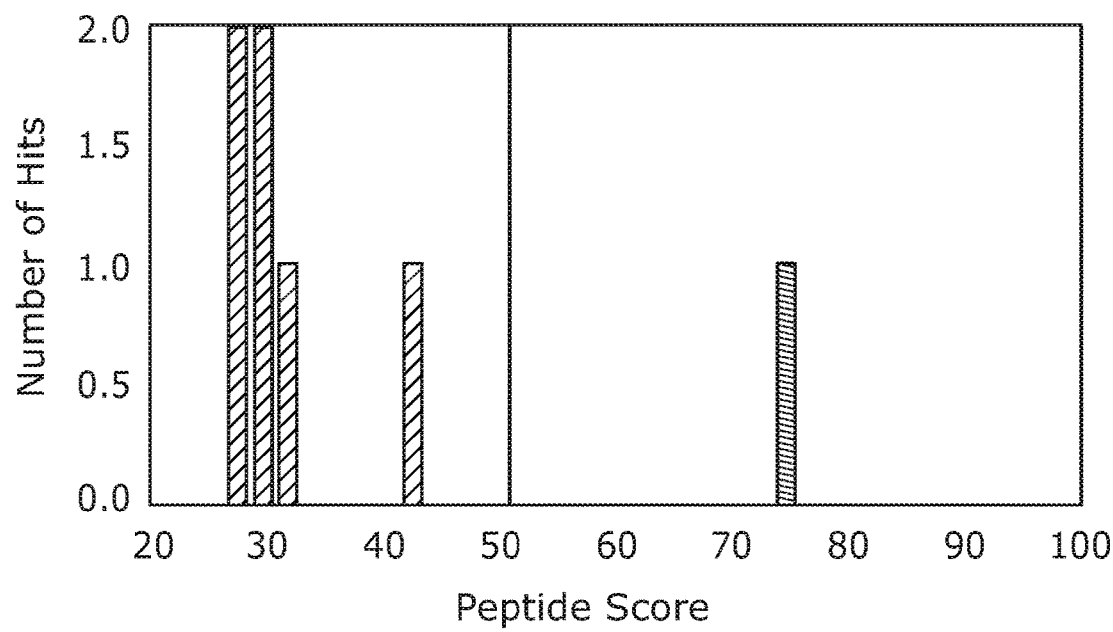
Figure 19:
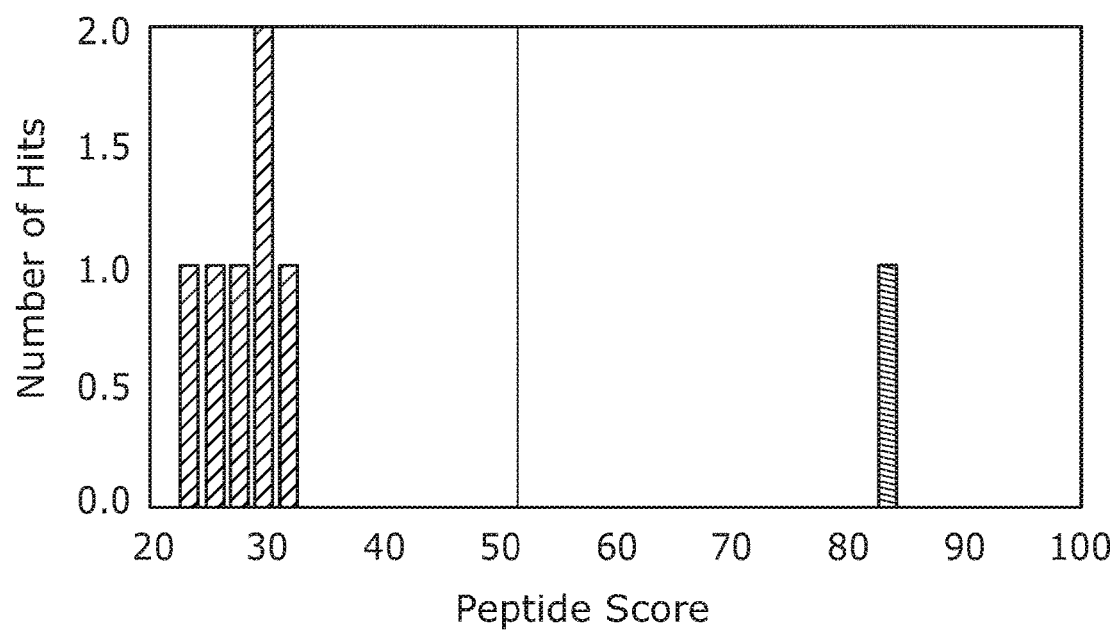

The partial covariance mapping procedure according to the invention was applied to the CID spectrum of the [EQFDDsYGHMRF(NH$_2$)+2H]$^{2+}$ ion using the total fragment ion count as the single fluctuating parameter. The map can be seen at FIG. 12(b), showing sequence specific fragment ions as triangles and other spectral signals as squares. In order to make the map amenable to automatic spectrum-structure assignment, a procedure for automatic peak picking across the resulting 2D map is introduced to create the ranked lists of the correlated fragments. This involves calculating a statistical significance, S(X,Y), of each off-diagonal peak on the partial covariance map, $$S(X,Y)=V[p\ \mathrm{Cov}(X,Y;I)]/\sigma(V) \qquad (3)$$

where V is the volume under a partial covariance peak corresponding to statistical correlation of fragments X and Y and σ(V) is the variance of this volume computed upon jackknife resampling.

The spectral correlations are ranked according to their statistical significances and each CID fragment is assigned with its relative significance as percentage of its highest spectral correlation relative to the highest S(X,Y) on the 2D map. The resulting fragment ranking is directly comparable with a standard 1D data ranking, done according to the relative ion intensities, also known as relative abundances.

It is instructive to compare the two CID fragment rankings (see FIGS. 12(b) and (c). Indeed, the relative spectral statistical significances of the structure-confirming fragment ions are two to four orders of magnitude higher than their relative abundances. Noise-level sequence-specific peptide signals of the standard 1D spectrum are therefore shown to give rise to high-significance off-diagonal correlations in the partial covariance map provided by the invention, demonstrating its use for high-confidence peptide identification. It is noteworthy that the relative spectral statistical significances provided by the invention can be used directly by the state of the art automatic analysis tools instead of the relative abundances.

Attempting such identification of the doubly protonated perisulfakinin, the invention provides a spectacular result: the scoring algorithms (Mascot and MS Tag) that misinterpreted the 1D spectrum or interpreted it with low confidence, provide a clear high-confidence identification of the same peptide on the basis of the relative spectral statistical significances. With further investigation of the method of the invention, it is shown that such an identification pattern is typical for the peptide with challenging one dimensional CID spectra (i.e. with low-abundance sequence-specific peaks), as can be seen from FIGS. 13 to 19, which demonstrate the improvement in performance of standard 1D database searches using signals produced by the method of the invention.

In each of FIGS. 13 to 19, the 1D mass spectra are plotted, with selected manually identified structurally informative spectral signals labelled.

In the scatter plots, each point represents a peak in the peak list fed to the automatic database search engine. The m/z of the peak is plotted on the x-axis, with its relative abundance (for 1D data) or relative significance (as provided by the invention) on the y-axis. Triangles represent those peaks which were identified as structurally informative signals by the automatic search engine, whilst squares indicate those peaks which were not and therefore contribute to spectral noise.

The pie charts represent in the darker shade the percentage of those peaks selected by the Mascot automatic database search engine intensity-based filtering process which are successfully identified as structural signals. It can be seen that a greater percentage of structurally informative signals identified from these intensity-filtered peaks results in a more confident and accurate spectral assignment to a peptide sequence.

Where the number of identified structural signals exceeds the number of intensity-filtered signals, this is a result of one or more 'multiple matches' between an experimental spectral signal and the expected spectral signals for the database peptide sequence. In this case, the m/z of an experimental signal falls within the fragment ion tolerance of +/−0.8 Da for two (or more) different expected spectral signals. In the vast majority of cases this is a result of the close proximity in m/z of neutral loss of $H_2O$ and neutral loss of $NH_3$ (=0.98 Da for singly charged species and 0.49 Da for doubly charged species), both of which are usually expected from a fragment ion and are considered as independent expected spectral signals.

The histograms illustrate the comparative success of automatic database search engines (designed to perform with 1D mass spectral data only) when provided with 1D mass spectral data vs 2D data produced in line with the invention. The identification score of a particular peptide sequence when matched with the provided experimental data is plotted on the x-axis, with the number of database sequences giving a particular score on the y-axis. A single match scoring significantly higher than its 'competitors' represents a confident and unique sequence assignment for a given set of experimental data. For Mascot (Matrix Science) searches, the shaded area represents the identity threshold, calculated by the search engine itself as the score above which a peptide sequence assignment can be treated as a confident match.

While the search engine analysis of the 1D MS data leads to failures in 3 out of 7 cases, the same algorithm applied to the pC2DMS data finds the correct structure in all the cases. Moreover, in the cases where both 1D MS and pC2DMS data analysis leads to correct peptide identification, the latter produces peptide score higher above the identification threshold, i.e. the identification is achieved with higher confidence.

Methods of the present invention therefore provide new general two-dimensional mass spectrometry based on partial covariance mapping and demonstrated that the method can be applied to structural analysis in proteomics using a standard mass spectrometer platform. Without requiring any a priori information about the analysed peptides, the partial covariance map shows correlations between the fragment ions formed in the same or in the consecutive dissociations, facilitating interpretation of the spectra and matching them to the correct peptide structures. The assignment of relative spectral statistical significances to the CID fragments allows the user to confidently derive correct peptide sequences from spectral peaks, including the unusual, complex origin and noise-level signals that are routinely misinterpreted or disregarded by traditional one dimensional mass spectrometry.

The methods of the present invention therefore solve the poor interpretation problem of proteomic mass spectrometry and opens new opportunities for characterisation of biomolecules. Such methods could be applied to many other forms of spectroscopy. Other spectroscopic methods are suited to the analysis approach as the data they produce comprise a plurality of spectra that can be divided into bins. In all it is possible to identify a control parameter that is indicative of synchronised fluctuations that can be employed in the partial covariance analysis to reveal the true statistical correlations between spectral bins.

Preferences and options for a given aspect, feature or parameter of the invention should, unless the context indicates otherwise, be regarded as having been disclosed in combination with any and all preferences and options for all other aspects, features and parameters of the invention.

The listing or discussion of background information or an apparently prior-published document in this specification should not necessarily be taken as an acknowledgement that the information or document is part of the state of the art or is common general knowledge.

The invention claimed is:

1. A method of analysing a structure of a composition of matter in a sample comprising:
   obtaining a data set comprising a plurality of spectra from the composition, from a first method of analysis;
   dividing each of the spectra into a plurality of bins;
   determining a control parameter or parameters indicative of synchronised fluctuations in signal intensity across some or all bins, resulting in universal correlation between said bins;
   determining a partial covariance of different bins across the plurality of spectra using the control parameter or parameters to correct the correlation of intensity fluctuations between said bins.

2. The method of claim 1 in which determining partial covariance pCov(X,Y; I) is performed according to the equation:

$$p\,\mathrm{Cov}(X,Y;I) = \mathrm{Cov}(X,Y) - \mathrm{Cov}(X,I)\mathrm{Cov}(Y,I)/\mathrm{Cov}(I,I),$$

where X and Y each represent spectrum intensity for each bin and I represents the control parameter and $$\mathrm{Cov}(Y,X) = \langle YX \rangle - \langle Y \rangle \langle X \rangle,$$

where $\langle \ldots \rangle$ represents an average over the plurality of spectra.

3. The method of claim 1 further comprising two-dimensional mapping the partial covariance between said different bins of the spectra.

4. The method of claim 3 further comprising identifying one or more specious partial covariance peaks having a negative component of a magnitude greater than 100% of its total positive magnitude and removing the specious partial covariance peaks from the map.

5. The method of claim 3 in which mapping the partial covariance comprises two-dimensional mapping the correlation of the fluctuation of intensities in the spectra, the correlation being corrected according to the values of the control parameters or control parameters.

6. The method of claim 1 wherein the data set comprises a plurality of nuclear magnetic resonance (NMR) spectra, electron spin resonance (ESR) spectra, infra-red (IR) spectra, Raman spectra, UV/fluorescence spectra or photoelectron spectra.

7. The method of claim 1 in which the data set comprises a plurality of mass spectra.

8. The method of claim 7 wherein each of the mass spectra comprises a relative abundance or intensity measurement versus a mass to charge ratio.

9. The method of claim 1 in which the composition of matter comprises a plurality of ions generated under decomposition analysis.

10. The method of claim 3 further comprising determining a statistical significance of each peak or element in the partial covariance map.

11. The method of claim 10 in which determining a statistical significance of each peak or bin comprises computing a statistical significance S(X,Y) according to the equation $$S(X,Y) = V[p\,\mathrm{Cov}(X,Y;I)]/\sigma(V)$$

where V is a volume under a partial covariance peak or a volume of a section of the partial covariance function pCov(X,Y;I), and σ(V) comprises a measure of the variance of the volume under the peak or the variance of a volume under the section, wherein determining partial covariance pCov(X,Y;I) is performed according to the equation:

$$p\,Cov(X,Y;I) = Cov(X,Y) - Cov(X,I)Cov(Y,I)/Cov(I,I),$$

where X and Y each represent spectrum intensity for each bin and I represents the control parameter and $$Cov(Y,X) = \langle YX \rangle - \langle Y \rangle \langle X \rangle,$$

where $\langle \ldots \rangle$ represents an average over the plurality of spectra.

12. The method of claim 10 in which determining a statistical significance of each peak or bin comprises computing a statistical significance S(X,Y) according to the equation $$S(X,Y) = p\,Cov(X,Y;I)/\sigma(p\,Cov(X,Y;I))$$

where pCov(X,Y;I) is the value of the partial covariance between bin X and bin Y or a measure of the combined partial covariance between bin or bins X and bin or bins Y and σ(pCov(X,Y;I)) comprises a measure of the variance of the value of the partial covariance between bins X and Y or a measure of the variance of a measure of the combined partial covariance between bin or bins X and bin or bins Y, and I represents the control parameter.

13. The method of claim 1 in which the control parameters comprise an operating parameter or parameters of the apparatus generating the data sets and/or one or more measures of the experimental conditions under which the plurality of spectra was generated.

14. The method of claim 11 in which the method of analysis comprises mass spectrometry and wherein the control parameter or parameters comprises a measure of any of the following operating parameters: ion current for each spectrum; a total number of ions generated for each spectrum; a total number of ions subjected to analysis for each spectrum, a measure of intensity over one or more parts of the spectrum; a prescan ion current; a relative sample density in a mass analyser; a pressure of gas in an ion trap, ion guide and/or collision cell; a rate of flow of ions into a mass analyser; an intensity and/or pulse duration of ionising radiation; electrospray ionisation capillary voltage; rf and dc voltages applied to an ion trap; ion trap q-value; a voltage applied to one or more of a tube lens, gate lens, focusing lens, ion tunnel or multipole ion guide of the mass spectrometer, a time for which a voltage is applied to one or more of a tube lens, gate lens, focusing lens, ion tunnel or multipole ion guide of the mass spectrometer.

15. The method of claim 1 in which the control parameter or parameters comprises a measure of intensity of at least a selected portion of each of the spectra.

16. The method of claim 1 in which the control parameter or parameters are derived from an integration over at least a portion of each spectrum.

17. The method of claim 15 wherein each spectrum relates to mass to charge ratio, kinetic energy or time of flight of analyte particles, absorption or emission frequency or chemical shift.

18. The method of claim 16 wherein the method of analysis comprises mass spectrometry and the control parameter or parameters is or are derived from an integration of the spectra at one or more detected mass to charge ratios (m/z).

19. The method of claim 18 wherein the control parameter comprises or control parameters comprise an integration of the spectrum across all detected mass to charge ratios.

20. The method of claim 15 wherein the method of analysis comprises tandem mass spectrometry.

21. The method of claim 20 wherein the control parameter or parameters is or are derived from an integration of each spectrum at or about an m/z ratio corresponding to a parent ion or neutral loss thereof or a fragment ion or a neutral loss thereof.

22. The method of claim 20 wherein the method of analysis comprises dissociating one or more parent ions by means of one or more of collision induced dissociation (CID), electron transfer dissociation (ETD), electron capture dissociation (ECD), electron detachment dissociation (EDD), photodissociation, laser induced dissociation or surface induced dissociation (SID).

23. The method of claim 1 wherein the sample comprises one or more peptides or proteins.

24. The method of claim 23 wherein, prior to analysing, the sample is exposed to one or more enzymes to at least partially digest one or more of the proteins or peptides present.

25. The method of claim 10 further comprising ranking statistical significance of each spectral correlation in the partial covariance map relative to the most statistically significant peak.

26. The method of claim 25 wherein the spectra are mass spectra and the ranking provides information indicative of a parent ion origin of one or more daughter or granddaughter ions.

27. The method of claim 26 wherein the ranking provides information indicative of the probability of a partial covariance signal representing a true correlation between fragment ions, a true correlation between fragment ions providing information indicative of a parent ion origin of one or more daughter or granddaughter ions.

28. The method of claim 27 wherein the information indicative of the probability of a partial covariance signal representing a true correlation between fragment ions is provided as a map or list of pairs of statistically significant correlating fragment ions.

29. The method of claim 28, wherein the map or list of pairs of statistically significant correlating fragment ions is compared to one or more spectral databases to determine at least part of the structure of the composition of matter.

30. The method of claim 26 wherein the sample comprises one or more proteins or peptides and the information indicative of the parent ion origin of one or more daughter or granddaughter ions is used to determine a structure of the proteins or peptides.

31. The method of claim 30 wherein the sample comprises DNA, human or animal metabolites or lipids and the information indicative of the parent ion origin of one or more daughter or granddaughter ions is used to determine a structure of the DNA, RNA, human or animal metabolites or lipids.

32. The method of claim 24 wherein the digestion is followed by chromatographic separation of the digests of the one or more of the proteins or peptides present.

* * * * *